(12) United States Patent
Hutchinson et al.

(10) Patent No.: US 8,049,015 B2
(45) Date of Patent: Nov. 1, 2011

(54) HETEROARYL ANTAGONISTS OF PROSTAGLANDIN $D_2$ RECEPTORS

(75) Inventors: John Howard Hutchinson, La Jolla, CA (US); Nicholas Simon Stock, San Diego, CA (US); Jeffrey Roger Roppe, Temecula, CA (US); Jill Melissa Scott, Cardiff, CA (US); Brian Andrew Stearns, San Diego, CA (US); Yen Pham Truong, San Diego, CA (US); Deborah Volkots, San Diego, CA (US); Timothy Parr, La Mesa, CA (US)

(73) Assignee: Panmira Pharmaceuticals, LLC, San Diego, CA (US)

( * ) Notice: Subject to any disclaimer, the term of this patent is extended or adjusted under 35 U.S.C. 154(b) by 42 days.

(21) Appl. No.: 12/568,571

(22) Filed: Sep. 28, 2009

(65) Prior Publication Data

US 2010/0081673 A1    Apr. 1, 2010

Related U.S. Application Data

(60) Provisional application No. 61/101,074, filed on Sep. 29, 2008.

(51) Int. Cl.
| | |
|---|---|
| *C07D 213/00* | (2006.01) |
| *C07D 211/72* | (2006.01) |
| *C07D 211/78* | (2006.01) |
| *A61K 31/44* | (2006.01) |

(52) U.S. Cl. ........ 546/329; 546/290; 546/286; 514/344; 514/357

(58) Field of Classification Search .............. 546/329
See application file for complete search history.

(56) References Cited

U.S. PATENT DOCUMENTS

| | | |
|---|---|---|
| 5,239,084 A | 8/1993 | Philippe et al. |
| 5,334,598 A | 8/1994 | Bagley et al. |
| 5,668,176 A | 9/1997 | Bagley et al. |
| 5,827,868 A | 10/1998 | Misra et al. |
| 6,028,080 A | 2/2000 | Ackermann et al. |
| 6,617,351 B1 | 9/2003 | Arnold et al. |
| 6,884,593 B1 | 4/2005 | Hirai et al. |
| 7,144,913 B2 | 12/2006 | Wang et al. |
| 7,205,329 B2 | 4/2007 | Chien et al. |
| 2001/0047027 A1 | 11/2001 | Labelle et al. |
| 2002/0198251 A1 | 12/2002 | Sundermann et al. |
| 2004/0214888 A1 | 10/2004 | Matsuura et al. |
| 2005/0154044 A1 | 7/2005 | Beaulieu et al. |
| 2005/0171143 A1 | 8/2005 | Tanimoto et al. |
| 2005/0272756 A1 | 12/2005 | Leblanc et al. |
| 2006/0100425 A1 | 5/2006 | Bennani et al. |
| 2006/0106081 A1 | 5/2006 | Bennani et al. |
| 2008/0167378 A1 | 7/2008 | Fukatsu et al. |
| 2008/0306109 A1 | 12/2008 | Hynd et al. |
| 2009/0186923 A1 | 7/2009 | Armer et al. |
| 2009/0197959 A1 | 8/2009 | Hutchinson et al. |
| 2010/0004331 A1 | 1/2010 | Hutchinson et al. |
| 2010/0081673 A1 | 4/2010 | Hutchinson et al. |
| 2010/0113503 A1 | 5/2010 | Hutchinson et al. |
| 2010/0173313 A1 | 7/2010 | Bain et al. |
| 2010/0280049 A1 | 11/2010 | Stearns et al. |
| 2010/0298368 A1 | 11/2010 | Stearns et al. |
| 2011/0021573 A1 | 1/2011 | Hutchinson et al. |
| 2011/0034558 A1 | 2/2011 | Brittain et al. |
| 2011/0039852 A1 | 2/2011 | Hutchinson et al. |

FOREIGN PATENT DOCUMENTS

| | | |
|---|---|---|
| EP | 1170594 A2 | 1/2002 |
| GB | 2460597 B | 4/2010 |
| GB | 2461629 B | 5/2010 |
| GB | 2463788 B | 12/2010 |
| JP | 2004-182657 A | 7/2004 |
| WO | WO-95-03044 | 2/1995 |
| WO | WO-99-11605 A1 | 3/1999 |
| WO | WO-03-006011 A1 | 1/2003 |
| WO | WO-2003-062200 A2 | 7/2003 |
| WO | WO-2004-035543 A1 | 4/2004 |
| WO | WO-2004-058164 A2 | 7/2004 |
| WO | WO-2004-096777 A1 | 11/2004 |
| WO | WO-2005-019161 A1 | 3/2005 |
| WO | WO-2005-040114 A1 | 5/2005 |
| WO | WO-2005-044260 A1 | 5/2005 |
| WO | WO-2005-051373 A1 | 6/2005 |
| WO | WO-2005-100298 A1 | 10/2005 |
| WO | WO-2006-002099 A2 | 1/2006 |
| WO | WO-2006-005909 A1 | 1/2006 |
| WO | WO-2006-014357 A1 | 2/2006 |
| WO | WO-2006-015158 A1 | 2/2006 |
| WO | WO-2006-037982 A2 | 4/2006 |
| WO | WO-2006-044732 A2 | 4/2006 |
| WO | WO-2006-052798 A2 | 5/2006 |
| WO | WO-2006-053791 A2 | 5/2006 |
| WO | WO-2006-056854 A1 | 6/2006 |

(Continued)

OTHER PUBLICATIONS

Srinivas et al., "Biaryl amino acid templates in place of D-Pro-L-Pro in cyclic beta-hairpin cationic antimicrobial peptidomimetics," Organic & Biomolecular Chemistry 5(19):3100-3105 (2007).
PCT/US10/43599 Search Report and Written Opinion mailed Apr. 28, 2011.
PCT/US10/43598 Search Report and Written Opinion mailed Apr. 20, 2011.
Torisu et al., "Discovery of new chemical leads for prostaglandin D2 receptor antagonists," Bioorg. Med. Chem. Ltrs. 14:4557-4562 (2004).
PCT/US09/58655 Search Report and Written Opinion dated May 10, 2010.

(Continued)

*Primary Examiner* — Janet Andres
*Assistant Examiner* — Heidi Reese
(74) *Attorney, Agent, or Firm* — Wilson Sonsini Goodrich & Rosati

(57) ABSTRACT

Described herein are compounds that are antagonists of $PGD_2$ receptors. Also described are pharmaceutical compositions that include the compounds described herein, and methods of using such antagonists of $PGD_2$ receptors, alone or in combination with other compounds, for treating respiratory, cardiovascular, and other $PGD_2$-dependent or $PGD_2$-mediated conditions or diseases.

36 Claims, 4 Drawing Sheets

FOREIGN PATENT DOCUMENTS

| | | |
|---|---|---|
| WO | WO-2006-070325 A2 | 7/2006 |
| WO | WO-2006-090915 A1 | 8/2006 |
| WO | WO-2006-091496 A2 | 8/2006 |
| WO | WO-2006-125596 A1 | 11/2006 |
| WO | WO-2007-024922 A1 | 3/2007 |
| WO | WO-2007-037187 A1 | 4/2007 |
| WO | WO-2007-039736 A1 | 4/2007 |
| WO | WO-2007-068894 A2 | 6/2007 |
| WO | WO-2007-088996 A1 | 8/2007 |
| WO | WO-2007-107772 A1 | 9/2007 |
| WO | WO-2007-144127 A1 | 12/2007 |
| WO | WO-2008-017989 A1 | 2/2008 |
| WO | WO-2008-024746 A1 | 2/2008 |
| WO | WO-2008-033455 A2 | 3/2008 |
| WO | WO-2008-082567 A1 | 7/2008 |
| WO | WO-2008-137027 A2 | 11/2008 |
| WO | WO-2008-156780 A1 | 12/2008 |
| WO | WO-2009-004379 A1 | 1/2009 |
| WO | WO-2009-044147 A1 | 4/2009 |
| WO | WO-2009-063202 A2 | 5/2009 |
| WO | WO-2009-063215 A2 | 5/2009 |
| WO | WO-2009-089192 A1 | 7/2009 |
| WO | WO-2009-099901 A1 | 8/2009 |
| WO | WO-2009-099902 A1 | 8/2009 |
| WO | WO-2009-102893 A2 | 8/2009 |
| WO | WO-2009-108720 A2 | 9/2009 |
| WO | WO-2009-145989 A2 | 12/2009 |
| WO | WO-2010-003120 A2 | 1/2010 |
| WO | WO-2010-003120 A2 | 1/2010 |
| WO | WO-2010-003127 A2 | 1/2010 |
| WO | WO-2010-037054 A2 | 4/2010 |
| WO | WO-2010-037059 A2 | 4/2010 |
| WO | WO-2010-039977 A2 | 4/2010 |
| WO | WO-2010-042652 A2 | 4/2010 |
| WO | WO-2010-057118 A2 | 5/2010 |
| WO | WO-2011-014587 A2 | 2/2011 |
| WO | WO-2011-014588 A2 | 2/2011 |
| WO | WO-2011-017201 A2 | 2/2011 |

OTHER PUBLICATIONS

Arima and Fukuda, "Prostaglandin D2 Receptors DP and CRTH2 in the Pathogenesis of Asthma," Curr. Mol. Med. 8:365-375 (2008).
Hata and Breyer, "Pharmacology and signaling of prostaglandin receptors: Multiple roles in inflammation and immune modulation," Pharmacol. Ther. 103:147-166 (2004).
Kostenis and Ulven, "Emerging roles of DP and CRTH2 in allergic inflammation," Trends Mol. Med. 12(4):148-158 (2006).
Medina and Liu, "PGD2 Antagonists," Annual Reports Med. Chem. 41:221-235 (2006).
Pettipher et al., "Antagonism of the prostaglandin D2 receptors DP1 and CRTH2 as an approach to treat allergic diseases," Nature Reviews/Drug Discovery 6:313-325 (2007).
Science IP Structure Search dated Jul. 8, 2008.
Science IP Structure Search dated Aug. 15, 2008.
Tirouvanziam et al., "Profound functional and signaling changes in viable inflammatory neutrophils homing to cystic fibrosis airways," PNAS 105(11):4335-4339 (2008).
Ulven and Kostenis, "Targeting the Prostaglandin D2 Receptors DP and CRTH2 for Treatment of Inflammation," Curr. Topics Med. Chem. 6:1427-1444 (2006).
GB 0916810.5 Search Report dated Dec. 10, 2009.
Crosignani et al., "Discovery of a new class of potent, selective, and orally bioavailable CRTH2(DP2) receptor antagonists for the treatment of allergic inflammatory diseases" J Med Chem 51:2227-2243 (2008).
Evans et al., "Seeing the future of bioactive lipid drug targets," Nature Chem Biol 6:476-479 (2010).
Kim et al., "Regulation of Immune Cells by Eicosanoid Receptors," TheScientificWorld Journal 7:1307-1328 (2007).
Ly and Bacon, "Small-molecule CRTH2 antagonists for the treatment of allergic inflammation: an overview," Exp Opin Invest Drugs 14:769 (2005).
Pettipher et al., "The roles of the prostaglandin D(2) receptors DP(1) and CRTH2 in promoting allergic responses," Br J Pharmacol 153:S191 (2008).
Pettipher et al., "Antagonists of the prostaglandin D2 receptor CRTH2," Drug News Perspect 21:317-322 (2008).
Prieto et al., "Racemization in Suzuki couplings: a quantitative study using 4-hydroxyphenylglycine and tyrosine derivatives as probe molecules," J Org Chem 72(3):1047-1049 (2007).
Sandham et al., "7-Azaindole-3-acetic acid derivatives: potent and selective CRTH2 receptor antagonists," Bioorg Med Chem Lett 19:4794-4798 (2009).
Sandig et al., "Contrary prostaglandins: the opposing roles of PGD2 and its metabolites in leukocyte function," J Leukocyte Biology 81:372-382 (2007).
Scott et al., "Discovery and optimization of a biphenylacetic acid series of prostaglandin D2 receptor DP2 antagonists with efficacy in a murine model of allergic rhinitis," Bioorg Med Chem Ltrs (2011), doi: 10.1016fj.bmcl.2011.01.024.
Shrader et al., "Factor VIIa inhibitors: Gaining selectivity within the trypsin family," Bioorg Med Chem Ltrs 16(6):1596-1600 (2006).
Stearns et al., "Novel tricyclic antagonists of the prostaglandin D2 receptor DP2 with efficacy in a murine model of allergic rhinitis," Bioorg Med Chem Ltrs 19:4647-4651 (2009).
Stebbins et al., "DP2 Receptor Antagonists: Novel Therapeutic Target for COPD," Mol Cell Pharmacol 2(3):89-96 (2010).
Stebbins et al., "Pharmacological Blockade of the DP2 Receptor Inhibits Cigarette Smoke-Induced Inflammation, Mucus Cell Metaplasia, and Epithelial Hyperplasia in the Mouse Lung," J Pharmacol Exp Ther 332(3):764-775 (2010).
Stebbins et al., "Therapeutic efficacy of AM156, a novel prostanoid DP2 receptor antagonist, in murine models of allergic rhinitis and house dust mite-induced pulmonary inflammation," Eur J Pharmacol 638:142-149 (2010).
Stock et al., "Sodium [2'-[(cyclopropanecarbonyl-ethyl-amino)-methyl]-4'-(6- ethoxy-pyridin-3-yl)-6-methoxy-biphenyl-3-yl]-acetate (AM432): A potent, selective prostaglandin D2 receptor antagonist," Bioorg Med Chem Ltrs 21:1036-1040 (2011).
Takeshita et al., "CRTH2 is a prominent effector in contact hypersensitivity-induced neutrophil inflammation," Intl Immunol 16(7):947,959 (2004).
Ulven et al., "Minor Structural Modifications Cover the Dual TP/CRTH2," J Med Chem 48(4):897-900 (2005).
EP09709954.3 Search Report mailed Feb. 21, 2011.
PCT/US09/64630 Search Report and Written Opinion mailed Jul. 19, 2010.
PCT/US09/59891 Search Report and Written Opinion mailed May 24, 2010.
PCT/US09/59256 Search Report and Written Opinion mailed Jun. 21, 2010.
PCT/US09/58663 Search Report and Written Opinion mailed May 14, 2010.
PCT/US09/58655 Search Report and Written Opinion mailed May 10, 2010.
PCT/US09/49631 Search Report mailed Feb. 24, 2010.
PCT/US09/49631 Written Opinion mailed Feb. 24, 2010.
PCT/US09/49621 Search Report and Written Opinion mailed Mar. 15, 2010.
PCT/US09/38291 Search Report and Written Opinion mailed Nov. 27, 2009.
PCT/US09/35174 IPER and Written Opinion mailed Sep. 10, 2010.
PCT/US09/33961 Search Report mailed Aug. 11, 2009.
PCT/US09/33961 IPER and Written Opinion mailed Aug. 26, 2010.
PCT/US09/32499 Search Report and Written Opinion mailed Jun. 29, 2009.
PCT/US09/32495 Search Report and Written Opinion mailed Jun. 29, 2009.

Compound 1

Compound 5

Compound 9

Compound 2

Compound 6

Compound 10

Compound 3

Compound 7

Compound 11

Compound 4

Compound 8

Compound 12

Compound 13

Compound 17

Compound 21

Compound 14

Compound 18

Compound 22

Compound 15

Compound 19

Compound 23

Compound 16

Compound 20

Compound 24

Compound 25

Compound 29

Compound 33

Compound 26

Compound 30

Compound 34

Compound 27

Compound 31

Compound 35

Compound 28

Compound 32

Compound 36

Compound 37

Compound 39

Compound 42

Compound 38

Compound 40

Compound 43

Compound 41

HETEROARYL ANTAGONISTS OF PROSTAGLANDIN D₂ RECEPTORS

RELATED APPLICATIONS

This application claims the benefit of U.S. provisional patent application No. 61/101,074 entitled "HETEROARYL ANTAGONISTS OF PROSTAGLANDIN D₂ RECEPTORS" filed on Sep. 29, 2008, which is incorporated by reference in its entirety.

FIELD OF THE INVENTION

Described herein are compounds, methods of making such compounds, pharmaceutical compositions comprising such compounds, and methods of using such compounds to treat, prevent or diagnose diseases or conditions associated with prostaglandin $D_2$.

BACKGROUND OF THE INVENTION

Prostaglandins have a diverse range of activities and have a well recognized role in pain and inflammation. Prostaglandin $D_2$ ($PGD_2$) is produced by mast cells, macrophages and Th2 lymphocytes in response to local tissue damage as well as allergic inflammation in diseases such as asthma, rhinitis, and atopic dermatitis. $PGD_2$ binds to a number of receptors, which include the thromboxane-type prostanoid (TP) receptor, $PGD_2$ receptor (DP, also known as $DP_1$) and chemoattractant receptor-homologous molecule expressed on Th2 cells (CRTH2; also known as $DP_2$).

SUMMARY OF THE INVENTION

Presented herein are compounds, pharmaceutical compositions, and methods, for (a) diagnosing, preventing, or treating allergic and non-allergic inflammation, (b) mitigating adverse signs and symptoms that are associated with inflammation, and/or (c) controlling immunological, proliferative disorders. These disorders may arise from one or more of a genetic, iatrogenic, immunological, infectious, oncological, toxic, surgical, and/or traumatic etiology. In one aspect, the methods, compounds, pharmaceutical compositions, and medicaments described herein comprise antagonists of $PGD_2$ receptors. In one aspect, the methods, compounds, pharmaceutical compositions, described herein comprise antagonists of $DP_2$.

In one aspect provided herein are compounds of Formula (I), pharmaceutically acceptable salts, pharmaceutically acceptable prodrugs, and pharmaceutically acceptable solvates thereof, which are antagonists of $DP_2$, and are used to treat mammals suffering from one or more $PGD_2$-dependent conditions or diseases, including, but not limited to, asthma, rhinitis, allergic conjuctivitis, atopic dermatitis, chronic obstructive pulmonary disease (COPD), pulmonary hypertension, interstitial lung fibrosis, arthritis, allergy, psoriasis, inflammatory bowel disease, adult respiratory distress syndrome, myocardial infarction, aneurysm, stroke, cancer, wound healing, endotoxic shock, pain, inflammatory conditions, eosinophilic esophagitis, eosinophil-associated gastrointestinal disorders (EGID), idiopathic hypereosinophilic syndrome, otitis, airway constriction, mucus secretion, nasal congestion, increased microvascular permeability and recruitment of eosinophils, urticaria, sinusitis, angioedema, anaphylaxis, chronic cough and Churg Strauss syndrome.

In one aspect, provided is a compound having the structure of Formula (I), or pharmaceutically acceptable salt, or N-oxide thereof:

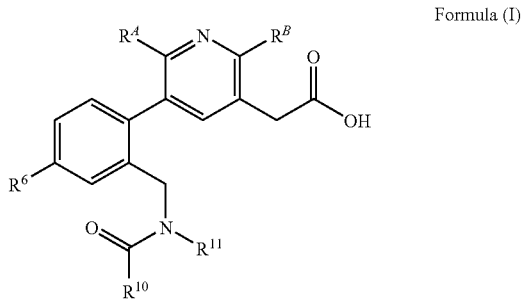

Formula (I)

wherein,
$R^A$ is H, halogen, —CN, —OH, $C_1$-$C_4$alkyl, $C_1$-$C_4$fluoroalkyl, $C_1$-$C_4$fluoroalkoxy, or $C_1$-$C_4$alkoxy;
$R^B$ is H, halogen, —CN, —OH, $C_1$-$C_4$alkyl, $C_1$-$C_4$fluoroalkyl, $C_1$-$C_4$fluoroalkoxy, or $C_1$-$C_4$alkoxy;
$R^6$ is H, halogen, —CN, tetrazolyl, —OH, —$SR^{13}$, —S(=O)$R^{12}$, —S(=O)$_2R^{12}$, —NHS(=O)$_2R^{12}$, —C(=O)$R^{12}$, —OC(=O)$R^{12}$, —CO$_2R^{13}$, —N($R^{13}$)$_2$, —C(=O)N($R^{13}$)$_2$, —NHC(=O)$R^{12}$, $C_1$-$C_4$alkyl, $C_1$-$C_4$fluoroalkyl, $C_1$-$C_4$fluoroalkoxy, $C_1$-$C_4$alkoxy, or $C_1$-$C_4$heteroalkyl;
$R_{10}$ is $C_1$-$C_4$alkyl, $C_1$-$C_4$fluoroalkyl, $C_3$-$C_6$cycloalkyl, a substituted or unsubstituted phenyl, a substituted or unsubstituted 6-membered heteroaryl containing 1 or 2 N atom, —$C_1$-$C_2$alkyl-(substituted or unsubstituted phenyl), —$C_1$-$C_2$alkyl-(substituted or unsubstituted 6-membered heteroaryl containing 1 or 2 N atom), —$C_1$-$C_2$alkyl-O—$C_1$-$C_4$alkyl, —O—$C_1$-$C_4$alkyl, —O—$C_1$-$C_2$alkyl-(substituted or unsubstituted phenyl), —$NR^{16}C_1$-$C_4$alkyl, or —$NR^{16}C_1$-$C_2$alkyl-(substituted or unsubstituted phenyl);
$R^{11}$ is $C_1$-$C_4$alkyl, $C_1$-$C_4$haloalkyl, $C_3$-$C_6$cycloalkyl, or substituted or unsubstituted benzyl;
$R^{12}$ is $C_1$-$C_4$alkyl, $C_1$-$C_4$heteroalkyl, or $C_1$-$C_4$fluoroalkyl;
each $R^{13}$ is independently selected from H, $C_1$-$C_4$alkyl, $C_1$-$C_4$heteroalkyl, $C_1$-$C_4$fluoroalkyl, or substituted or unsubstituted benzyl;
$R^{16}$ is H or $C_1$-$C_4$alkyl;
where each substituted phenyl or substituted heteroaryl is substituted with 1 or 2 $R^C$, where each $R^C$ is independently selected from halogen, —OH, $C_1$-$C_4$alkyl, $C_1$-$C_4$fluoroalkyl, $C_1$-$C_4$fluoroalkoxy, and $C_1$-$C_4$alkoxy.

In one aspect, presented herein are the compounds of Formula (I) presented in FIGS. 1 to 4, or pharmaceutically acceptable salts, pharmaceutically active metabolites, pharmaceutically acceptable prodrugs, N-oxides and pharmaceutically acceptable solvates thereof.

In one aspect, presented herein are the compounds of Formula (I) presented in Table 1, or pharmaceutically acceptable salts, pharmaceutically active metabolites, pharmaceutically acceptable prodrugs, and pharmaceutically acceptable solvates thereof.

Compounds of Formula (I) are antagonists of $DP_2$.

In one aspect, provided herein are pharmaceutical compositions comprising a therapeutically effective amount of a compound of Formula (I). In some embodiments, the pharmaceutical compositions comprise at least one inactive pharmaceutically acceptable inactive ingredient selected from excipients, diluents, and carriers.

In certain embodiments, presented herein are methods for treating a PGD$_2$-dependent condition or disease in a mammal comprising administering to the mammal a therapeutically effective amount of a compound of Formula (I).

In another aspect, compounds of Formula (I) are used to treat or prevent inflammatory diseases or conditions. Inflammatory conditions include, but are not limited to, asthma, rhinitis, chronic obstructive pulmonary disease, pulmonary hypertension, interstitial lung fibrosis, atherosclerosis, aortic aneurysm, myocardial infarction, and stroke.

In a specific aspect, provided herein is a method for treating asthma in a mammal comprising administering a therapeutically effective amount of a compound provided herein to the mammal in need.

In another aspect, compounds of Formula (I) are used to treat or prevent immunological disorders, including, but are not limited to, allergy or to excessive or inappropriate response to an endogenous or exogenous antigen. In certain embodiments, the immunological disorder that is characterized by immune dysregulation that is not accompanied by inflammation.

In additional aspects, such diseases or conditions are iatrogenic and increases in, or abnormal localization of, PGD$_2$ is induced by other therapies or medical or surgical procedures. In other embodiments, the PGD$_2$-dependent or PGD$_2$ mediated condition or disease is caused by surgery.

In another aspect are methods for treating respiratory diseases or conditions in a mammal comprising administering to the mammal at least once an effective amount of at least one compound of Formula (I). In a further embodiment of this aspect, the respiratory disease is asthma. In a further embodiment of this aspect, the respiratory disease includes, but is not limited to, asthma, adult respiratory distress syndrome, allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, neutrophillic asthma, isocapnic hyperventilation, child-onset asthma, adult-onset asthma, cough-variant asthma, occupational asthma, steroid-resistant asthma, seasonal asthma, seasonal allergic rhinitis, perennial allergic rhinitis, chronic obstructive pulmonary disease, including chronic bronchitis or emphysema, pulmonary hypertension, interstitial lung fibrosis and/or airway inflammation and cystic fibrosis, and hypoxia.

In another aspect compounds described herein are used for treating rhinitis in a mammal. In a further embodiment of this aspect, compounds described herein are used for treating allergic (extrinsic) rhinitis, non-allergic (intrinsic) rhinitis, chronic rhinitis, allergen-induced rhinitis, aspirin-sensitive rhinitis, child-onset rhinitis, adult-onset rhinitis, occupational rhinitis, steroid-resistant rhinitis, seasonal rhinitis, perennial rhinitis, rhinosinusitis, and rhinopolyposis.

In another aspect are methods for treating chronic obstructive pulmonary disease comprising administering to the mammal at least once an effective amount of a compound of Formula (I). In a further embodiment of this aspect, chronic obstructive pulmonary disease includes, but is not limited to, chronic bronchitis and/or emphysema, pulmonary hypertension, interstitial lung fibrosis and/or airway inflammation and cystic fibrosis.

In another aspect are methods for preventing increased mucosal secretion and/or edema in mammals comprising administering to the mammal at least once an effective amount of a compound of Formula (I).

In another aspect are methods for preventing eosinophil and/or basophil and/or dendritic cell and/or neutrophil and/or monocyte or Th2 cell recruitment comprising administering to the mammal an effective amount of a compound of Formula (I).

In another aspect are methods for treating or preventing ocular inflammation, conjunctivitis, retinitis, scleritis, uveitis, allergic conjunctivitis, vernal keratoconjunctivitis, and papillary conjunctivitis comprising administering to the mammal at least once an effective amount of a compound of Formula (I).

In another aspect, compounds of Formula (I) are used to treat or prevent pain.

In another aspect are methods for preventing or treating acute or chronic disorders involving recruitment or activation of eosinophils comprising administering to the mammal at least once an effective amount of a compound of Formula (I).

In another aspect are methods for treating inflammatory responses of the skin comprising administering to the mammal at least once an effective amount of at least one compound of Formula (I). Such inflammatory responses of the skin include, by way of example, psoriasis, dermatitis, atopic dermatitis, contact dermatitis, eczema, urticaria, rosacea, bullous disorders, collagenoses, Kawasaki Disease, Sjogren-Larsso Syndrome, wound healing and scarring. In another aspect are methods for reducing psoriatic lesions in the skin, joints, or other tissues or organs, comprising administering to the mammal an effective amount of a compound of Formula (I). In another aspect are methods for reducing psoriatic lesions in the skin, joints, or other tissues or organs, comprising administering at least once to the mammal an effective amount of a compound of Formula (I).

In a further aspect are methods to modulate the immune response to endogenous or exogenous antigens. In a further aspect are methods to treat acute or chronic allergic responses to exogenous substances that have been ingested such as foods (e.g., peanuts) or drugs (e.g., penicillin, non-steroidal anti-inflammatory drugs or the like).

In another aspect is the use of a compound of Formula (I) in the manufacture of a medicament for treating an inflammatory disease or condition in a mammal in which the activity of at least one PGD$_2$-associated protein contributes to the pathology and/or symptoms of the disease or condition. In one embodiment of this aspect, the PGD$_2$ pathway protein is DP2. In another or further embodiment of this aspect, the inflammatory disease or conditions are respiratory, cardiovascular, or proliferative diseases.

"Cardiovascular disease or conditions," refers to diseases affecting the heart or blood vessels or both, including but not limited to: arrhythmia (atrial or ventricular or both); atherosclerosis and its sequelae; angina; cardiac rhythm disturbances; myocardial ischemia; myocardial infarction; cardiac or vascular aneurysm; vasculitis, stroke; peripheral obstructive arteriopathy of a limb, an organ, or a tissue; reperfusion injury following ischemia of the brain, heart or other organ or tissue; endotoxic, surgical, or traumatic shock; hypertension, valvular heart disease, heart failure, abnormal blood pressure; shock; vasoconstriction (including that associated with migraines); vascular abnormality, inflammation, insufficiency limited to a single organ or tissue.

In any of the aforementioned aspects are further embodiments in which: (a) the effective amount of the compound is systemically administered to the mammal; and/or (b) the effective amount of the compound is administered orally to the mammal; and/or (c) the effective amount of the compound is intravenously administered to the mammal; and/or (d) the effective amount of the compound administered by inhalation; and/or (e) the effective amount of the compound is administered by nasal administration; or and/or (f) the effective amount of the compound is administered by injection to the mammal; and/or (g) the effective amount of the compound is administered topically (dermal) to the mammal; and/or (h) the effective amount of the compound is administered by ophthalmic administration; and/or (i) the effective amount of the compound is administered rectally to the mammal.

In any of the aforementioned aspects are further embodiments comprising single administrations of the effective amount of the compound, including further embodiments in which (i) the compound is administered once; (ii) the compound is administered to the mammal multiple times over the span of one day; (iii) continually; or (iv) continuously.

In any of the aforementioned aspects are further embodiments comprising multiple administrations of the effective amount of the compound, including further embodiments in which (i) the compound is administered once daily; (ii) the compound is administered twice daily; (iii) the compound is administered in cycles that include daily administration for a period of time followed by at least 1 day without administration; (iv) the compound is administered in cycles that include daily administration for a period of time followed by at least 1 day that includes a dose reduction in the daily amount of compound that is administered.

In any of the aforementioned aspects involving the treatment of $PGD_2$ dependent diseases or conditions are further embodiments comprising administering at least one additional agent in addition to the administration of a compound having the structure of Formula (I).

In any of the aforementioned aspects involving the prevention or treatment of inflammation are further embodiments comprising: (a) monitoring inflammation in a mammal; (b) measuring bronchoconstriction in a mammal; (c) measuring eosinophil and/or basophil and/or dendritic cell and/or neutrophil and/or monocyte and/or lymphocyte recruitment in a mammal; (d) monitoring mucosal secretion in a mammal; (e) measuring mucosal edema in a mammal.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

DETAILED DESCRIPTION OF THE INVENTION

Figure 1:
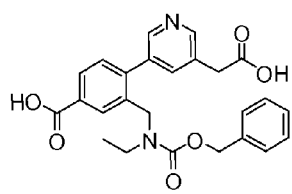
FIG. 1. Illustrative examples of compounds described herein.
Figure 1:
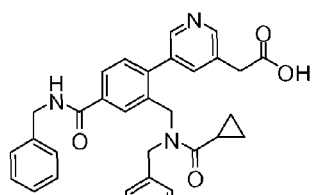
Figure 1:
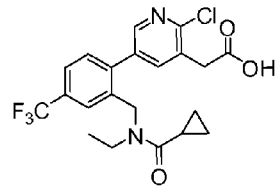
Figure 1:
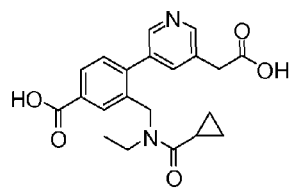
Figure 1:
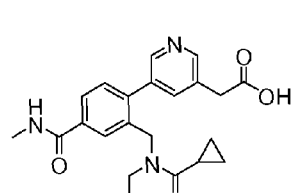
Figure 1:
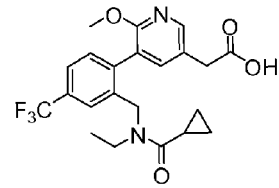
Figure 1:
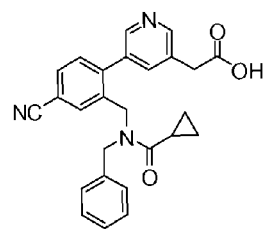
Figure 1:
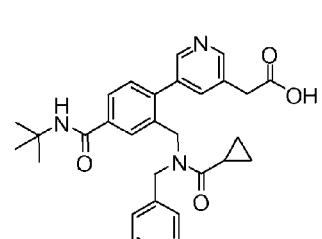
Figure 1:
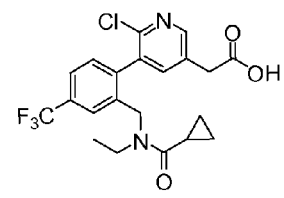
Figure 1:
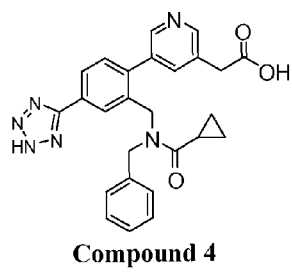
Figure 1:
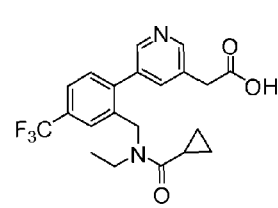
Figure 1:
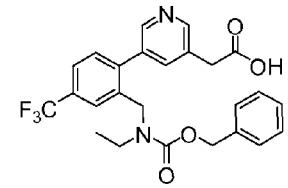
Figure 2:
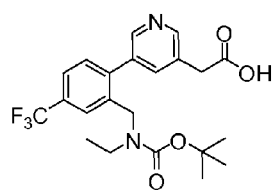
FIG. 2. Illustrative examples of compounds described herein.
Figure 2:
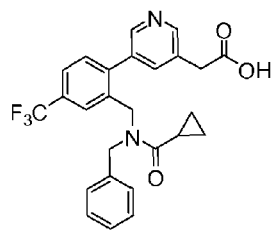
Figure 2:
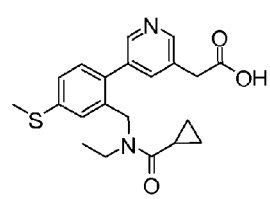
Figure 2:
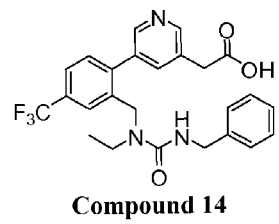
Figure 2:
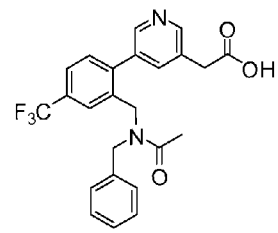
Figure 2:
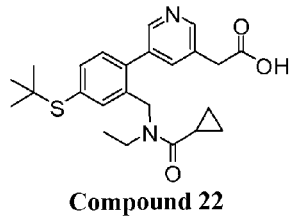
Figure 2:
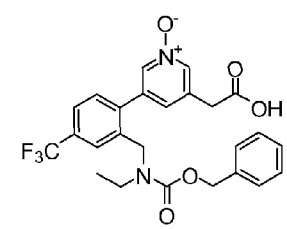
Figure 2:
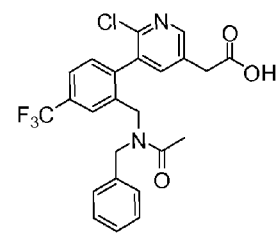
Figure 2:
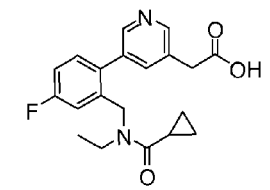
Figure 2:
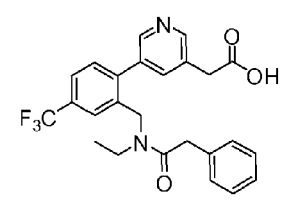
Figure 2:
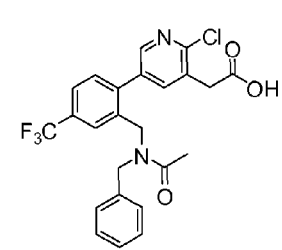
Figure 2:
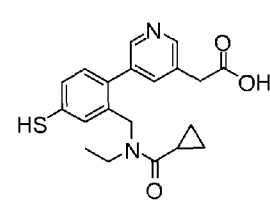
Figure 3:
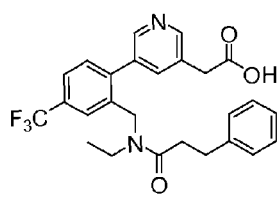
FIG. 3. Illustrative examples of compounds described herein.
Figure 3:
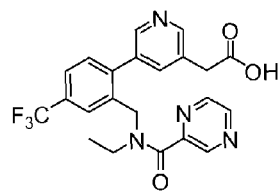
Figure 3:
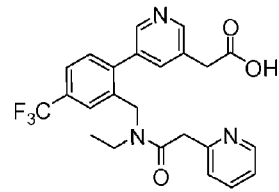
Figure 3:
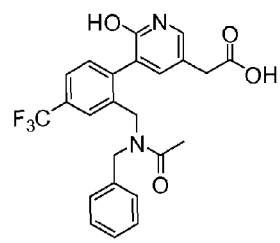
Figure 3:
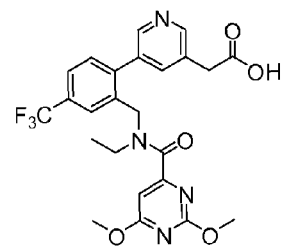
Figure 3:
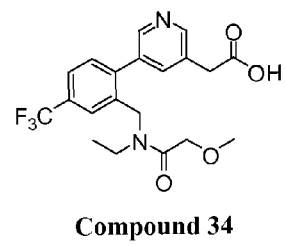
Figure 3:
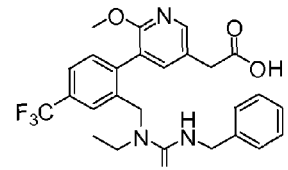
Figure 3:
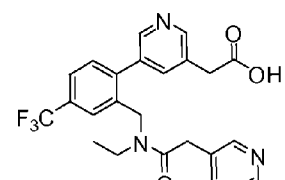
Figure 3:
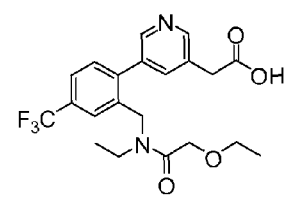
Figure 3:
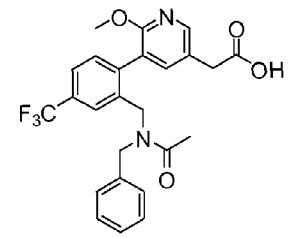
Figure 3:
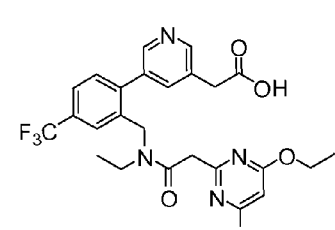
Figure 3:
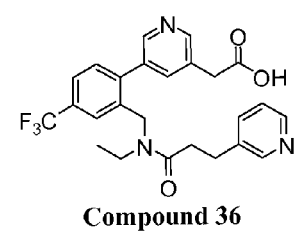
Figure 4:
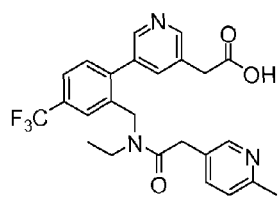
FIG. 4. Illustrative examples of compounds described herein.
Figure 4:
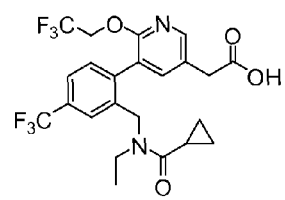
Figure 4:
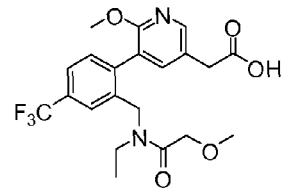
Figure 4:
Figure 4:
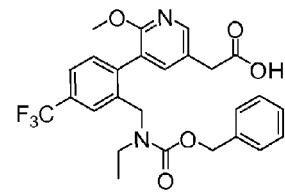
Figure 4:
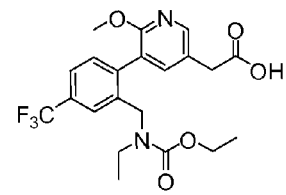
Figure 4:
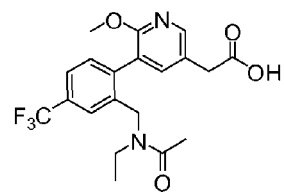

Prostaglandin $D_2$ ($PGD_2$) is an acidic lipid derived from the metabolism of arachidonic acid by cyclooxygenases and $PGD_2$ synthases. $PGD_2$ is produced by mast cells, macrophages and Th2 lymphocytes in response to local tissue damage as well as in response allergic inflammation observed in diseases such as asthma, rhinitis, and atopic dermatitis. Exogenous $PGD_2$ applied to bronchial airways elicits many responses that are characteristic of acute asthma.

Activation of $DP_2$ is associated with chemotaxis and activation of Th2 lymphocytes, eosinophils and basophils. $PGD_2$ binds to $DP_2$ and mediates many of its effects through a $G_i$-dependent elevation of intracellular calcium levels and reduction of cyclic AMP. In Th2 lymphocytes, IL4, IL5 and IL13 cytokine production are also stimulated by $DP_2$ activation. These cytokines have been implicated in numerous biological actions including, by way of example only, immunoglobulin E production, airway response, mucous secretion, and eosinophil recruitment.

In the brain and central nervous system, $PGD_2$ is produced and thought to function in pain perception and sleep regulation. In other tissues, $PGD_2$ is produced primarily in immunoglobulin E (IgE) activated mast cells and to a lesser extent, in macrophages, dendritic cells, T helper 2 (Th2) lymphocytes and other leukocytes. In the cell, $PGD_2$ is rapidly metabolized and converted to other downstream effectors including $\Delta^{12}PGJ_2$, $9\alpha11\beta PGF_2$, 13,14-dihydro-15-keto-$PGD_2$, and 15-deoxy-$\Delta^{12,14}PGD_2$.

Mast-cell-derived $PGD_2$ is produced in high concentrations in response to an allergen challenge. Studies in preclinical species have observed the following features when $PGD_2$ is applied to in vivo preparations, or its overproduction is engineered by genetic manipulation: vasodilatation leading to erythema (flare) and potentiation of oedema (wheal), recruitment of eosinophils and Th2 lymphocytes, modulation of Th2-cytokine production, bronchoconstriction.

Injection of $PGD_2$ into human skin has been shown to produce a long lasting erythema, to potentiate the effects of other mediators on induration and leukocyte infiltration in human skin and to enhance oedema formation in rat skin. It is most likely that these effects of $PGD_2$, like those of other vasodilator prostaglandins, are due to an increased blood flow to the inflamed lesion and are, therefore, most likely to be mediated predominantly by the $DP_1$ receptor. Although these observations make it clear that $DP_1$ mediates the vascular effects of $PGD_2$, the capacity of $PGD_2$ to promote the cellular changes associated with inflammation is not due to an action on $DP_1$.

Much of $PGD_2$'s pro-inflammatory activity is through interaction with $DP_2$. $DP_2$ is a G-protein coupled receptor and is typically highly expressed in Th2 lymphocytes, eosinophils and basophils. $DP_2$ activation functions to directly activate and recruit Th2 lymphocytes and eosinophils. Activated Th2 lymphocytes produce and secrete inflammatory cytokines including IL4, IL5, and IL13. Despite binding $PGD_2$ with a similar affinity as $DP_1$, $DP_2$ is not structurally related to $DP_1$ and signals through a different mechanism—the effects of $DP_2$ are mediated through Gi-dependent elevation in intracellular calcium levels and reduction in intracellular levels of cyclic AMP. $DP_2$ activation is important in eosinophil recruitment in response to allergic challenge in such tissues as nasal mucosa, bronchial airways, and skin. The application of either $PGD_2$ or selective $DP_2$ agonists both exacerbate and enhance allergic responses in lung and skin. $DP_2$ activation appears to have a crucial role in mediating allergic responses. The use of antagonists of $PGD_2$ activation of the $DP_2$ receptor is an approach to treat the inflammatory component of inflammatory diseases or conditions, respiratory diseases or conditions, allergic diseases or conditions, such as asthma, rhinitis, and dermatitis, among others.

Compounds

Compounds of Formula (I) have the following structure:

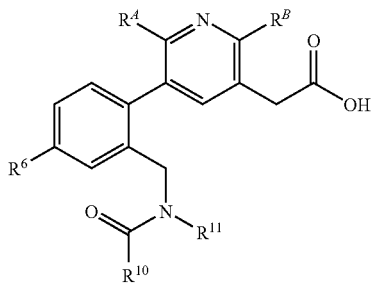

Formula (I)

wherein, $R^A$ is H, halogen, —CN, —OH, $C_1$-$C_4$alkyl, $C_1$-$C_4$fluoroalkyl, $C_1$-$C_4$fluoroalkoxy, or $C_1$-$C_4$alkoxy;

$R^B$ is H, halogen, —CN, —OH, $C_1$-$C_4$alkyl, $C_1$-$C_4$fluoroalkyl, $C_1$-$C_4$fluoroalkoxy, or $C_1$-$C_4$alkoxy;

$R^6$ is H, halogen, —CN, tetrazolyl, —OH, —$SR^{13}$, —S(=O)$R^{12}$, —S(=O)$_2R^{12}$, —NHS(=O)$_2R^{12}$, —C(=O)$R^{12}$, —OC(=O)$R^{12}$, —CO$_2R^{13}$, —N($R^{13}$)$_2$, —C(=O)N($R^{13}$)$_2$, —NHC(=O)$R^{12}$, $C_1$-$C_4$alkyl, $C_1$-$C_4$fluoroalkyl, $C_1$-$C_4$fluoroalkoxy, $C_1$-$C_4$alkoxy, or $C_1$-$C_4$heteroalkyl;

$R^{10}$ is $C_1$-$C_4$alkyl, $C_1$-$C_4$fluoroalkyl, $C_3$-$C_6$cycloalkyl, a substituted or unsubstituted phenyl, a substituted or unsubstituted 6-membered heteroaryl containing 1 or 2 N atom, —$C_1$-$C_2$alkyl-(substituted or unsubstituted phenyl), —$C_1$-$C_2$alkyl-(substituted or unsubstituted 6-membered heteroaryl containing 1 or 2 N atom), —$C_1$-$C_2$alkyl-O—$C_1$-$C_4$alkyl, —O—$C_1$-$C_4$alkyl, —O—$C_1$-$C_2$alkyl-(substituted or unsubstituted phenyl), —$NR^{16}C_1$-$C_4$alkyl, or —$NR^{16}C_1$-$C_2$alkyl-(substituted or unsubstituted phenyl);

$R^{11}$ is $C_1$-$C_4$alkyl, $C_1$-$C_4$haloalkyl, $C_3$-$C_6$cycloalkyl, or substituted or unsubstituted benzyl;

$R^{12}$ is $C_1$-$C_4$alkyl, $C_1$-$C_4$heteroalkyl, or $C_1$-$C_4$fluoroalkyl;

each $R^{13}$ is independently selected from H, $C_1$-$C_4$alkyl, $C_1$-$C_4$heteroalkyl, $C_1$-$C_4$fluoroalkyl, or substituted or unsubstituted benzyl;

$R^{16}$ is H or $C_1$-$C_4$alkyl;

where each substituted phenyl or substituted heteroaryl is substituted with 1 or 2 $R^C$, where each $R^C$ is independently selected from halogen, —OH, $C_1$-$C_4$alkyl, $C_1$-$C_4$fluoroalkyl, $C_1$-$C_4$fluoroalkoxy, and $C_1$-$C_4$alkoxy.

For any and all of the embodiments, substituents can be selected from among from a subset of the listed alternatives. For example, in some embodiments, $R^A$ is H, F, Cl, Br, —CN, —OH, —CH$_3$, —CF$_3$, —OCF$_3$, —OCH$_2$CF$_3$, —OCH$_3$ or —OCH$_2$CH$_3$. In some embodiments, $R^A$ is H, F, Cl, —CH$_3$, —CF$_3$, —OCF$_3$, or —OCH$_3$. In some embodiments, $R^A$ is H, Cl, or —OCH$_3$. In some embodiments, $R^A$ is H.

In some embodiments, $R^B$ is H, F, Cl, Br, —CN, —OH, —CH$_3$, —CF$_3$, —OCF$_3$, —OCH$_2$CF$_3$, —OCH$_3$ or —OCH$_2$CH$_3$. In some embodiments, $R^B$ is H, F, Cl, —CH$_3$, —CF$_3$, —OCF$_3$, or —OCH$_3$. In some embodiments, $R^B$ is H, Cl, or —OCH$_3$. In some embodiments, $R^B$ is H.

In some embodiments, $R^A$ is H, halogen, —CN, —OH, $C_1$-$C_4$alkyl, $C_1$-$C_4$fluoroalkyl, $C_1$-$C_4$fluoroalkoxy, or $C_1$-$C_4$alkoxy; and $R^B$ is H. In some embodiments, $R^A$ is H; and $R^B$ is H, halogen, —CN, —OH, $C_1$-$C_4$alkyl, $C_1$-$C_4$fluoroalkyl, $C_1$-$C_4$fluoroalkoxy, or $C_1$-$C_4$alkoxy.

In some embodiments, $R^A$ is H; and $R^B$ is H.

In some embodiments, $R^A$ is selected from H, F, Cl, Br, —CN, —OH, —CH$_3$, —CF$_3$, —OCF$_3$, —OCH$_2$CF$_3$, —OCH$_3$ and —OCH$_2$CH$_3$; $R^B$ is selected from H, F, Cl, Br, —CN, —OH, —CH$_3$, —CF$_3$, —OCF$_3$, —OCH$_2$CF$_3$, —OCH$_3$ and —OCH$_2$CH$_3$; $R^6$ is H, F, Cl, Br, —CN, —OH, —$SR^{13}$, —S(=O)$R^{12}$, —S(=O)$_2R^{12}$, —NHS(=O)$_2R^{12}$, —CO$_2R^{13}$, —C(=O)NH($R^{13}$), —NHC(=O)$R^{12}$, —CH$_3$, —CF$_3$, —OCF$_3$, or —OCH$_3$; $R^{12}$ is $C_1$-$C_4$alkyl; $R^{13}$ is H or $C_1$-$C_4$alkyl.

In some embodiments, $R^6$ is H, F, Cl, Br, —CN, —OH, —$SR^{13}$, —S(=O)$R^{12}$, —S(=O)$_2R^{12}$, —NHS(=O)$_2R^{12}$, —CO$_2R^{13}$, —C(=O)NH($R^{13}$), —NHC(=O)$R^{12}$, —CH$_3$, —CF$_3$, —OCF$_3$, or —OCH$_3$. In some embodiments, $R^6$ is F, Cl, Br, —CN, —OH, —$SR^{13}$, —S(=O)$R^{12}$, S(=O)$_2R^{12}$, —NHS(=O)$_2R^{12}$, —CO$_2R^{13}$, —C(=O)NH($R^{13}$), —NHC(=O)$R^{12}$, —CH$_3$, —CF$_3$, —OCF$_3$, or —OCH$_3$. In some embodiments, $R^6$ is F, Cl, —CN, —OH, —$SR^{13}$, —S(=O)$R^{12}$, —S(=O)$_2R^{12}$, —CO$_2R^{13}$, —CH$_3$, —CF$_3$, —OCF$_3$, or —OCH$_3$. In some embodiments, $R^6$ is F, Cl, —CN, —OH, —$SR^{13}$, —CO$_2R^{13}$, —CH$_3$, —CF$_3$, —OCF$_3$, or —OCH$_3$. In some embodiments, $R^6$ is F, Cl, —CH$_3$, —CF$_3$, —OCF$_3$, or —OCH$_3$. In some embodiments, $R^6$ is —CF$_3$.

In some embodiments, $R^{12}$ is $C_1$-$C_4$alkyl. In some embodiments, $R^{12}$ is —CH$_3$, —CH$_2$CH$_3$, —CH(CH$_3$)$_2$, or —C(CH$_3$)$_3$. In some embodiments, $R^{13}$ is H, $C_1$-$C_4$alkyl or substituted or unsusbtituted benzyl. In some embodiments, $R^{13}$ is H or $C_1$-$C_4$alkyl. In some embodiments, $R^{13}$ is H, —CH$_3$, —CH$_2$CH$_3$, —CH(CH$_3$)$_2$, or —C(CH$_3$)$_3$. In some embodiments, $R^{13}$ is H. In some embodiments, $R^{13}$ is a substituted or unsusbtituted benzyl.

In some embodiments, $R^{10}$ is $C_1$-$C_4$alkyl, $C_3$-$C_6$cycloalkyl, —$C_1$-$C_2$alkyl-(substituted or unsubstituted phenyl), —$C_1$-$C_2$alkyl-(substituted or unsubstituted 6-membered heteroaryl containing 1 or 2 N atom), —$C_1$-$C_2$alkyl-O—$C_1$-$C_4$alkyl, —O—$C_1$-$C_4$alkyl, —O—$C_1$-$C_2$alkyl-(substituted or unsubstituted phenyl), —$NR^{16}C_1$-$C_4$alkyl, or —$NR^{16}C_1$-$C_2$alkyl-(substituted or unsubstituted phenyl); $R^{11}$ is $C_1$-$C_4$alkyl, $C_3$-$C_6$cycloalkyl or substituted or unsubstituted benzyl.

In some embodiments, $R^{10}$ is $C_1$-$C_4$alkyl, $C_3$-$C_6$cycloalkyl, —$C_1$-$C_2$alkyl-(substituted or unsubstituted phenyl), —$C_1$-$C_2$alkyl-(substituted or unsubstituted 6-membered heteroaryl containing 1 or 2 N atom), —$C_1$-$C_2$alkyl-O—$C_1$-$C_4$alkyl, —O—$C_1$-$C_4$alkyl, —O—$C_1$-$C_2$alkyl-(substituted or unsubstituted phenyl), —$NR^{16}C_1$-$C_4$alkyl, or —$NR^{16}C_1$-$C_2$alkyl-(substituted or unsubstituted phenyl); $R^{11}$ is $C_1$-$C_4$alkyl or $C_3$-$C_6$cycloalkyl.

In some embodiments, $R^{10}$ is —CH$_3$, —CH$_2$CH$_3$, —CH(CH$_3$)$_2$, —C(CH$_3$)$_3$, cyclopropyl, cyclobutyl, cyclopentyl, cyclohexyl, —CH$_2$OCH$_3$, —CH$_2$OCH$_2$CH$_3$, —$C_1$-$C_2$alkyl-(substituted or unsubstituted phenyl), —$C_1$-$C_2$alkyl-(substituted or unsubstituted 6-membered heteroaryl containing 1 or 2 N atom); where each substituted phenyl or substituted heteroaryl is substituted with 1 or 2 $R^C$, where each $R^C$ is independently selected from halogen, —OH, —CH$_3$, —CH$_2$CH$_3$, —OCH$_3$, —OCH$_2$CH$_3$, and —CF$_3$. In some embodiments, $R^{10}$ is —CH$_3$, —CH$_2$CH$_3$, cyclopropyl, —CH$_2$OCH$_3$, —CH$_2$OCH$_2$CH$_3$, —$C_1$-$C_2$alkyl-(substituted or unsubstituted phenyl), —$C_1$-$C_2$alkyl-(substituted or unsubstituted 6-membered heteroaryl containing 1 or 2 N atom).

In some embodiments, $R^{11}$ is —CH$_3$, —CH$_2$CH$_3$, or cyclopropyl.

In some embodiments, $R^B$ is H; $R^6$ is F, Cl, Br, —CH$_3$, —CF$_3$, —OCF$_3$, or —OCH$_3$; $R^{10}$ is —CH$_3$, cyclopropyl, —CH$_2$OCH$_3$, or —CH$_2$OCH$_2$CH$_3$; $R^H$ is —CH$_2$CH$_3$.

In some embodiments, $R^B$ is H; $R^6$ is F, Cl, Br, —CH$_3$, —CF$_3$, —OCF$_3$, or —OCH$_3$; $R^{10}$ is —CH$_3$, cyclopropyl, —CH$_2$OCH$_3$, or —CH$_2$OCH$_2$CH$_3$. In some embodiments, $R^B$ is H; $R^H$ is —CH$_2$CH$_3$.

In some embodiments, $R^{10}$ is C$_1$-C$_4$alkyl, or C$_3$-C$_6$cycloalkyl; $R^{11}$ is substituted or unsubstituted benzyl. In some embodiments, $R^{10}$ is C$_1$-C$_4$alkyl, or cyclopropyl; $R^{11}$ is substituted or unsubstituted benzyl.

In some embodiments, $R^B$ is H; $R^6$ is F, Cl, Br, —CH$_3$, —CF$_3$, —OCF$_3$, or —OCH$_3$; $R^{10}$ is —CH$_3$, or cyclopropyl; $R^{11}$ is substituted or unsubstituted benzyl.

In some embodiments, $R^{10}$ is —O—C$_1$-C$_4$alkyl or —O—C$_1$-C$_2$alkyl-(substituted or unsubstituted phenyl). In some embodiments, $R^{10}$ is —O—C$_1$-C$_2$alkyl-(substituted or unsubstituted phenyl). In some embodiments, $R^{10}$ is —O—CH$_2$-(substituted or unsubstituted phenyl).

In some embodiments, $R^{10}$ is —O—CH$_2$-(substituted or unsubstituted phenyl) or —O—CH(CH$_3$)-(substituted or unsubstituted phenyl); where each substituted phenyl is substituted with 1 or 2 $R^C$, where each $R^C$ is independently selected from halogen, —OH, —CH$_3$, —CH$_2$CH$_3$, —OCH$_3$, —OCH$_2$CH$_3$, and —CF$_3$; $R^{11}$ is C$_1$-C$_4$alkyl or C$_3$-C$_6$cycloalkyl.

In some embodiments, $R^B$ is H; $R^6$ is F, Cl, Br, —CH$_3$, —CF$_3$, —OCF$_3$, or —OCH$_3$; $R^{10}$ is —O—CH$_2$-(substituted or unsubstituted phenyl), where the substituted phenyl is substituted with 1 or 2 $R^C$, where each $R^C$ is independently selected from F, Cl, Br, —OH, —CH$_3$, —OCH$_3$, and —CF$_3$; $R^H$ is C$_1$-C$_4$alkyl.

In some embodiments, $R^A$ is selected from H, F, Cl, —CH$_3$, —CF$_3$, —OCF$_3$, and —OCH$_3$; $R^6$ is —CF$_3$; $R^{10}$ is —O—CH$_2$-(substituted or unsubstituted phenyl), where the substituted phenyl is substituted with 1 or 2 $R^C$, where each $R^C$ is independently selected from F, Cl, Br, —OH, —CH$_3$, —OCH$_3$, and —CF$_3$; $R^{11}$ is —CH$_2$CH$_3$.

In some embodiments, $R^{10}$ is —NR$^{16}$C$_1$-C$_4$alkyl, or —NR$^{16}$C$_1$-C$_2$alkyl-(substituted or unsubstituted phenyl); $R^{16}$ is H, —CH$_3$ or —CH$_2$CH$_3$. In some embodiments, $R^{16}$ is H.

In some embodiments, $R^{10}$ is —NR$^{16}$—CH$_2$-(substituted or unsubstituted phenyl) or —NR$^{16}$—CH(CH$_3$)-(substituted or unsubstituted phenyl), where the substituted phenyl is substituted with 1 or 2 $R^C$ groups, where each $R^C$ is independently selected from F, Cl, Br, —OH, —CH$_3$, —OCH$_3$, and —CF$_3$; $R^{11}$ is C$_1$-C$_4$alkyl or C$_3$-C$_6$cycloalkyl; $R^{16}$ is H, —CH$_3$ or —CH$_2$CH$_3$. In some embodiments, $R^{10}$ is —NR$^{16}$C$_1$-C$_2$alkyl-(substituted or unsubstituted phenyl). In some embodiments, $R^{10}$ is —NR$^{16}$—CH$_2$-(substituted or unsubstituted phenyl).

In some embodiments, $R^B$ is H; $R^6$ is F, Cl, Br, —CH$_3$, —CF$_3$, —OCF$_3$, or —OCH$_3$; $R^{10}$ is —NR$^{16}$—CH$_2$-(substituted or unsubstituted phenyl); where the substituted phenyl is substituted with 1 or 2 $R^C$ groups, where each $R^C$ is independently selected from F, Cl, Br, —OH, —CH$_3$, —OCH$_3$, and —CF$_3$; $R^{11}$ is C$_1$-C$_4$alkyl.

In some embodiments, $R^A$ is selected from H, F, Cl, —CH$_3$, —CF$_3$, —OCF$_3$, and —OCH$_3$; $R^6$ is —CF$_3$; $R^{10}$ is —NR$^{16}$—CH$_2$-(substituted or unsubstituted phenyl); where the substituted phenyl is substituted with 1 or 2 $R^C$ groups, where each $R^C$ is independently selected from F, Cl, Br, —OH, —CH$_3$, —OCH$_3$, and —CF$_3$; $R^{11}$ is —CH$_2$CH$_3$.

In some embodiments, $R^{10}$ is C$_1$-C$_4$alkyl, C$_1$-C$_4$fluoroalkyl, C$_3$-C$_6$cycloalkyl, —C$_1$-C$_2$alkyl-(substituted or unsubstituted phenyl), —C$_1$-C$_2$alkyl-(substituted or unsubstituted 6-membered heteroaryl containing 1 or 2 N atom), —C$_1$-C$_2$alkyl-O—C$_1$-C$_4$alkyl, —O—C$_1$-C$_4$alkyl, —O—C$_1$-C$_2$alkyl-(substituted or unsubstituted phenyl), —NR$^{16}$C$_1$-C$_4$alkyl, or —NR$^{16}$C$_1$-C$_2$alkyl-(substituted or unsubstituted phenyl).

In some embodiments, $R^{10}$ is C$_1$-C$_4$alkyl, C$_1$-C$_4$fluoroalkyl, C$_3$-C$_6$cycloalkyl, —C$_1$-C$_2$alkyl-(substituted or unsubstituted phenyl), —C$_1$-C$_2$alkyl-(substituted or unsubstituted 6-membered heteroaryl containing 1 or 2 N atom), or —C$_1$-C$_2$alkyl-O—C$_1$-C$_4$alkyl.

In some embodiments, $R^{10}$ is C$_1$-C$_4$alkyl, C$_3$-C$_6$cycloalkyl, —CH$_2$-(substituted or unsubstituted phenyl), —CH$_2$-(substituted or unsubstituted 6-membered heteroaryl containing 1 or 2 N atom), or —C$_1$-C$_2$alkyl-O—C$_1$-C$_4$alkyl. In some embodiments, $R^{10}$ is C$_1$-C$_4$alkyl, C$_3$-C$_6$cycloalkyl, or —C$_1$-C$_2$alkyl-O—C$_1$-C$_4$alkyl. In some embodiments, $R^{10}$ is —CH$_3$ or cyclopropyl.

In some embodiments, $R^{11}$ is C$_1$-C$_4$alkyl, C$_3$-C$_6$cycloalkyl, or substituted or unsubstituted benzyl. In some embodiments, $R^{11}$ is C$_1$-C$_4$alkyl, or substituted or unsubstituted benzyl. In some embodiments, $R^{11}$ is C$_1$-C$_4$alkyl or C$_1$-C$_4$haloalkyl. In some embodiments, $R^{11}$ is C$_1$-C$_4$alkyl. In some embodiments, $R^{11}$ is —CH$_2$CH$_3$. In some embodiments, $R^{11}$ is —CH$_3$, —CH$_2$CH$_3$, —CF$_3$, —CH$_2$CF$_3$, cyclopropyl, cyclobutyl, or cyclopentyl. In some embodiments, $R^{11}$ is —CH$_2$CH$_3$, —CH$_2$CF$_3$, or cyclopropyl. In some embodiments, $R^{11}$ is —CH$_3$, —CH$_2$CH$_3$, or cyclopropyl. In some embodiments, $R^{11}$ is —CH$_2$CH$_3$, or —CH$_2$CF$_3$. In some embodiments, $R^{11}$ is C$_3$-C$_6$cycloalkyl. In some embodiments, $R^{11}$ is cyclopropyl. In some embodiments, $R^{11}$ is substituted or unsubstituted benzyl.

In some embodiments, the compound of Formula (I) has the following structure:

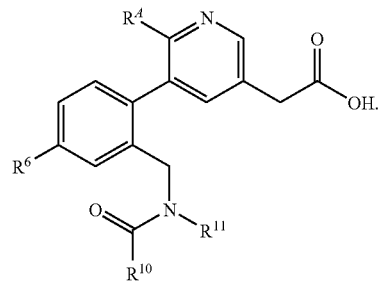

In some embodiments, the compound of Formula (I) is an N-oxide.

In one aspect are 2-{5-[2-(N—(R$^{11}$)—N—((R$^{10}$)carbonyl)aminomethyl)-4-(R$^6$)-phenyl]-6-(R$^A$)-2-(R$^B$)-pyridin-3-yl}acetic acid compounds.

In some embodiments, $R^6$ is as defined in Table 1. In some embodiments, $R^{11}$ is as defined in Table 1. In some embodiments, $R^{10}$ is as defined in Table 1. In some embodiments, $R^A$ is as defined in Table 1. In some embodiments, $R^B$ is as defined in Table 1.

Any combination of the groups described above for the various variables is contemplated herein. Throughout the specification, groups and substituents thereof are chosen by one skilled in the field to provide stable moieties and compounds.

Compounds of Formula (I) include, but are not limited to, those described in Table 1:

TABLE 1

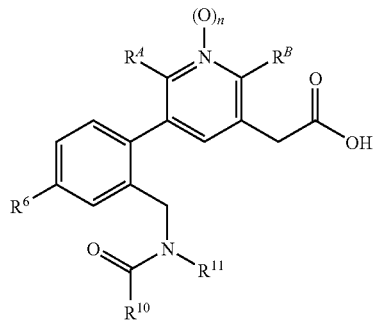

| Cpmd # | $R^A$ | $R^B$ | n | $R^6$ | $R^{11}$ | $R^{10}$ | M + H* |
|---|---|---|---|---|---|---|---|
| 1 | H | H | 0 | $CO_2H$ | $CH_2CH_3$ | —C(=O)—$OCH_2$phenyl | 449 |
| 2 | H | H | 0 | $CO_2H$ | $CH_2CH_3$ | —C(=O)-cyclopropyl | 383 |
| 3 | H | H | 0 | CN | Benzyl | —C(=O)-cyclopropyl | 426 |
| 4 | H | H | 0 | 2H-Tetrazol-5-yl | Benzyl | —C(=O)-cyclopropyl | 469 |
| 5 | H | H | 0 | Benzylcarbamoyl | Benzyl | —C(=O)-cyclopropyl | 534 |
| 6 | H | H | 0 | Methylcarbamoyl | Benzyl | —C(=O)-cyclopropyl | 458 |
| 7 | H | H | 0 | tert-Butylcarbamoyl | Benzyl | —C(=O)-cyclopropyl | 500 |
| 8 | H | H | 0 | $CF_3$ | $CH_2CH_3$ | —C(=O)-cyclopropyl | 407 |
| 9 | H | Cl | 0 | $CF_3$ | $CH_2CH_3$ | —C(=O)-cyclopropyl | 441 |
| 10 | $OCH_3$ | H | 0 | $CF_3$ | $CH_2CH_3$ | —C(=O)-cyclopropyl | 437 |
| 11 | Cl | H | 0 | $CF_3$ | $CH_2CH_3$ | —C(=O)-cyclopropyl | 441 |
| 12 | H | H | 0 | $CF_3$ | $CH_2CH_3$ | —C(=O)-$OCH_2$phenyl | 473 |
| 13 | H | H | 0 | $CF_3$ | $CH_2CH_3$ | tert-Butoxycarbonyl | 439 |
| 14 | H | H | 0 | $CF_3$ | $CH_2CH_3$ | C(O)NH-Benzyl | 472 |
| 15 | H | H | 1 | $CF_3$ | $CH_2CH_3$ | —C(=O)-$OCH_2$phenyl | 489 |
| 16 | H | H | 0 | $CF_3$ | $CH_2CH_3$ | —C(=O)$CH_2$-(phenyl) | 457 |
| 17 | H | H | 0 | $CF_3$ | Benzyl | —C(=O)-cyclopropyl | 469 |
| 18 | H | H | 0 | $CF_3$ | Benzyl | —C(=O)$CH_3$ | 443 |
| 19 | Cl | H | 0 | $CF_3$ | Benzyl | —C(=O)$CH_3$ | 477 |
| 20 | H | Cl | 0 | $CF_3$ | Benzyl | —C(=O)$CH_3$ | 477 |
| 21 | H | H | 0 | $SCH_3$ | $CH_2CH_3$ | —C(=O)-cyclopropyl | 385 |
| 22 | H | H | 0 | 4-tert-Butylsulfanyl | $CH_2CH_3$ | —C(=O)-cyclopropyl | 427 |
| 23 | H | H | 0 | F | $CH_2CH_3$ | —C(=O)-cyclopropyl | 357 |
| 24 | H | H | 0 | SH | $CH_2CH_3$ | —C(=O)-cyclopropyl | |
| 25 | H | H | 0 | $CF_3$ | $CH_2CH_3$ | —C(=O)$CH_2CH_2$-(phenyl) | 471 |
| 26 | OH | H | 0 | $CF_3$ | Benzyl | —C(=O)$CH_3$ | 459 |
| 27 | $OCH_3$ | H | 0 | $CF_3$ | $CH_2CH_3$ | C(O)NH-Benzyl | 502 |
| 28 | $OCH_3$ | H | 0 | $CF_3$ | Benzyl | —C(=O)$CH_3$ | 473 |
| 29 | H | H | 0 | $CF_3$ | $CH_2CH_3$ | —C(=O)-(pyrazin-2-yl) | 445 |
| 30 | H | H | 0 | $CF_3$ | $CH_2CH_3$ | —C(=O)-(2,4-dimethoxy-pyrimidin-5-yl) | 505 |
| 31 | H | H | 0 | $CF_3$ | $CH_2CH_3$ | —C(=O)$CH_2$-(6-chloro-pyridin-3-yl) | 492 |
| 32 | H | H | 0 | $CF_3$ | $CH_2CH_3$ | —C(=O)$CH_2$-(4,6-diethoxy-pyrimidin-2-yl) | 547 |
| 33 | H | H | 0 | $CF_3$ | $CH_2CH_3$ | —C(=O)$CH_2$-(pyridin-2-yl) | 458 |
| 34 | H | H | 0 | $CF_3$ | $CH_2CH_3$ | —C(=O)$CH_2OCH_3$ | 411 |
| 35 | H | H | 0 | $CF_3$ | $CH_2CH_3$ | —C(=O)$CH_2OCH_2CH_3$ | 425 |
| 36 | H | H | 0 | $CF_3$ | $CH_2CH_3$ | —C(=O)$CH_2CH_2$-(pyridin-3-yl) | 472 |
| 37 | H | H | 0 | $CF_3$ | $CH_2CH_3$ | —C(=O)$CH_2$-(6-Methyl-pyridin-3-yl) | 472 |
| 38 | OH | H | 0 | $CF_3$ | $CH_2CH_3$ | —C(=O)-cyclopropyl | 423 |
| 39 | $OCH_2CF_3$ | H | 0 | $CF_3$ | $CH_2CH_3$ | —C(=O)-cyclopropyl | 505 |
| 40 | $OCH_3$ | H | 0 | $CF_3$ | $CH_2CH_3$ | —C(=O)—$OCH_2$phenyl | 503 |
| 41 | $OCH_3$ | H | 0 | $CF_3$ | $CH_2CH_3$ | —C(=O)$CH_3$ | 411 |
| 42 | $OCH_3$ | H | 0 | $CF_3$ | $CH_2CH_3$ | —C(=O)—$CH_2OCH_3$ | 441 |
| 43 | $OCH_3$ | H | 0 | $CF_3$ | $CH_2CH_3$ | —C(=O)—$OCH_2CH_3$ | 441 |

*mass spectrometric data

Further Forms of Compounds

In certain embodiments, compounds of Formula (I) are prepared as pharmaceutically acceptable salts by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, p-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, and muconic acid.

Pharmaceutically acceptable salts are also obtained by reacting a compound of Formula (I) with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts with amino acids such as arginine, lysine, and the like.

In other embodiments, compounds of Formula (I) are prepared as a pharmaceutically acceptable salts by reacting the free acid form of the compound with a pharmaceutically acceptable inorganic or organic base, including, but not limited to organic bases such as ethanolamine, diethanolamine, triethanolamine, tromethamine, N-methylglucamine, and the like, or with an inorganic base such as aluminum hydroxide, calcium hydroxide, potassium hydroxide, sodium carbonate, sodium hydroxide, and the like.

Reference to a pharmaceutically acceptable salt includes the solvent addition forms or crystal forms thereof, particularly solvates or polymorphs. Solvates contain either stoichiometric or non-stoichiometric amounts of a solvent, and are optionally formed during the process of crystallization with pharmaceutically acceptable solvents such as water, ethanol, and the like. Hydrates are formed when the solvent is water, and alcoholates are formed when the solvent is alcohol. Solvates of compounds of Formula (I) are conveniently prepared or formed during the processes described herein. By way of example only, hydrates of compounds of Formula (I) are conveniently prepared by recrystallization from an aqueous/organic solvent mixture, using organic solvents including, but not limited to, dioxane, tetrahydrofuran, ethanol, or methanol. In addition, the compounds provided herein can exist in unsolvated as well as solvated forms. In general, the solvated forms are considered equivalent to the unsolvated forms for the purposes of the compounds and methods provided herein.

In some embodiments, compounds of Formula (I) are prepared as prodrugs. A "prodrug" refers to an agent that is converted into the parent drug in vivo.

In yet another embodiment, the compounds of Formula (I) possess one or more stereocenters and each center exists independently in either the R or S configuration. The compounds presented herein include all diastereomeric, enantiomeric, and epimeric forms as well as the appropriate mixtures thereof Stereoisomers are obtained, if desired, by methods such as, the separation of stereoisomers by chiral chromatographic columns or stereoselective synthesis.

The methods and formulations described herein include the use of N-oxides (if appropriate), crystalline forms (also known as polymorphs), or pharmaceutically acceptable salts of compounds having the structure of Formula (I), as well as active metabolites of these compounds having the same type of activity. In some situations, compounds exist as tautomers.

In some embodiments, the compounds described herein exist as tautomers. All tautomers are intended to be within the scope of the molecular formulas described herein.

In some embodiments, compounds described herein are isotopically-labeled, which are identical to those recited in the various formulae and structures presented herein, but for the fact that one or more atoms are replaced by an atom having an atomic mass or mass number different from the atomic mass or mass number usually found in nature. In some embodiments, one or more hydrogen atoms are replaced with deuterium. In some embodiments, metabolic sites on the compounds described herein are deuterated. In some embodiments, substitution with deuterium affords certain therapeutic advantages resulting from greater metabolic stability, such as, for example, increased in vivo half-life or reduced dosage requirements.

Compounds of Formula (I) are $DP_2$ antagonists. In one aspect, compounds of Formula (I) are used in the treatment of $PGD_2$-dependent or $PGD_2$-mediated diseases, disorders or conditions as disclosed herein. In one aspect, the compounds of Formula (I) show selectivity for $DP_2$ versus other receptors, such as for example DP, CETP and/or PPAR receptors. In one aspect, the compounds of Formula (I) show high affinity for $DP_2$ versus other receptors, such as for example DP, CETP and/or PPAR receptors.

DEFINITIONS

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. In this application, the use of "or" or "and" means "and/or" unless stated otherwise. Furthermore, use of the term "including" as well as other forms, such as "include", "includes," and "included," is not limiting.

"Alkoxy" refers to (alkyl)O—, where alkyl is as defined herein.

"Alkyl" refers to an aliphatic hydrocarbon group. The alkyl may be saturated or unsaturated. In one aspect, alkyl groups are selected from methyl, ethyl, propyl, iso-propyl, n-butyl, iso-butyl, sec-butyl, and t-butyl.

"Cycloalkyl" refers to a monocyclic aliphatic, non-aromatic radical, wherein each of the atoms forming the ring (i.e. skeletal atoms) is a carbon atom. Cycloalkyl groups include, for example, cyclopropyl, cyclobutyl, cyclopentyl, and cyclohexyl.

"Halo", "halogen" or "halide" means fluoro, chloro, bromo or iodo.

"Fluoroalkyl" refers to an alkyl in which one or more hydrogen atoms are replaced by a fluorine atom. In one aspect, a fluoroalkyl is selected from —$CF_3$, —$CHF_2$, —$CH_2F$, —$CH_2CF_3$ and —$CF_2CF_3$.

"Fluoroalkoxy" refers to (fluoroalkyl)O—, where fluoroalkyl is as defined herein.

"Heteroalkyl" refers to an alkyl group in which one or more skeletal atoms of the alkyl are selected from an atom other than carbon, e.g., oxygen, nitrogen, sulfur, phosphorus or combinations thereof. In one aspect, heteroalkyl refers to an alkyl group in which one of the skeletal atoms of the alkyl is oxygen, nitrogen, or sulfur. In another aspect, heteroalkyl refers to an alkyl group in which one of the skeletal atoms of the alkyl is oxygen.

"6-Membered heteroaryl" includes pyridinyl, pyridazinyl, pyrimidinyl, pyrazinyl and triazinyl.

The term "optionally substituted" or "substituted" means that the referenced group may be substituted with one or more additional group(s) individually and independently selected from halogen, —OH, —CN, $C_1$-$C_4$alkyl, $C_1$-$C_4$fluoroalkyl, $C_1$-$C_4$alkoxy, $C_1$-$C_4$fluoroalkoxy, —$NH_2$, —$NH(C_1$-$C_4$alkyl), —$N(C_1$-$C_4$alkyl$)_2$, and $C_1$-$C_4$heteroalkyl. In some cases, the referenced substituted group is substituted with 1 or 2 of the aforementioned groups. For example, in some embodiments, a referenced substituted group is substituted with at least one group selected from halogen, —OH, —CN, —$CH_3$, —$CH_2CH_3$, —$CF_3$, —$OCH_3$, —$OCH_2CH_3$, and —$OCF_3$.

A "metabolite" of a compound disclosed herein is a derivative of that compound that is formed when the compound is metabolized. The term "active metabolite" refers to a biologically active derivative of a compound that is formed when the compound is metabolized.

"$PGD_2$-dependent" refers to conditions or disorders that would not occur, or would not occur to the same extent, in the absence of $PGD_2$. "$PGD_2$-mediated" refers to refers to conditions or disorders that might occur in the absence of $PGD_2$ but can occur in the presence of $PGD_2$.

"Effective amount" or "therapeutically effective amount," as used herein, refer to a sufficient amount of an agent or a compound being administered which will relieve to some extent one or more of the symptoms of the disease or condition being treated. An appropriate effective amount in any individual case may be determined using techniques, such as a dose escalation study.

The terms "treat," "treating" or "treatment," as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

The term "subject" or "patient" encompasses mammals and non-mammals. In one aspect, the "subject" or "patient" is a mammal. In one embodiment, the mammal is a human.

Pharmaceutical Composition/Formulation

Suitable routes of administration include, but are not limited to, oral, intravenous, rectal, aerosol, parenteral, ophthalmic, pulmonary, transmucosal, transdermal, vaginal, otic, nasal, intramuscular injection, subcutaneous injection, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound as described herein is administered in a local rather than systemic manner. In other embodiments, the compound as described herein is provided in the form of a rapid release formulation, in the form of an extended release formulation, or in the form of an intermediate release formulation. In yet other embodiments, the compound described herein is administered topically.

In some embodiments, the compounds described herein are formulated into pharmaceutical compositions. In specific embodiments, pharmaceutical compositions are formulated in a conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are used as suitable to formulate the pharmaceutical compositions described herein: *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999).

A pharmaceutical composition refers to a mixture of a compound of Formula (I) with other chemical components, such as carriers, stabilizers, diluents, dispersing agents, suspending agents, thickening agents, and/or excipients. In certain embodiments, the pharmaceutical composition facilitates administration of the compound to a mammal.

In some embodiments, compounds described herein are formulated for oral administration. The compounds described herein are formulated in oral dosage forms that include, by way of example only, tablets, powders, pills, dragees, capsules, liquids, gels, syrups, elixirs, slurries, suspensions and the like.

In one embodiment, compounds of Formula (I) are formulated in an aqueous solution. In specific embodiments, the aqueous solution is selected from, by way of example only, a physiologically compatible buffer, such as Hank's solution, Ringer's solution, or physiological saline buffer.

In other embodiments, compounds of Formula (I) are formulated for transmucosal administration. In specific embodiments, transmucosal formulations include penetrants that are appropriate to the barrier to be permeated.

In still other embodiments wherein the compounds described herein are formulated for other parenteral injections, appropriate formulations include aqueous or nonaqueous solutions.

In certain embodiments, pharmaceutical preparations for oral use are obtained by mixing one or more solid excipient with one or more of the compounds described herein, optionally grinding the resulting mixture, and processing the mixture of granules, after adding suitable auxiliaries, if desired, to obtain tablets or pills. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. In specific embodiments, disintegrating agents are optionally added. Disintegrating agents include, by way of example only, cross-linked croscarmellose sodium, polyvinylpyrrolidone, agar, or alginic acid or a salt thereof such as sodium alginate.

Oral dosage forms also include push-fit capsules made of gelatin, as well as soft, sealed capsules made of gelatin and a plasticizer, such as glycerol or sorbitol. In specific embodiments, push-fit capsules contain the active ingredients in admixture with one or more filler. Fillers include, by way of example only, lactose, binders such as starches, and/or lubricants such as talc or magnesium stearate and, optionally, stabilizers. In other embodiments, soft capsules contain one or more active compound that is dissolved or suspended in a suitable liquid. Suitable liquids include, by way of example only, one or more fatty oil, liquid paraffin, or liquid polyethylene glycol. In addition, stabilizers are optionally added.

In still other embodiments, the compounds of Formula (I) are administered topically. Topically administrable compositions include solutions, suspensions, lotions, gels, pastes, medicated sticks, balms, creams or ointments.

In other embodiments, the compounds of Formula (I) are formulated for administration by inhalation. Various forms suitable for administration by inhalation include, but are not limited to, aerosols, mists or powders.

The active ingredient in the pharmaceutical compositions is in free-acid or free-base form, or in a pharmaceutically acceptable salt form. In addition, the methods and pharmaceutical compositions described herein include the use of N-oxides, crystalline forms (also known as polymorphs), as well as active metabolites of these compounds having the same type of activity. All tautomers of the compounds described herein are included within the scope of the compounds presented herein. Additionally, the compounds described herein encompass unsolvated as well as solvated forms with pharmaceutically acceptable solvents such as water, ethanol, and the like. The solvated forms of the compounds presented herein are also considered to be disclosed herein. In addition, the pharmaceutical compositions optionally include other medicinal or pharmaceutical agents, carriers, adjuvants, such as preserving, stabilizing, wetting or emulsifying agents, solution promoters, salts for regulating the osmotic pressure, buffers, and/or other therapeutically valuable substances.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation clinical trial.

In prophylactic applications, compositions comprising the compounds described herein are administered to a patient susceptible to or otherwise at risk of a particular disease, disorder or condition. In this use, the precise amounts also depend on the patient's state of health, weight, and the like.

The amount of a given agent that corresponds to such an amount varies depending upon factors such as the particular compound, disease or condition and its severity, the identity (e.g., weight) of the mammal in need of treatment, but can nevertheless be determined according to the particular circumstances surrounding the case, including, e.g., the specific agent being administered, the route of administration, the condition being treated, and the mammal being treated. Doses employed for adult human treatment are typically in the range of 0.02-5000 mg per day, 0.5-1500 mg per day, or 1-500 mg per day. In one embodiment, the dose is presented in a single dose or in divided doses administered at appropriate intervals, for example as two, three, four or more sub-doses per day.

In one embodiment, the daily dosages appropriate for the compound of Formula (I) are from about 0.01 to about 10 mg/kg per body weight. In certain embodiments, suitable unit dosage forms for oral administration comprise from about 1 to 500 mg active ingredient. In other embodiments, the daily dosage or the amount of active in the dosage form are lower or higher than the ranges indicated herein.

In certain instances, it is appropriate to administer at least one compound of Formula (I) in combination with another therapeutic agent. In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills).

In some embodiments, compounds of Formula (I) are administered chronically. In some embodiments, compounds of Formula (I) are administered intermittently (e.g. drug holiday that includes a period of time in which the compound is not administered or is administered in a reduced amount). In some embodiments, compounds of Formula (I) are administered in cycles that include: (a) a first period that includes daily administration of the compound of Formula (I); followed by (b) a second period that includes a dose reduction of the daily amount of compound of Formula (I) that is administered. In some embodiments, the compound of Formula (I) is not administered in the second period. In some embodiments, the duration of the first and second periods, as well as the dose amounts are determined using methods described herein or known in the art.

EXAMPLES

These examples are provided for illustrative purposes only and not to limit the scope of the claims provided herein.

Example 1

Synthesis of 3-[(N-Benzyloxycarbonyl-N-ethyl-amino)-methyl]-4-(5-carboxymethyl-pyridin-3-yl)-benzoic acid (Compound 1)

Step 1: 5-Bromo-3-pyridylacetic acid was treated with 5% concentrated sulfuric acid in EtOH at reflux overnight to give (5-bromo-pyridin-3-yl)-acetic acid ethyl ester.

Step 2: To 4-bromo-3-methylbenzoic acid (16.27 g, 75.7 mmol) in EtOH (500 mL) was added concentrated sulfuric acid (0.5 mL), and the reaction was stirred at 95° C. overnight. Additional sulfuric acid (2 mL) was added to push the reaction to completion, and then the mixture was quenched with the slow addition of sodium carbonate. The mixture was filtered and concentrated, and the residue was diluted and washed with $H_2O$ twice, saturated aqueous $NaHCO_3$, brine, and $H_2O$ to give 4-bromo-3-methyl-benzoic acid ethyl ester.

Step 3: 4-Bromo-3-methyl-benzoic acid ethyl ester (18.24 g, 75.4 mmol), N-bromosuccinimide (14.1 g, 79.2 mmol), and benzoyl peroxide (0.9 g, 3.77 mmol) were combined in $CCl_4$, and the reaction was heated to 80° C. and stirred with a halogen desk lamp shining on it for 6 hours. The mixture was concentrated and partitioned between $CH_2Cl_2$ and $H_2O$. The organic layer was separated and washed with $H_2O$ and brine, and then dried and concentrated. The residue was triturated with hexane (3×50 mL) and dried to give 4-bromo-3-bromomethyl-benzoic acid ethyl ester.

Step 4: Ethylamine (1.3 mL, 20.0 mmol) and diisopropylethylamine (7 mL, 40.0 mmol) were combined in $CH_2Cl_2$ (200 mL) and cooled to 0° C. Benzyl chloroformate (2.86 mL, 20.0 mmol) was added dropwise, and the reaction was stirred at 0° C. for 30 minutes. The mixture was warmed to room temperature and washed with $H_2O$, 0.1N aqueous HCl, and $H_2O$, and then dried and concentrated to give ethyl-carbamic acid benzyl ester.

Step 5: 4-Bromo-3-bromomethyl-benzoic acid ethyl ester (2.95 g, 9.2 mmol) and ethyl-carbamic acid benzyl ester (3.30 g, 18.4 mmol) were combined in DMF (100 mL) and cooled to 0° C. Sodium hydride (60% in mineral oil; 0.772 g, 19.3 mmol) was added slowly, and the reaction was stirred at room temperature for 10 minutes. The mixture was quenched with $H_2O$ and 1N aqueous HCl (20 mL), and then extracted with 1:1 EtOAc:hexanes three times. The organic layer was washed with brine, and then dried and concentrated. The residue was purified by silica gel chromatography (0-100% EtOAc in hexanes) to give 3-[(N-benzyloxycarbonyl-N-ethyl-amino)-methyl]-4-bromo-benzoic acid ethyl ester, as well as the hydrolyzed product, which was combined with the product from the next step.

Step 6: 3-[(N-Benzyloxycarbonyl-N-ethyl-amino)-methyl]-4-bromo-benzoic acid ethyl ester (3.62 g, 7.2 mmol) was dissolved in MeOH (40 mL) and cooled to 0° C. 1N Aqueous LiOH (22 mL, 22 mmol) was added, and the reaction was stirred at room temperature for 3 hours. The mixture was quenched with 1N aqueous HCl (22 mL) and extracted three times with EtOAc. The combined organic layers were washed with brine, dried, and concentrated to give 3-[(N-benzyloxycarbonyl-N-ethyl-amino)-methyl]-4-bromo-benzoic acid, which was combined with the hydrolyzed product isolated in step 5.

Step 7: To 3-[(N-benzyloxycarbonyl-N-ethyl-amino)-methyl]-4-bromo-benzoic acid (8.9 g, 22.6 mmol) in MeCN (400 mL) was added cesium carbonate (18.4 g, 56.5 mmol), followed by benzyl bromide (2.95 mL, 24.9 mmol), and the reaction was stirred at room temperature overnight. The mixture was filtered and extracted with EtOAc and washed with $H_2O$. The organic layer was dried and concentrated, and the residue was purified by silica gel chromatography (0-25% EtOAc in hexanes) to give 3-[(N-benzyloxycarbonyl-N-ethyl-amino)-methyl]-4-bromo-benzoic acid benzyl ester.

Step 8: 3-[(N-Benzyloxycarbonyl-N-ethyl-amino)-methyl]-4-bromo-benzoic acid benzyl ester (5.5 g, 11.4 mmol), bis(pinacolato)diboron (4.35 g, 17.1 mmol), and potassium acetate (4.1 g, 45.6 mmol) were combined in 1,4-dioxane (200 mL), and the solution was purged with $N_2$ for 10 minutes. (1,1'-Bis(diphenylphosphino)ferrocene)-dichloropalladium(II) (0.466 g, 0.57 mmol) was added, and the reaction was stirred at 80° C. for 4 hours. Additional bis(diphenylphosphino)ferrocene)-dichloropalladium(II) (0.466 g, 0.57 mmol) was added, and the reaction was stirred at 80° C. overnight. The mixture was filtered over silica gel with 1:1 EtOAc:hexanes, and the filtrate was extracted with EtOAc three times and washed with brine. The organic layer was concentrated and purified by silica gel chromatography (0-30% EtOAc in hexanes) to give 3-[(N-benzyloxycarbonyl-N-ethyl-amino)-methyl]-4-(4,4,5,5-tetramethyl-[1,3,2]dioxaborolan-2-yl)-benzoic acid benzyl ester.

Step 9: 3-[(N-Benzyloxycarbonyl-N-ethyl-amino)-methyl]-4-(4,4,5,5-tetramethyl-[1,3,2]dioxaborolan-2-yl)-benzoic acid benzyl ester (1.96 g, 3.7 mmol), (5-bromo-pyridin-3-yl)-acetic acid ethyl ester (0.99 g, 4.1 mmol), and potassium carbonate (1.79 g, 13.0 mmol) were combined in DME (40 mL) and $H_2O$ (30 mL), and the solution was purged with $N_2$ for 10 minutes. Tetrakis(triphenylphosphine)palladium(0) (0.427 g, 0.37 mmol) was added, and the reaction was stirred at 70° C. overnight. The mixture was quenched with 1N aqueous HCl (13 mL) and extracted with EtOAc. The combined organic layers were washed with $H_2O$, and then dried and concentrated to give 3-[(N-benzyloxycarbonyl-N-ethyl-amino)-methyl]-4-(5-carboxymethyl-pyridin-3-yl)-benzoic acid benzyl ester.

Step 10: 3-[(N-Benzyloxycarbonyl-N-ethyl-amino)-methyl]-4-(5-carboxymethyl-pyridin-3-yl)-benzoic acid benzyl ester (0.369 g, 0.68 mmol) was dissolved in MeOH (4 mL) and cooled to 0° C. 1N Aqueous LiOH (3 mL, 3 mmol) was added, and the reaction was stirred at room temperature for 1 hour. The mixture was quenched with 1N aqueous HCl (3 mL) and extracted with EtOAc. The combined organic layers were washed with $H_2O$ and concentrated, and the residue was purified by preparative HPLC to give Compound 1.

Example 2

Synthesis of 4-(5-Carboxymethyl-pyridin-3-yl)-3-[(N-cyclopropanecarbonyl-N-ethyl-amino)-methyl]-benzoic acid (Compound 2)

Step 1: 3-[(N-Benzyloxycarbonyl-N-ethyl-amino)-methyl]-4-(5-carboxymethyl-pyridin-3-yl)-benzoic acid benzyl ester (1.74 g, 3.2 mmol) in EtOH (200 mL) was treated with sulfuric acid (2 mL), and the reaction was stirred at 95° C. for 2 hours. The mixture was cooled to room temperature and concentrated, and the residue was partitioned between EtOAc and $H_2O$. The solution was extracted with EtOAc, and the combined organic layers were washed with 1N aqueous HCl and concentrated. The crude material was purified by silica gel chromatography (0-100% EtOAc in hexanes) to give 3-[(N-benzyloxycarbonyl-N-ethyl-amino)-methyl]-4-(5-ethoxycarbonylmethyl-pyridin-3-yl)-benzoic acid ethyl ester.

Step 2: 3-[(N-Benzyloxycarbonyl-N-ethyl-amino)-methyl]-4-(5-ethoxycarbonylmethyl-pyridin-3-yl)-benzoic acid ethyl ester (0.5 g, 1 mmol) was dissolved in MeOH (20 mL), and the solution was purged with $N_2$ for 10 minutes. 10% Palladium on carbon (0.2 g) was added, and the reaction was stirred under an atmosphere on $H_2$ at room temperature for 3 hours. Additional 10% palladium on carbon (0.1 g) was added, and the reaction was stirred under $H_2$ overnight. The mixture was purged with $N_2$ and filtered over Celite. After washing with MeOH, the filtrate was concentrated to give 4-(5-ethoxycarbonylmethyl-pyridin-3-yl)-3-ethylaminomethyl-benzoic acid.

Step 3: 4-(5-Ethoxycarbonylmethyl-pyridin-3-yl)-3-ethylaminomethyl-benzoic acid (0.347 g, 1.0 mmol) and diisopropylethylamine (0.44 mL, 2.5 mmol) were combined in $CH_2Cl_2$ (75 mL). Cyclopropanecarbonyl chloride (0.12 mL, 1.3 mmol) was added slowly, and the reaction was stirred at room temperature for 10 minutes. The mixture was quenched with $H_2O$ (100 mL), and the product was extracted with $CH_2Cl_2$. The combined organic layers were washed with brine and concentrated. The crude material was dissolved in MeOH (75 mL), 1N aqueous LiOH (5 mL) was added and stirred at room temperature for 3 hours. Additional 1N aqueous LiOH (1 mL) was added and the reaction was stirred at room temperature for 3 days. The mixture was quenched with 1N aqueous HCl (5 mL) and extracted with EtOAc. The combined organic layers were washed with $H_2O$ and brine, and then concentrated to give 4-(5-carboxymethyl-pyridin-3-yl)-3-[(N-cyclopropanecarbonyl-N-ethyl-amino)-methyl]-benzoic acid.

Example 3

Synthesis of (5-{2-[(N-Benzyl-N-cyclopropanecarbonyl-amino)-methyl]-4-cyano-phenyl}-pyridin-3-yl)-acetic acid (Compound 3)

Step 1: 4-Bromo-3-methylbenzonitrile (6.19 g, 31.6 mmol), N-bromosuccinimide (11.81 g, 66.4 mmol), and benzoyl peroxide (1.52 g, 6.3 mmol) were combined in $CCl_4$ (500 mL) and stirred at 80° C. for 3 days. The mixture was filtered over silica gel, diluted with $H_2O$, and extracted with EtOAc. The combined organic layers were dried and concentrated, and the residue was purified by silica gel chromatography (0-30% EtOAc in hexanes) to give 4-bromo-3-dibromomethyl-benzonitrile.

Step 2: 4-Bromo-3-dibromomethyl-benzonitrile (5.66 g, 16 mmol) was dissolved in EtOH (150 mL) and heated to 60° C. Silver nitrate (6.80 g, 40 mmol), prepared as a solution in $H_2O$ (40 mL), was added dropwise, and the reaction was heated to 75° C. and stirred overnight. The organic layer was decanted, concentrated, and filtered, and the residue was partitioned between EtOAc and $H_2O$. The product was extracted with EtOAc, and the combined organic layers were concentrated and purified by silica gel chromatography (0-30% EtOAc in hexanes) to give 4-bromo-3-formyl-benzonitrile.

Step 3: To 4-bromo-3-formyl-benzonitrile (2.42 g, 11.5 mmol) in MeOH (450 mL) was added benzylamine (1.88 mL, 17.3 mmol) and sodium cyanoborohydride (1.09 g, 17.3 mmol). Acetic acid (0.99 mL, 17.3 mmol) was added dropwise, and the reaction was stirred at room temperature overnight. The mixture was quenched with $H_2O$ and extracted with EtOAc. The combined organic layers were dried, concentrated, and purified by silica gel chromatography (0-30% EtOAc in hexanes) to give 3-(benzylamino-methyl)-4-bromo-benzonitrile.

Step 4: 3-(Benzylamino-methyl)-4-bromo-benzonitrile and cyclopropanecarbonyl chloride were reacted as described in Example 2, Step 3 to provide cyclopropanecarboxylic acid benzyl-(2-bromo-5-cyano-benzyl)-amide.

Step 5: Cyclopropanecarboxylic acid benzyl-(2-bromo-5-cyano-benzyl)-amide and bis(pinacolato)diboron were reacted as described in Example 1, Step 8 to provide cyclopropanecarboxylic acid benzyl-[5-cyano-2-(4,4,5,5-tetramethyl-[1,3,2]dioxaborolan-2-yl)-benzyl]-amide.

Step 6: Cyclopropanecarboxylic acid benzyl-[5-cyano-2-(4,4,5,5-tetramethyl-[1,3,2]dioxaborolan-2-yl)-benzyl]-amide (1.33 g, 3.2 mmol), (5-bromo-pyridin-3-yl)-acetic acid ethyl ester (1.02 g, 4.2 mmol), and potassium carbonate (1.55 g, 11.2 mmol) were combined in DME (40 mL) and $H_2O$ (30 mL), and the solution was purged with $N_2$ for 15 minutes. Tetrakis(triphenylphosphine)palladium(0) (0.370 g, 0.35 mmol) was added, and the reaction was stirred at 70° C. for 1 hour. The mixture was diluted with $H_2O$ and 1N aqueous HCl (15 mL), and extracted with EtOAc. The combined organic layers were concentrated and purified by preparative HPLC to give (5-{2-[(benzyl-cyclopropanecarbonyl-amino)-methyl]-4-cyano-phenyl}-pyridin-3-yl)-acetic acid ethyl ester, as well as the some of the hydrolyzed ester product.

Step 7: (5-{2-[(N-Benzyl-N-cyclopropanecarbonyl-amino)-methyl]-4-cyano-phenyl}-pyridin-3-yl)-acetic acid ethyl ester (0.1 g, 0.22 mmol) was dissolved in MeOH (10 mL) and treated with 1N aqueous LiOH (1 mL) dropwise. The reaction was stirred at room temperature for 1 hour, and then quenched with 1N aqueous HCl (1 ml) and extracted with EtOAc. The combined organic layers were dried and concentrated to give Compound 3.

Example 4

Synthesis of {5-[2-[(N-Benzyl-N-cyclopropanecarbonyl-amino)-methyl]-4-(2H-tetrazol-5-yl)-phenyl]-pyridin-3-yl}-acetic acid (Compound 4)

Step 1: (5-{2-[(N-Benzyl-N-cyclopropanecarbonyl-amino)-methyl]-4-cyano-phenyl}-pyridin-3-yl)-acetic acid ethyl ester (0.253 g, 0.56 mmol) was dissolved in toluene (10 mL). Dibutyltin oxide (0.014 g, 0.06 mmol) was added, followed by azidotrimethylsilane (0.09 mL, 0.67 mmol), and the reaction was stirred at 80° C. for 5 hours, and at 100° C.

overnight. The mixture was quenched with $H_2O$ and extracted with EtOAc. The combined organic layers were concentrated and purified by preparative HPLC to give {5-[2-[(N-benzyl-N-cyclopropanecarbonyl-amino)-methyl]-4-(2H-tetrazol-5-yl)-phenyl]-pyridin-3-yl}-acetic acid ethyl ester the title compound.

Step 2: {5-[2-[(N-Benzyl-N-cyclopropanecarbonyl-amino)-methyl]-4-(2H-tetrazol-5-yl)-phenyl]-pyridin-3-yl}-acetic acid ethyl ester was hydrolyzed to the acid as described in Example 1, Step 10.

Example 5

Synthesis of (5-{4-Benzylcarbamoyl-2-[(N-benzyl-N-cyclopropanecarbonyl-amino)-methyl]-phenyl}-pyridin-3-yl)-acetic acid (Compound 5)

Step 1: 4-Bromo-3-methyl-benzoic acid ethyl ester was reacted as described in Example 3, Step 1 to provide 4-bromo-3-dibromomethyl-benzoic acid ethyl ester.

Step 2: 4-Bromo-3-dibromomethyl-benzoic acid ethyl ester (6.4 g, 16 mmol) was dissolved in EtOH (200 mL) and heated to 60° C. Silver nitrate (6.80 g, 40 mmol), prepared as a solution in $H_2O$ (50 mL), was added dropwise, resulting in a precipitate. After 1 hour, the mixture was decanted, and the precipitate was washed with EtOH (3×50 mL) and decanted after each wash. The combined EtOH solution was treated with 1N aqueous HCl (40 mL), which resulted in additional precipitate formation. The mixture was filtered, and the filtrate was concentrated and partitioned between EtOAc and $H_2O$. The aqueous layer was separated and extracted with EtOAc, and the combined organic layers were concentrated. The crude material was dissolved in MeOH (100 mL) and treated with 2N aqueous $H_2SO_4$ (15 mL) for 1 hour at room temperature. After work-up, the crude material was purified by silica gel chromatography to give a mixture of the aldehyde and the dimethyl acetal. The mixture was dissolved in 1,4-dioxane and treated with 2N aqueous $H_2SO_4$ (80 mL), and stirred overnight at room temperature. The solution was diluted with EtOAc and $H_2O$, and the organic layer was separated, dried, and concentrated to give 4-bromo-3-formyl-benzoic acid ethyl ester.

Step 3: 4-Bromo-3-formyl-benzoic acid ethyl ester (3.3 g, 12.9 mmol) and benzylamine (2.1 mL, 19.3 mmol) were combined in EtOH (150 mL) with 4 Å molecular sieves. Sodium cyanoborohydride (1.21 g, 19.3 mmol) was added, followed by acetic acid (1.1 mL, 19.3 mmol), and the reaction was stirred at room temperature for 1 hour. Aqueous work-up provided 3-(benzylamino-methyl)-4-bromo-benzoic acid ethyl ester.

Step 4: 3-(Benzylamino-methyl)-4-bromo-benzoic acid ethyl ester (5.0 g, 12.9 mmol) and diisopropylethylamine (6.7 mL, 38.7 mmol) were combined in $CH_2Cl_2$ (100 mL) at room temperature. Cyclopropanecarbonyl chloride (1.77 mL, 19.4 mmol) was added dropwise, and the reaction was stirred at room temperature until no starting material was seen by analytical LCMS. The mixture was worked-up and purified by silica gel chromatography to give 3-[(N-benzyl-N-cyclopropanecarbonyl-amino)-methyl]-4-bromo-benzoic acid ethyl ester.

Step 5: 3-[(N-Benzyl-N-cyclopropanecarbonyl-amino)-methyl]-4-bromo-benzoic acid ethyl ester (2.03 g, 4.9 mmol) was treated with 1N aqueous LiOH (10 mL) in MeOH (60 mL) and THF (10 mL). After stirring for 1 hour at room temperature, additional 1N aqueous LiOH (10 mL) was added, and the reaction was stirred for another 2 hours. The mixture was poured into $H_2O$ (200 mL) and neutralized with 1N aqueous HCl (50 mL). The solution was extracted three times with EtOAc to give 3-[(N-benzyl-N-cyclopropanecarbonyl-amino)-methyl]-4-bromo-benzoic acid.

Step 6: 3-[(N-Benzyl-N-cyclopropanecarbonyl-amino)-methyl]-4-bromo-benzoic acid (0.1 g, 0.26 mmol) and catalytic DMF (0.01 mL) were combined in $CH_2Cl_2$ (4 mL) at room temperature. Oxalyl chloride (0.03 mL, 0.33 mmol) was added, and the reaction was stirred for 30 minutes. The solution was concentrated and dried under vacuum, and then NMP (3 mL) and diisopropylethylamine (0.14 mL, 0.78 mmol) were added. Benzylamine (0.04 mL, 0.39 mmol) was then added, and the reaction was stirred for 5 minutes. The mixture was poured into $H_2O$ and partitioned with 1:1 EtOAc:hexanes. The organic layer was washed with saturated aqueous $NaHCO_3$, $H_2O$, and dilute brine, and then dried, filtered, and concentrated to give N-benzyl-3-[(N-benzyl-N-cyclopropanecarbonyl-amino)-methyl]-4-bromo-benzamide.

Step 7: N-Benzyl-3-[(N-benzyl-N-cyclopropanecarbonyl-amino)-methyl]-4-bromo-benzamide and bis(pinacolato)diboron were reacted as described in Example 1, Step 8 to provide N-benzyl-3-[(N-benzyl-N-cyclopropanecarbonyl-amino)-methyl]-4-(4,4,5,5-tetramethyl-[1,3,2]dioxaborolan-2-yl)-benzamide.

Step 8: N-Benzyl-3-[(N-benzyl-N-cyclopropanecarbonyl-amino)-methyl]-4-(4,4,5,5-tetramethyl-[1,3,2]dioxaborolan-2-yl)-benzamide and (5-bromo-pyridin-3-yl)-acetic acid ethyl ester were reacted as described in Example 3, Step 6 to provide (5-{4-benzylcarbamoyl-2-[(N-benzyl-N-cyclopropanecarbonyl-amino)-methyl]-phenyl}-pyridin-3-yl)-acetic acid ethyl ester.

Step 9: (5-{4-Benzylcarbamoyl-2-[(N-benzyl-N-cyclopropanecarbonyl-amino)-methyl]-phenyl}-pyridin-3-yl)-acetic acid ethyl ester was hydrolyzed to the acid as described in Example 3, Step 7.

Example 6

Synthesis of (5-{2-[(N-Benzyl-N-cyclopropanecarbonyl-amino)-methyl]-4-methylcarbamoyl-phenyl}-pyridin-3-yl)-acetic acid (Compound 6)

Step 1: 3-[(N-Benzyl-N-cyclopropanecarbonyl-amino)-methyl]-4-bromo-benzoic acid and methylamine (2M in THF) were reacted as described in Example 5, Step 6 to provide 3-[(N-benzyl-N-cyclopropanecarbonyl-amino)-methyl]-4-bromo-N-methyl-benzamide.

Step 2: 3-[(N-Benzyl-N-cyclopropanecarbonyl-amino)-methyl]-4-bromo-N-methyl-benzamide and bis(pinacolato)diboron were reacted as described in Example 1, Step 8 to provide 3-[N-benzyl-N-cyclopropanecarbonyl-amino)-methyl]-N-methyl-4-(4,4,5,5-tetramethyl-[1,3,2]dioxaborolan-2-yl)-benzamide.

Step 3: 3-[(N-benzyl-N-cyclopropanecarbonyl-amino)-methyl]-N-methyl-4-(4,4,5,5-tetramethyl-[1,3,2]dioxaborolan-2-yl)-benzamide and (5-bromo-pyridin-3-yl)-acetic acid ethyl ester were reacted as described in Example 3, Step 6 to provide (5-{2-[(N-benzyl-N-cyclopropanecarbonyl-amino)-methyl]-4-methylcarbamoyl-phenyl}-pyridin-3-yl)-acetic acid ethyl ester.

Step 4: (5-{2-[(N-Benzyl-N-cyclopropanecarbonyl-amino)-methyl]-4-methylcarbamoyl-phenyl}-pyridin-3-yl)-acetic acid ethyl ester was hydrolyzed to the acid as described in Example 3, Step 7.

Example 7

Synthesis of (5-{2-[(N-Benzyl-N-cyclopropanecarbonyl-amino)-methyl]-4-tert-butylcarbamoyl-phenyl}-pyridin-3-yl)-acetic acid (Compound 7)

Step 1: 3-[(N-Benzyl-N-cyclopropanecarbonyl-amino)-methyl]-4-bromo-benzoic acid and tert-butylamine were reacted as described in Example 5, Step 6 to provide 3-[(N-benzyl-N-cyclopropanecarbonyl-amino)-methyl]-4-bromo-N-tert-butyl-benzamide Step 2: 3-[(N-benzyl-N-cyclopropanecarbonyl-amino)-methyl]-4-bromo-N-tert-butyl-benzamide and bis(pinacolato)diboron were reacted as described in Example 1, Step 8 to provide 3-[N-benzyl-N-cyclopropanecarbonyl-amino)-methyl]-N-tert-butyl-4-(4,4,5,5-tetramethyl-[1,3,2]dioxaborolan-2-yl)-benzamide.

Step 3: 3-[(N-benzyl-N-cyclopropanecarbonyl-amino)-methyl]-N-tert-butyl-4-(4,4,5,5-tetramethyl-[1,3,2]dioxaborolan-2-yl)-benzamide and (5-bromo-pyridin-3-yl)-acetic acid ethyl ester were reacted as described in Example 3, Step 6 to provide (5-{2-[(N-benzyl-N-cyclopropanecarbonyl-amino)-methyl]-4-tert-butylcarbamoyl-phenyl}-pyridin-3-yl)-acetic acid ethyl ester.

Step 4: (5-{2-[(N-Benzyl-N-cyclopropanecarbonyl-amino)-methyl]-4-tert-butylcarbamoyl-phenyl}-pyridin-3-yl)-acetic acid ethyl ester was hydrolyzed to the acid as described in Example 3, Step 7.

Example 8

Synthesis of (5-{2-[(N-Cyclopropanecarbonyl-N-ethyl-amino)-methyl]-4-trifluoromethyl-phenyl}-pyridin-3-yl)-acetic acid (Compound 8)

Step 1: To 2-bromo-5-(trifluoromethyl)benzaldehyde (7.5 g, 29.6 mmol) in MeOH (80 mL) was added ethylamine (2M in MeOH; 30 mL, 60 mmol), sodium cyanoborohydride (3.7 g, 58.9 mmol), and acetic acid (1.7 mL, 26.2 mmol), and the reaction was stirred at room temperature for 4 days. The mixture was quenched with saturated aqueous $NaHCO_3$ and extracted with $CH_2Cl_2$, and the combined organic layers were dried over $MgSO_4$, filtered, and concentrated. The crude material was purified by silica gel chromatography (0-4% MeOH in $CH_2Cl_2$) to give (2-bromo-5-trifluoromethyl-benzyl)-ethyl-amine.

Step 2: (2-Bromo-5-trifluoromethyl-benzyl)-ethyl-amine (3.6 g, 12.8 mmol) and di-tent-butyl dicarbonate (3.74 g, 17.1 mmol) were combined in $CH_2Cl_2$ (30 mL) and stirred at room temperature for 1 hour. The mixture was quenched with saturated aqueous $NaHCO_3$ and extracted with $CH_2Cl_2$, and the combined organic layers were dried over $MgSO_4$, filtered, and concentrated to give (2-bromo-5-trifluoromethyl-benzyl)-ethyl-carbamic acid tert-butyl ester.

Step 3: (2-Bromo-5-trifluoromethyl-benzyl)-ethyl-carbamic acid tert-butyl ester (3.23 g, 8.5 mmol), bis(pinacolato)diboron (2.57 g, 10.1 mmol), potassium acetate (2.5 g, 25.5 mmol), and bis(diphenylphosphino)ferrocene)-dichloropalladium(II) (0.390 g, 0.5 mmol) were combined in 1,4-dioxane (30 mL). The solution was purged with $N_2$, and then the reaction was stirred at 85° C. for 14 hours. The mixture was concentrated and partitioned between EtOAc and $H_2O$. The aqueous layer was extracted with EtOAc, and the combined organic layers were dried over $MgSO_4$, filtered, and concentrated. The residue was filtered through a plug of silica gel (20% EtOAc in hexanes) to give ethyl-[2-(4,4,5,5-tetramethyl-[1,3,2]dioxaborolan-2-yl)-5-trifluoromethyl-benzyl]-carbamic acid tert-butyl ester.

Step 4: Ethyl-[2-(4,4,5,5-tetramethyl-[1,3,2]dioxaborolan-2-yl)-5-trifluoromethyl-benzyl]-carbamic acid tert-butyl ester (1.0 g, 2.33 mmol), (5-bromo-pyridin-3-yl)-acetic acid methyl ester (0.535 g, 2.33 mmol), potassium carbonate (0.807 g, 5.8 mmol), and tetrakis(triphenylphosphine)palladium(0) (0.100 g, 0.09 mmol) were combined in DME (8 mL) and $H_2O$ (4 mL). The solution was purged with $N_2$, and then the reaction was stirred at 80° C. for 12 hours. The mixture was partitioned between EtOAc and $H_2O$, and the aqueous layer was extracted with EtOAc. The combined organic layers were dried over $MgSO_4$, filtered, and concentrated, and the residue was purified by silica gel chromatography to give (5-{2-[(N-tert-butoxycarbonyl-N-ethyl-amino)-methyl]-4-trifluoromethyl-phenyl}-pyridin-3-yl)-acetic acid methyl ester.

Step 5: To (5-{2-[(N-tert-butoxycarbonyl-N-ethyl-amino)-methyl]-4-trifluoromethyl-phenyl}-pyridin-3-yl)-acetic acid methyl ester (0.742 g, 1.6 mmol) in $CH_2Cl_2$ (3 mL) was added 4N HCl in 1,4-dioxane (4 mL), and the reaction was stirred at room temperature until no starting material was seen by analytical LCMS. The mixture was then concentrated to give [5-(2-ethylaminomethyl-4-trifluoromethyl-phenyl)-pyridin-3-yl]-acetic acid methyl ester, dihydrochloride.

Step 6: [5-(2-Ethylaminomethyl-4-trifluoromethyl-phenyl)-pyridin-3-yl]-acetic acid methyl ester, dihydrochloride (0.108 g, 0.25 mmol), cyclopropanecarboxylic acid (0.02 mL, 0.30 mmol), 1-ethyl-3-(3-dimethylaminopropyl)carbodiimide hydrochloride (0.073 g, 0.38 mmol), 1-hydroxybenzotriazole hydrate (0.051 g, 0.38 mmol), and triethylamine (0.16 mL, 1.14 mmol) were combined in $CH_2Cl_2$ (1 mL) and stirred at room temperature for 45 minutes. The mixture was diluted with aqueous $NH_4Cl$ and extracted with $CH_2Cl_2$. The combined organic layers were dried over $MgSO_4$, filtered, and concentrated, and the residue was purified by silica gel chromatography (0-100% EtOAc in hexanes) to give (5-{2-[(N-cyclopropanecarbonyl-N-ethyl-amino)-methyl]-4-trifluoromethyl-phenyl}-pyridin-3-yl)-acetic acid methyl ester.

Step 7: (5-{2-[(N-Cyclopropanecarbonyl-N-ethyl-amino)-methyl]-4-trifluoromethyl-phenyl}-pyridin-3-yl)-acetic acid methyl ester (0.069 g, 0.16 mmol) was dissolved in THF (1 mL) and MeOH (0.8 mL) and treated with 1N aqueous NaOH (0.5 mL). The reaction was stirred at room temperature for 1 hour. The mixture was neutralized with 1N aqueous HCl and extracted twice with $CH_2Cl_2$. The combined organic layers were dried over $MgSO_4$, filtered, and concentrated to give Compound 8.

Example 9

Synthesis of (2-Chloro-5-{2-[(N-cyclopropanecarbonyl-N-ethyl-amino)-methyl]-4-trifluoromethyl-phenyl}-pyridin-3-yl)-acetic acid (Compound 9)

Step 1: To (5-bromo-pyridin-3-yl)-acetic acid ethyl ester (5.0 g, 20.5 mmol) in $CH_2Cl_2$ (50 mL) was added meta-chloroperoxybenzoic acid (77 wt %; 7.03 g, 30.7 mmol), and the reaction was stirred overnight at room temperature. The mixture was neutralized with saturated aqueous $NaHCO_3$ and extracted with $CH_2Cl_2$. The combined organic layers were washed with saturated aqueous $NaHCO_3$ and 1N aqueous NaOH to give (5-bromo-1-oxy-pyridin-3-yl)-acetic acid ethyl ester.

Step 2: (5-Bromo-1-oxy-pyridin-3-yl)-acetic acid ethyl ester (4.28 g, 16.5 mmol) was treated with phosphorus oxychloride (20 mL) and stirred at 90° C. for 1.5 hours. After cooling to room temperature, the reaction was quenched by pouring into saturated aqueous $NaHCO_3$, and the mixture was extracted with EtOAc. The combined organic layers were washed with brine, dried over $MgSO_4$, filtered, and concentrated, and the residue was purified by silica gel chromatography (0-100% EtOAc in hexanes) to give (5-bromo-2-chloro-pyridin-3-yl)-acetic acid ethyl ester and (5-bromo-6-chloro-pyridin-3-yl)-acetic acid ethyl ester.

Step 3: 2-Bromo-5-(trifluoromethyl)benzaldehyde and bis(pinacolato)diboron were reacted as described in Example 1, Step 8 to provide 2-(4,4,5,5-tetramethyl-[1,3,2]dioxaborolan-2-yl)-5-trifluoromethyl-benzaldehyde.

Step 4: (5-Bromo-2-chloro-pyridin-3-yl)-acetic acid ethyl ester and 2-(4,4,5,5-tetramethyl-[1,3,2]dioxaborolan-2-yl)-5-trifluoromethyl-benzaldehyde were reacted as described in Example 3, Step 6 to provide [2-chloro-5-(2-formyl-4-trifluoromethyl-phenyl)-pyridin-3-yl]-acetic acid ethyl ester.

Step 5: [2-Chloro-5-(2-formyl-4-trifluoromethyl-phenyl)-pyridin-3-yl]-acetic acid ethyl ester and ethylamine (2M in THF) were reacted as described in Example 3, Step 3 to provide [2-chloro-5-(2-ethylaminomethyl-4-trifluoromethyl-phenyl)-pyridin-3-yl]-acetic acid ethyl ester.

Step 6: [2-Chloro-5-(2-ethylaminomethyl-4-trifluoromethyl-phenyl)-pyridin-3-yl]-acetic acid ethyl ester and cyclopropanecarboxylic acid were reacted as described in Example 8, Step 6 to provide (2-chloro-5-{2-[(N-cyclopropanecarbonyl-N-ethyl-amino)-methyl]-4-trifluoromethyl-phenyl}-pyridin-3-yl)-acetic acid ethyl ester.

Step 7: (2-Chloro-5-{2-[(N-cyclopropanecarbonyl-N-ethyl-amino)-methyl]-4-trifluoromethyl-phenyl}-pyridin-3-yl)-acetic acid ethyl ester was hydrolyzed to the acid as described in Example 8, Step 7.

Example 10

Synthesis of (5-{2-[(N-Cyclopropanecarbonyl-N-ethyl-amino)-methyl]-4-trifluoromethyl-phenyl}-6-methoxy-pyridin-3-yl)-acetic acid (Compound 10)

Step 1: To 5-bromo-2-methoxypyridine (0.564 g, 3.0 mmol) and sodium acetate (0.246 g, 3.0 mmol) in acetic acid (3 mL) was added bromine (0.27 mL, 5.25 mmol), and the mixture was stirred at 80° C. for 3 hours, and then at room temperature overnight. The mixture was diluted with $H_2O$ and extracted with EtOAc, and the combined organic layers were washed with saturated aqueous $Na_2CO_3$ and saturated aqueous $Na_2S_2O_3$. The organic layer was concentrated and dried under high vacuum to give 3,5-dibromo-2-methoxy-pyridine.

Step 2: 2-(4,4,5,5-Tetramethyl-[1,3,2]dioxaborolan-2-yl)-5-trifluoromethyl-benzaldehyde (1.59 g, 4.4 mmol), 3,5-dibromo-2-methoxy-pyridine (1.19 g, 4.4 mmol), and potassium carbonate (2.17 g, 15.6 mmol) were combined in DME (13 mL) and $H_2O$ (6 mL). The solution was purged with $N_2$ for 30 minutes, and dichlorobis(triphenylphosphine)palladium(II) (0.156 g, 0.22 mmol) was added. The reaction was stirred at 85° C. overnight, and then cooled to room temperature and worked-up with EtOAc and brine. The combined organic layers were dried over $MgSO_4$, filtered, and concentrated, and the residue was purified by silica gel chromatography (0-100% EtOAc in hexanes) to give 2-(5-bromo-2-methoxy-pyridin-3-yl)-5-trifluoromethyl-benzaldehyde, which was repurified by preparative HPLC.

Step 3: 2-(5-Bromo-2-methoxy-pyridin-3-yl)-5-trifluoromethyl-benzaldehyde and ethylamine (2M in THF) as described in Example 3, Step 3 to provide [2-(5-bromo-2-methoxy-pyridin-3-yl)-5-trifluoromethyl-benzyl]-ethyl-amine.

Step 4: [2-(5-Bromo-2-methoxy-pyridin-3-yl)-5-trifluoromethyl-benzyl]-ethyl-amine and cyclopropanecarboxylic acid were reacted as described in Example 8, Step 6 to provide cyclopropanecarboxylic acid [2-(5-bromo-2-methoxy-pyridin-3-yl)-5-trifluoromethyl-benzyl]-ethyl-amide.

Step 5: Cyclopropanecarboxylic acid [2-(5-bromo-2-methoxy-pyridin-3-yl)-5-trifluoromethyl-benzyl]-ethyl-amide (0.215 g, 0.47 mmol), (trimethylsilyl)acetylene (0.07 mL, 0.47 mmol), and copper iodide (0.012 g, 0.05 mmol) were combined in triethylamine (2 mL), and the solution was purged with $N_2$ for 25 minutes. Dichlorobis(triphenylphosphine)palladium(II) (0.039 g, 0.05 mmol) was added, and the reaction was stirred at room temperature overnight. The mixture was worked-up with $CH_2Cl_2$ and $H_2O$, and the combined organic layers were dried, filtered, and concentrated. The residue was purified by silica gel chromatography (0-100% EtOAc in hexanes) to give cyclopropanecarboxylic acid ethyl-[2-(2-methoxy-5-trimethylsilanylethynyl-pyridin-3-yl)-5-trifluoromethyl-benzyl]-amide.

Step 5: To cyclopropanecarboxylic acid ethyl-[2-(2-methoxy-5-trimethylsilanylethynyl-pyridin-3-yl)-5-trifluoromethyl-benzyl]-amide (0.205 g, 0.42 mmol) in THF (2 mL) at 0° C. was added borane tetrahydrofuran complex (1M in THF; 0.48 mL, 0.48 mmol), and the reaction was stirred for 2 hours. Once no starting material was seen by analytical LCMS, MeOH (0.22 mL), hydrogen peroxide (0.04 mL, 0.43 mmol), and 3M aqueous sodium hydroxide (0.22 ml) was added, and the reaction was stirred for 1 hour. Additional hydrogen peroxide (0.1 mL) was added, and the reaction was stirred for another hour. The mixture was then acidified and extracted with EtOAc, and the combined organic layers were washed with brine, dried over $MgSO_4$, filtered, and concentrated. The residue was purified by preparative HPLC to give Compound 10.

Example 11

Synthesis of (6-Chloro-5-{2-[(N-cyclopropanecarbonyl-N-ethyl-amino)-methyl]-4-trifluoromethyl-phenyl}-pyridin-3-yl)-acetic acid (Compound 11)

Step 1: 2-Bromo-5-(trifluoromethyl)benzaldehyde (20 g, 79.1 mmol), ethylamine (2M in MeOH; 59.3 mL, 118.6 mmol), and sodium cyanoborohydride (7.45 g, 118.6 mmol) were combined in MeOH (200 mL). Acetic acid (6.79 mL, 118.6 mmol) was added, and the reaction was stirred at room temperature overnight. The mixture was concentrated and partitioned between $CH_2Cl_2$ and $H_2O$. The aqueous layer was separated and extracted twice with $CH_2Cl_2$, and the combined organic layers were dried over $Na_2SO_4$ and concentrated to give (2-bromo-5-trifluoromethyl-benzyl)-ethyl-amine.

Step 2: To (2-bromo-5-trifluoromethyl-benzyl)-ethyl-amine (22.3 g, 79.1 mmol) and triethylamine (16.53 mL, 118.6 mmol) in $CH_2Cl_2$ (200 mL) was added cyclopropanecarbonyl chloride (8.68 mL, 94.9 mmol) dropwise over 15 minutes, and the reaction was stirred at room temperature for 2 hours. The mixture was partitioned between $CH_2Cl_2$ and $H_2O$, and the aqueous layer was separated and extracted twice with $CH_2Cl_2$. The combined organic layers were dried and concentrated, and the residue was purified by silica gel chromatography (10-30% EtOAc in hexanes) to give cyclopropanecarboxylic acid (2-bromo-5-trifluoromethyl-benzyl)-ethyl-amide.

Step 3: Cyclopropanecarboxylic acid (2-bromo-5-trifluoromethyl-benzyl)-ethyl-amide (22.1 g, 63.1 mmol), bis(pinacolato)diboron (17.6 g, 69.5 mmol), and potassium acetate (15.5 g, 157.9 mmol) were combined in 1,4-dioxane, and the solution was purged with $N_2$. (1,1'-Bis(diphenylphosphino)ferrocene)-dichloropalladium(II) (2.58 g, 3.2 mmol) was added, and the reaction was stirred at 100° C. overnight. After cooling to room temperature, the mixture was filtered through Celite and rinsed with EtOAc and $H_2O$. The filtrate was worked up with brine and EtOAc, and the organic layer was separated, dried and concentrated. The residue was purified by silica gel chromatography (10-20% EtOAc in hexanes) to give cyclopropanecarboxylic acid ethyl-[2-(4,4,5,5-tetramethyl-[1,3,2]dioxaborolan-2-yl)-5-trifluoromethyl-benzyl]-amide.

Step 4: (5-Bromo-6-chloro-pyridin-3-yl)-acetic acid ethyl ester (0.549 g, 1.97 mmol), cyclopropanecarboxylic acid ethyl-[2-(4,4,5,5-tetramethyl-[1,3,2]dioxaborolan-2-yl)-5-trifluoromethyl-benzyl]-amide (0.787 g, 1.97 mmol), and potassium carbonate (0.824 g, 5.91 mmol) were combined in DME (6 mL) and $H_2O$ (3 mL), and the solution was purged with $N_2$ for 40 minutes. Tetrakis(triphenylphosphine)palladium(0) (0.338 g, 0.20 mmol) was added, and the reaction was stirred at 85° C. for 2 hours. After cooling to room temperature, the mixture was worked-up with EtOAc, $H_2O$, and brine, and the organic layer was separated, dried, filtered, and concentrated. The residue was purified by silica gel chromatography (0-100% EtOAc in hexanes) to give (6-chloro-5-{2-[(N-cyclopropanecarbonyl-N-ethyl-amino)-methyl]-4-trifluoromethyl-phenyl}-pyridin-3-yl)-acetic acid ethyl ester.

Step 5: (6-Chloro-5-{2-[(N-cyclopropanecarbonyl-N-ethyl-amino)-methyl]-4-trifluoromethyl-phenyl}-pyridin-3-yl)-acetic acid ethyl ester was hydrolyzed to the acid as described in Example 8, Step 7.

Example 12

Synthesis of (5-{2-[(N-Benzyloxycarbonyl-N-ethyl-amino)-methyl]-4-trifluoromethyl-phenyl}-pyridin-3-yl)-acetic acid (Compound 12)

Step 1: 2-(4,4,5,5-Tetramethyl-[1,3,2]dioxaborolan-2-yl)-5-trifluoromethyl-benzaldehyde and (5-bromo-pyridin-3-yl)-acetic acid methyl ester were reacted as described in Example 8, Step 4 to provide [5-(2-formyl-4-trifluoromethyl-phenyl)-pyridin-3-yl]-acetic acid methyl ester.

Step 2: [5-(2-Formyl-4-trifluoromethyl-phenyl)-pyridin-3-yl]-acetic acid methyl ester and ethylamine (2M in MeOH) were reacted as described in Example 8, Step 1 to provide [5(2-ethylaminomethyl-4-trifluoromethyl-phenyl)-pyridin-3-yl]-acetic acid methyl ester.

Step 3: [5-(2-Ethylaminomethyl-4-trifluoromethyl-phenyl)-pyridin-3-yl]-acetic acid methyl ester and benzyl chloroformate were reacted as described in Example 11, Step 2 to provide (5-{2-[(N-benzyloxycarbonyl-N-ethyl-amino)-methyl]-4-trifluoromethyl-phenyl}-pyridin-3-yl)-acetic acid methyl ester.

Step 4: (5-{2-[(N-Benzyloxycarbonyl-N-ethyl-amino)-methyl]-4-trifluoromethyl-phenyl}-pyridin-3-yl)-acetic acid methyl ester (0.1 g, 0.2 mmol) in THF (2 mL), MeOH (0.5 mL), and $H_2O$ (0.5 mL) was treated with lithium hydroxide (0.03 g) and stirred at room temperature until no starting material was seen by analytical LCMS. The reaction was neutralized with citric acid to pH 4 and extracted with EtOAc, and the combined organic layers were washed with H₂O, dried over MgSO₄, filtered, and concentrated to give Compound 12.

Example 13

Synthesis of (5-{2-[(N-tert-Butoxycarbonyl-N-ethyl-amino)-methyl]-4-trifluoromethyl-phenyl}-pyridin-3-yl)-acetic acid (Compound 13)

(5-{2-[(N-tert-Butoxycarbonyl-N-ethyl-amino)-methyl]-4-trifluoromethyl-phenyl}-pyridin-3-yl)-acetic acid methyl ester was hydrolyzed to the acid as described in Example 12, Step 4.

Example 14

Synthesis of {5-[2-(3-Benzyl-1-ethyl-ureidomethyl)-4-trifluoromethyl-phenyl]-pyridin-3-yl}-acetic acid (Compound 14)

[5-(2-Ethylaminomethyl-4-trifluoromethyl-phenyl)-pyridin-3-yl]-acetic acid methyl ester, dihydrochloride and benzyl isocyanate were reacted as described in Example 2, Step 3, to provide {5-[2-(3-benzyl-1-ethyl-ureidomethyl)-4-trifluoromethyl-phenyl]-pyridin-3-yl}-acetic acid methyl ester. The ester was hydrolyzed to the acid as described in Example 12, Step 4.

Example 15

Synthesis of (5-{2-[(N-Benzyloxycarbonyl-N-ethyl-amino)-methyl]-4-trifluoromethyl-phenyl}-1-oxy-pyridin-3-yl)-acetic acid (Compound 15)

(5-{2-[(N-Benzyloxycarbonyl-N-ethyl-amino)-methyl]-4-trifluoromethyl-phenyl}-pyridin-3-yl)-acetic acid (0.1 g, 0.2 mmol) and meta-chloroperoxybenzoic acid (77 wt %; 0.05 g, 0.2 mmol) were combined in CH₂Cl₂ (2 mL) and stirred at room temperature until no starting material was seen by analytical LCMS. The mixture was concentrated and purified by preparative HPLC to give Compound 15.

Example 16

Synthesis of (5-{2-[(N-Ethyl-N-phenylacetyl-amino)-methyl]-4-trifluoromethyl-phenyl}-pyridin-3-yl)-acetic acid (Compound 16)

Step 1: Methyl phenylacetate (5.03 g, 33.5 mmol) was treated with 1N aqueous NaOH (22 mL, 22 mmol) in THF (40 mL) and MeOH (4 mL), and stirred overnight at room temperature. Additional 1N aqueous NaOH (22 mL, 22 mmol) was added, and the reaction was stirred for 6 hours at room temperature. The mixture was acidified with 1N aqueous HCl to pH 3-4 and extracted with EtOAc three times. The combined organic layers were dried and concentrated to give phenyl-acetic acid.

Step 2: [5-(2-Ethylaminomethyl-4-trifluoromethyl-phenyl)-pyridin-3-yl]-acetic acid methyl ester, dihydrochloride and phenyl-acetic acid were reacted as described in Example 8, Step 6 to provide (5-{2-[(N-ethyl-N-phenylacetyl-amino)-methyl]-4-trifluoromethyl-phenyl}-pyridin-3-yl)-acetic acid methyl ester.

Step 3: The ester from Step 2 was hydrolyzed to the acid as described in Example 8, Step 7.

Example 17

Synthesis of (5-{2-[(N-Benzyl-N-cyclopropanecarbonyl-amino)-methyl]-4-trifluoromethyl-phenyl}-pyridin-3-yl)-acetic acid (Compound 17)

Step 1: 2-Bromo-5-(trifluoromethyl)benzaldehyde (3 g, 11.9 mmol), benzylamine (1.94 mL, 17.8 mmol), and sodium cyanoborohydride (1.12 g, 17.8 mmol) were combined in MeOH (30 mL). Acetic acid (1.02 mL, 17.8 mmol) was added, and the reaction was stirred at room temperature for 2 hours. The mixture was concentrated, and the residue was partitioned between CH₂Cl₂ and H₂O. The aqueous layer was separated and extracted twice with CH₂Cl₂, and the combined organic layers were dried, concentrated, and purified by silica gel chromatography (10-40% EtOAc in hexanes) to give benzyl-(2-bromo-5-trifluoromethyl-benzyl)-amine.

Step 2: Benzyl-(2-bromo-5-trifluoromethyl-benzyl)-amine and cyclopropanecarbonyl chloride were reacted as described in Example 11, Step 2 to provide cyclopropanecarboxylic acid benzyl-(2-bromo-5-trifluoromethyl-benzyl)-amide.

Step 3: Cyclopropanecarboxylic acid benzyl-(2-bromo-5-trifluoromethyl-benzyl)-amide and bis(pinacolato)diboron were reacted as described in Example 11, Step 3 to provide cyclopropanecarboxylic acid benzyl-[2-(4,4,5,5-tetramethyl-[1,3,2]dioxaborolan-2-yl)-5-trifluoromethyl-benzyl]-amide.

Step 4: Cyclopropanecarboxylic acid benzyl-[2-(4,4,5,5-tetramethyl-[1,3,2]dioxaborolan-2-yl)-5-trifluoromethyl-benzyl]-amide (60% pure; 1.07 g, 1.4 mmol), (5-bromo-pyridin-3-yl)-acetic acid ethyl ester (0.375 g, 1.5 mmol), and potassium carbonate (0.484 g, 3.5 mmol) were combined in DME (8 mL) and H₂O (4 mL), and the solution was purged with N₂ for 15 minutes. Tetrakis(triphenylphosphine)palladium(0) (0.162 g, 0.14 mmol) was added, and the reaction was stirred at 90° C. overnight. The mixture was diluted with saturated aqueous NH₄Cl and EtOAc. The aqueous layer was separated and extracted twice with EtOAc, and the combined organic layers were dried and concentrated. The residue was purified by preparative HPLC to give (5-{2-[(N-benzyl-N-cyclopropanecarbonyl-amino)-methyl]-4-trifluoromethyl-phenyl}-pyridin-3-yl)-acetic acid ethyl ester, which was then hydrolyzed in the following step, as well as the hydrolyzed product.

Step 5: To (5-{2-[(N-benzyl-N-cyclopropanecarbonyl-amino)-methyl]-4-trifluoromethyl-phenyl}-pyridin-3-yl)-acetic acid ethyl ester (0.043 g, 0.09 mmol) in THF (3 mL) and MeOH (0.3 mL) was added 1N aqueous LiOH (3 mL), and the reaction was stirred at room temperature. The mixture was neutralized with 1N aqueous HCl to pH 4-5 and extracted three times with EtOAc. The combined organic layers were dried and concentrated, and the residue was purified by preparative HPLC to give Compound 17.

Example 18

Synthesis of (5-{2-[(N-Acetyl-N-benzyl-amino)-methyl]-4-trifluoromethyl-phenyl}-pyridin-3-yl)-acetic acid (Compound 18)

Step 1: Benzyl-(2-bromo-5-trifluoromethyl-benzyl)-amine and acetyl chloride were reacted as described in Example 11, Step 2 to provide N-benzyl-N-(2-bromo-5-trifluoromethyl-benzyl)-acetamide.

Step 2: N-Benzyl-N-(2-bromo-5-trifluoromethyl-benzyl)-acetamide and bis(pinacolato)diboron were reacted as described in Example 11, Step 3 to provide N-benzyl-N-[2-(4,4,5,5-tetramethyl-[1,3,2]dioxaborolan-2-yl)-5-trifluoromethyl-benzyl]-acetamide.

Step 3: N-Benzyl-N-[2-(4,4,5,5-tetramethyl-[1,3,2]dioxaborolan-2-yl)-5-trifluoromethyl-benzyl]-acetamide and (5-bromo-pyridin-3-yl)-acetic acid ethyl ester were reacted as described in Example 17, Step 4 and the product was hydrolyzed to the acid as described in Example 17, Step 5.

Example 19

Synthesis of (5-{2-[(N-Acetyl-N-benzyl-amino)-methyl]-4-trifluoromethyl-phenyl}-6-chloro-pyridin-3-yl)-acetic acid (Compound 19)

Step 1: (5-{2-[(N-Acetyl-N-benzyl-amino)-methyl]-4-trifluoromethyl-phenyl}-pyridin-3-yl)-acetic acid ethyl ester was reacted as described in Example 9, Step 1 to provide (5-{2-[(N-acetyl-N-benzyl-amino)-methyl]-4-trifluoromethyl-phenyl}-1-oxy-pyridin-3-yl)-acetic acid ethyl ester.

Step 2: (5-{2-[(N-Acetyl-N-benzyl-amino)-methyl]-4-trifluoromethyl-phenyl}-1-oxy-pyridin-3-yl)-acetic acid ethyl ester was reacted as described in Example 9, Step 2 to provide (5-{2-[(N-acetyl-N-benzyl-amino)-methyl]-4-trifluoromethyl-phenyl}-6-chloro-pyridin-3-yl)-acetic acid ethyl ester and (5-{2-[(N-acetyl-N-benzyl-amino)-methyl]-4-trifluoromethyl-phenyl}-2-chloro-pyridin-3-yl)-acetic acid ethyl ester.

Step 3: The mixture of compounds from Step 2 was hydrolyzed as described in Example 17, Step 5 to provide Compound 19.

Example 20

Synthesis of (5-{2-[(N-Acetyl-N-benzyl-amino)-methyl]-4-trifluoromethyl-phenyl}-2-chloro-pyridin-3-yl)-acetic acid (Compound 20)

Prepared according to the procedure described in Example 17, Step 5, using the following starting material: a mixture of (5-{2-[(N-acetyl-N-benzyl-amino)-methyl]-4-trifluoromethyl-phenyl}-6-chloro-pyridin-3-yl)-acetic acid ethyl ester and (5-{2-[(N-acetyl-N-benzyl-amino)-methyl]-4-trifluoromethyl-phenyl}-2-chloro-pyridin-3-yl)-acetic acid ethyl ester.

Example 21

Synthesis of (5-{2-[(N-Cyclopropanecarbonyl-N-ethyl-amino)-methyl]-4-methylsulfanyl-phenyl}-pyridin-3-yl)-acetic acid (Compound 21) and (5-{2-[(N-Cyclopropanecarbonyl-N-ethyl-amino)-methyl]-4-mercapto-phenyl}-pyridin-3-yl)-acetic acid (Compound 24)

Step 1: (5-Bromo-pyridin-3-yl)-acetic acid ethyl ester (1.91 g, 7.8 mmol), 5-fluoro-2-(4,4,5,5-tetramethyl-[1,3,2]dioxaborolan-2-yl)-benzaldehyde (50% pure; 2.94 g, 11.75 mmol), and potassium carbonate (3.25 g, 23.5 mmol) were combined in 2:1 DME:$H_2O$, and the solution was purged with $N_2$ for 20 minutes. Tetrakis(triphenylphosphine)palladium(0) (0.45 g, 0.39 mmol) was added, and the reaction was purged with $N_2$ for another 25 minutes and then stirred at 75° C. for 2 hours. The mixture was worked up with EtOAc and $H_2O$, and the residue was purified by silica gel chromatography (0-100% EtOAc in hexanes) to give [5-(4-fluoro-2-formyl-phenyl)-pyridin-3-yl]-acetic acid ethyl ester.

Step 2: To [5-(4-fluoro-2-formyl-phenyl)-pyridin-3-yl]-acetic acid ethyl ester (1.2 g, 4.18 mmol) in MeOH was added sodium cyanoborohydride (0.394 g, 6.26 mmol) and ethylamine (2M in THF; 3.13 mL, 6.26 mmol). Acetic acid (0.36 mL, 6.26 mmol) was added, and the reaction was stirred for 2 hours at room temperature. The mixture was concentrated, and the residue was dissolved in $CH_2Cl_2$ and washed with saturated aqueous $NaHCO_3$ and $H_2O$. The organic layer was dried over $Na_2SO_4$, filtered, and concentrated, and the residue was purified by silica gel chromatography (0-10% MeOH in $CH_2Cl_2$) to give [5-(2-ethylaminomethyl-4-fluoro-phenyl)-pyridin-3-yl]-acetic acid ethyl ester.

Step 3: [5-(2-Ethylaminomethyl-4-fluoro-phenyl)-pyridin-3-yl]-acetic acid ethyl ester and cyclopropanecarboxylic acid were reacted as described in Example 8, Step 6 to provide (5-{2-[(N-cyclopropanecarbonyl-N-ethyl-amino)-methyl]-4-fluoro-phenyl}-pyridin-3-yl)-acetic acid ethyl ester.

Step 4: (5-{2-[(N-Cyclopropanecarbonyl-N-ethyl-amino)-methyl]-4-fluoro-phenyl}-pyridin-3-yl)-acetic acid ethyl ester (0.154 g, 0.42 mmol) and sodium thiomethoxide (0.067 g, 0.95 mmol) were combined in DMF (4.2 mL), and the reaction was stirred at 100° C. overnight. Analytical LCMS indicated that the ester hydrolyzed during the reaction, and that some of the thiomethoxy group was demethylated. The mixture was diluted with $H_2O$, acidified with 2N aqueous HCl to pH 4, and extracted with EtOAc. The combined organic layers were concentrated, and then dissolved in $CH_2Cl_2$ and concentrated. The residue was purified by preparative HPLC to give Compound 21 and Compound 24 as separated products.

Example 22

Synthesis of (5-{4-tert-Butylsulfanyl-2-[(N-cyclopropanecarbonyl-N-ethyl-amino)-methyl]-phenyl}-pyridin-3-yl)-acetic acid (Compound 22)

Sodium hydride (60% in mineral oil; 0.042 g, 1.04 mmol) was suspended in DMF (5 mL). After stirring for 10 minutes, 2-methyl-2-propanethiol (0.13 mL, 1.15 mmol) was added, and the mixture was stirred for 30 minutes. (5-{2-[(N-Cyclopropanecarbonyl-N-ethyl-amino)-methyl]-4-fluoro-phenyl}-pyridin-3-yl)-acetic acid ethyl ester (0.20 g, 0.52 mmol) was added, and the reaction was stirred at 90° C. overnight. The mixture was diluted with $H_2O$, and $N_2$ was bubbled through the solution into a bleach trap until all odor was removed. The aqueous layer was washed with EtOAc, and then acidified to pH 4 and extracted with EtOAc. The combined organic layers were concentrated, and the residue was purified by preparative HPLC to give Compound 22.

Example 23

Synthesis of (5-{2-[(N-Cyclopropanecarbonyl-N-ethyl-amino)-methyl]-4-fluoro-phenyl}-pyridin-3-yl)-acetic acid (Compound 23)

(5-{2-[(N-Cyclopropanecarbonyl-N-ethyl-amino)-methyl]-4-fluoro-phenyl}-pyridin-3-yl)-acetic acid ethyl ester (0.202 g, 0.53 mmol) was dissolved in THF (5.25 mL) and treated with 1N aqueous LiOH (2.63 mL, 2.63 mmol) and a small amount of MeOH. The reaction was stirred at 35° C. for 30 minutes. The mixture was concentrated, and the residue was diluted with $H_2O$ and washed with EtOAc. The aqueous layer was acidified with 1N aqueous HCl to pH 6 and extracted with EtOAc, and the combined organic layers were washed with H₂O and brine, and then dried over Na₂SO₄, filtered, and concentrated to give Compound 23.

Example 24

Synthesis of [5-(2-{[N-Ethyl-N-(3-phenyl-propionyl)-amino]-methyl}-4-trifluoromethyl-phenyl)-pyridin-3-yl]-acetic acid (Compound 25)

Step 1: Ethyl-[2-(4,4,5,5-tetramethyl-[1,3,2]dioxaborolan-2-yl)-5-trifluoromethyl-benzyl]-carbamic acid tert-butyl ester and (5-bromo-pyridin-3-yl)-acetic acid ethyl ester were reacted as described in Example 8, Step 4 to provide (5-{2-[(N-tert-butoxycarbonyl-N-ethyl-amino)-methyl]-4-trifluoromethyl-phenyl}-pyridin-3-yl)-acetic acid ethyl ester.

Step 2: (5-{2-[(N-tert-Butoxycarbonyl-N-ethyl-amino)-methyl]-4-trifluoromethyl-phenyl}-pyridin-3-yl)-acetic acid ethyl ester was reacted as described in Example 8, Step 5 to provide [5-(2-ethylaminomethyl-4-trifluoromethyl-phenyl)-pyridin-3-yl]-acetic acid ethyl ester, dihydrochloride.

Step 3: [5-(2-Ethylaminomethyl-4-trifluoromethyl-phenyl)-pyridin-3-yl]-acetic acid ethyl ester, dihydrochloride and hydrocinnamic acid were reacted as described in Example 8, Step 6 to provide [5-(2-{[N-ethyl-N-(3-phenyl-propionyl)-amino]-methyl}-4-trifluoromethyl-phenyl)-pyridin-3-yl]-acetic acid ethyl ester.

Step 4: The ester from Step 3 was hydrolyzed to the acid as described in Example 12, Step 4.

Example 25

Synthesis of (5-{2-[(N-Acetyl-N-benzyl-amino)-methyl]-4-trifluoromethyl-phenyl}-6-hydroxy-pyridin-3-yl)-acetic acid (Compound 26)

Step 1: 2-(5-Bromo-2-methoxy-pyridin-3-yl)-5-trifluoromethyl-benzaldehyde and benzylamine were reacted as described in Example 17, Step 1 to provide benzyl-[2-(5-bromo-2-methoxy-pyridin-3-yl)-5-trifluoromethyl-benzyl]-amine.

Step 2: Benzyl-[2-(5-bromo-2-methoxy-pyridin-3-yl)-5-trifluoromethyl-benzyl]-amine and acetyl chloride were reacted as described in Example 11, Step 2 to provide N-benzyl-N-[2-(5-bromo-2-methoxy-pyridin-3-yl)-5-trifluoromethyl-benzyl]-acetamide.

Step 3: N-Benzyl-N-[2-(5-bromo-2-methoxy-pyridin-3-yl)-5-trifluoromethyl-benzyl]-acetamide (0.288 g, 0.58 mmol), (trimethylsilyl)acetylene (0.08 mL, 0.58 mmol), and copper iodide (0.011 g, 0.06 mmol) were combined in triethylamine (3.5 mL), and the solution was purged with N₂ for 25 minutes. Dichlorobis(triphenylphosphine)palladium(II) (0.042 g, 0.06 mmol) was added, and the reaction was stirred at room temperature overnight. A few drops of DMF was added, and the reaction was stirred at 50° C. for 5 hours, and at 60° C. for 3 hours. The mixture was worked-up with CH₂Cl₂ and H₂O, and the combined organic layers were dried, filtered, and concentrated. The residue was purified by silica gel chromatography (0-30% EtOAc in hexanes) to give N-benzyl-N-[2-(2-methoxy-5-trimethylsilanylethynyl-pyridin-3-yl)-5-trifluoromethyl-benzyl]-acetamide.

Step 4: To cyclohexene (0.12 mL, 1.14 mmol) in THF (0.3 mL) at 0° C. was added borane tetrahydrofuran complex (1M in THF; 0.53 mL, 0.53 mmol), and the reaction was stirred for 1.5 hours. N-Benzyl-N-[2-(2-methoxy-5-trimethylsilanylethynyl-pyridin-3-yl)-5-trifluoromethyl-benzyl]-acetamide (0.084 g, 0.15 mmol) in THF (2 mL) was added dropwise, and the reaction was stirred for 1 hour at room temperature. The mixture was cooled to 0° C., and MeOH (0.9 mL) was added, followed by 1N aqueous NaOH (0.53 mL, 0.53 mmol) and hydrogen peroxide (30%; 0.16 mL, 1.55 mmol), and the reaction was stirred for 1 hour at 0° C. and 1.5 hours at 40° C. The mixture was acidified with 1N aqueous HCl and extracted with EtOAc to give N-Benzyl-N-[2-(5-ethynyl-2-methoxy-pyridin-3-yl)-5-trifluoromethyl-benzyl]-acetamide.

Step 5: To cyclohexene (0.20 mL, 1.98 mmol) at room temperature was added borane tetrahydrofuran complex (1M in THF; 1.01 mL, 1.01 mmol), and the reaction was stirred for 45 minutes. N-Benzyl-N-[2-(5-ethynyl-2-methoxy-pyridin-3-yl)-5-trifluoromethyl-benzyl]-acetamide (0.126 g, 0.29 mmol) in THF (2 mL) was added dropwise, and the reaction was stirred for 2 hours at room temperature. The mixture was cooled to 0° C., and MeOH (1 mL) and 1N aqueous NaOH (1.01 mL, 1.01 mmol) were added, followed by hydrogen peroxide (30%; 0.31 mL, 3.00 mmol), and the reaction was stirred for 1 hour at 0° C. The mixture was acidified with 1N aqueous HCl and extracted with EtOAc, and the combined organic layers were dried, filtered, and concentrated. The residue was purified by preparative HPLC to give (5-{2-[(N-Acetyl-N-benzyl-amino)-methyl]-4-trifluoromethyl-phenyl}-6-hydroxy-pyridin-3-yl)-acetic acid.

Example 26

Synthesis of {5-[2-(3-Benzyl-1-ethyl-ureidomethyl)-4-trifluoromethyl-phenyl]-6-methoxy-pyridin-3-yl}-acetic acid (Compound 27)

Step 1: 3-Bromo-2-hydroxy-5-methylpyridine (5.012 g, 26.7 mmol), silver carbonate (9.58 g, 34.7 mmol), and iodomethane (5 mL, 80.0 mmol) were combined in CHCl₃ (75 mL) and stirred at 55° C. for 3 hours. The mixture was cooled and filtered through Celite, and the filtrate was concentrated and purified by silica gel chromatography (0-100% EtOAc in hexanes) to give 3-bromo-2-methoxy-5-methyl-pyridine.

Step 2: 3-Bromo-2-methoxy-5-methyl-pyridine (4.0 g, 19.8 mmol), N-bromosuccinimide (4.45 g, 23.8 mmol), and azobisisobutyronitrile (0.163 g, 0.99 mmol) were combined in benzene (40 mL) and stirred overnight at 80° C. The reaction was stirred for another 24 hours at 80° C., and then additional N-bromosuccinimide (1.8 g, 10.1 mmol), and azobisisobutyronitrile (catalytic) were added. After stirring for another 2 hours at 80° C., the mixture was diluted with H₂O and extracted with CH₂Cl₂. The residue was purified by silica gel chromatography to give 3-bromo-5-bromomethyl-2-methoxy-pyridine.

Step 3: 3-Bromo-5-bromomethyl-2-methoxy-pyridine (6.03 g, 21.5 mmol), N-bromosuccinimide (4.09 g, 23.0 mmol), and azobisisobutyronitrile (one scoop) were combined in benzene (40 mL) and stirred at 80° C. for 4 hours. After cooling, the mixture was diluted with H₂O and extracted with EtOAc. The combined organic layers were dried over MgSO₄, filtered, and concentrated to give 3-Bromo-5-dibromomethyl-2-methoxy-pyridine.

Step 4: To 3-bromo-5-dibromomethyl-2-methoxy-pyridine (7.1 g, 19.7 mmol) in EtOH (200 mL) was added silver nitrate (8.38 g, 49.3 mmol) in H₂O (40 mL) slowly, and the reaction was stirred at 75° C. overnight. The mixture was cooled, diluted with brine, filtered, and concentrated. 1,4-Dioxane (70 mL) and 1N aqueous HCl (70 mL) was added, and the reaction was stirred overnight. The mixture was neutralized and extracted with EtOAc, and the combined organic layers were dried, filtered, and concentrated. The residue was purified by silica gel chromatography to give 5-bromo-6-methoxy-pyridine-3-carbaldehyde and 5-bromo-6-methoxy-nicotinic acid ethyl ester, which were combined and reduced together in the next step.

Step 5: A mixture of 5-bromo-6-methoxy-pyridine-3-carbaldehyde and 5-bromo-6-methoxy-nicotinic acid ethyl ester (3 g, 13.9 mmol) was dissolved in THF (30 mL) and cooled to 0° C., and lithium triethylborohydride (1M in THF; 42 mL, 42 mmol) was added. The reaction was stirred for 5 minutes, and then quenched with EtOH, acidified with 1N aqueous HCl, and extracted with EtOAc. The combined organic layers were dried over $MgSO_4$, filtered, and concentrated to give (5-bromo-6-methoxy-pyridin-3-yl)-methanol.

Step 6: To (5-bromo-6-methoxy-pyridin-3-yl)-methanol (2.86 g, 13.1 mmol) in DME (30 mL) was added phosphorus tribromide (1.9 mL, 19.7 mmol), and the reaction was stirred for 15 minutes. The mixture was worked up with EtOAc and saturated aqueous $NaHCO_3$, and the combined organic layers were dried over $MgSO_4$, filtered, and concentrated to give 3-bromo-5-bromomethyl-2-methoxy-pyridine.

Step 7: To 3-bromo-5-bromomethyl-2-methoxy-pyridine (1.42 g, 5.05 mmol) in EtOH (14 mL) and $H_2O$ (1.5 mL) was added sodium cyanide (0.25 g, 5.05 mmol), and the reaction was stirred at 50° C. overnight. The mixture was cooled to room temperature and worked up with $CH_2Cl_2$ and saturated aqueous $NaHCO_3$. The combined organic layers were dried, filtered, and concentrated to give (5-bromo-6-methoxy-pyridin-3-yl)-acetonitrile.

Step 8: To (5-bromo-6-methoxy-pyridin-3-yl)-acetonitrile (1.139 g, 5.02 mmol) in EtOH (11 ml) was added acetyl chloride (3.6 mL, 50.54 mmol), and the reaction was stirred at 50° C. for 24 hours, and at room temperature for 2 days. The reaction was worked up with $CH_2Cl_2$ and saturated aqueous $NaHCO_3$, and then reacidified and extracted with $CH_2Cl_2$. The combined organic layers were dried, filtered, and concentrated to give (5-bromo-6-methoxy-pyridin-3-yl)-acetic acid ethyl ester.

Step 9: (5-Bromo-6-methoxy-pyridin-3-yl)-acetic acid ethyl ester (5.02 mmol) was dissolved in $CHCl_3$ (17 mL). Silver carbonate (1.58 g, 5.7 mmol) and iodomethane (0.82 mL, 13.14 mmol) were added, and the reaction was stirred at 55° C. for 2.5 hours. The mixture was filtered through Celite, and the filtrate was concentrated and purified by silica gel chromatography (0-60% EtOAc in hexanes) to give (5-bromo-6-hydroxy-pyridin-3-yl)-acetic acid ethyl ester.

Step 10: To (2-bromo-5-trifluoromethyl-benzyl)-ethylamine (2.35 g, 8.33 mmol) in $CH_2Cl_2$ (24 mL) was added triethylamine (1.8 mL, 12.5 mmol), followed by benzyl isocyanate (1.22 mL, 10.0 mmol), and the reaction was stirred at room temperature for 50 minutes. The mixture was worked up with $CH_2Cl_2$ and $H_2O$, and the combined organic layers were dried, filtered, and concentrated. The residue was dissolved in $CH_2Cl_2$ and filtered to remove solids, and the filtrate was purified by silica gel chromatography to give 3-benzyl-1-(2-bromo-5-trifluoromethyl-benzyl)-1-ethyl-urea.

Step 11: 3-Benzyl-1-(2-bromo-5-trifluoromethyl-benzyl)-1-ethyl-urea and bis(pinacolato)diboron were reacted as described in Example 11, Step 3 to provide 3-benzyl-1-ethyl-1-[2-(4,4,5,5-tetramethyl-[1,3,2]dioxaborolan-2-yl)-5-trifluoromethyl-benzyl]-urea.

Step 12: 3-Benzyl-1-ethyl-1-[2-(4,4,5,5-tetramethyl-[1,3,2]dioxaborolan-2-yl)-5-trifluoromethyl-benzyl]-urea and (5-bromo-6-methoxy-pyridin-3-yl)-acetic acid ethyl ester were reacted as described in Example 11, Step 4 to provide {5-[2-(3-benzyl-1-ethyl-ureidomethyl)-4-trifluoromethyl-phenyl]-6-methoxy-pyridin-3-yl}-acetic acid ethyl ester.

Step 13: The ester from Step 12 was hydrolyzed to the acid as described in Example 8, Step 7.

Example 27

Synthesis of (5-{2-[(N-Acetyl-N-benzyl-amino)-methyl]-4-trifluoromethyl-phenyl}-6-methoxy-pyridin-3-yl)-acetic acid (Compound 28)

Prepared according to the procedure described in Example 17, Step 4 and Step 5, using the following starting materials: N-benzyl-N-[2-(4,4,5,5-tetramethyl-[1,3,2]dioxaborolan-2-yl)-5-trifluoromethyl-benzyl]-acetamide and (5-bromo-6-methoxy-pyridin-3-yl)-acetic acid ethyl ester.

Example 28

Synthesis of [5-(2-{[N-Ethyl-N-(pyrazine-2-carbonyl)-amino]-methyl}-4-trifluoromethyl-phenyl)-pyridin-3-yl]-acetic acid (Compound 29)

Step 1: Ethyl-[2-(4,4,5,5-tetramethyl-[1,3,2]dioxaborolan-2-yl)-5-trifluoromethyl-benzyl]-carbamic acid tert-butyl ester and (5-bromo-pyridin-3-yl)-acetic acid ethyl ester were reacted as described in Example 11, Step 4 (5-{2-[(N-tert-butoxycarbonyl-N-ethyl-amino)-methyl]-4-trifluoromethyl-phenyl}-pyridin-3-yl)-acetic acid ethyl ester.

Step 2: To (5-{2-[(N-tert-butoxycarbonyl-N-ethyl-amino)-methyl]-4-trifluoromethyl-phenyl}-pyridin-3-yl)-acetic acid ethyl ester (0.375 g, 0.8 mmol) in EtOAc (4 mL) was added 4N HCl in 1,4-dioxane (0.8 mL), and the reaction was stirred at 50° C. for 1 hour. Additional 4N HCl in 1,4-dioxane (0.8 mL) was added, and the reaction was stirred for 1 hour at 70° C. The mixture was concentrated to give [5-(2-ethylaminomethyl-4-trifluoromethyl-phenyl)-pyridin-3-yl]-acetic acid ethyl ester, dihydrochloride.

Step 3: [5-(2-Ethylaminomethyl-4-trifluoromethyl-phenyl)-pyridin-3-yl]-acetic acid ethyl ester, dihydrochloride and pyrazinecarboxylic acid were reacted as described in Example 8, Step 6 to provide [5-(2-{[N-ethyl-N-(pyrazine-2-carbonyl)-amino]-methyl}-4-trifluoromethyl-phenyl)-pyridin-3-yl]-acetic acid ethyl ester.

Step 4: The ester from Step 3 was hydrolyzed to the acid as described in Example 8, Step 7.

Example 29

Synthesis of [5-(2-{[N-(2,4-Dimethoxy-pyrimidine-5-carbonyl)-N-ethyl-amino]-methyl}-4-trifluoromethyl-phenyl)-pyridin-3-yl]-acetic acid (Compound 30)

[5-(2-Ethylaminomethyl-4-trifluoromethyl-phenyl)-pyridin-3-yl]-acetic acid ethyl ester, dihydrochloride and 2,4-dimethoxypyrimidine-6-carboxylic acid were reacted as described in Example 8, Step 6 to provide [5-(2-{[N-(2,6-dimethoxy-pyrimidine-4-carbonyl)-N-ethyl-amino]-methyl}-4-trifluoromethyl-phenyl)-pyridin-3-yl]-acetic acid ethyl ester. The ester was hydrolyzed to the acid as described in Example 8, Step 7.

Example 30

Synthesis of {5-[2-({N-[2-(6-Chloro-pyridin-3-yl)-acetyl]-N-ethyl-amino}-methyl)-4-trifluoromethyl-phenyl]-pyridin-3-yl}-acetic acid (Compound 31)

Step 1: [5-(2-Ethylaminomethyl-4-trifluoromethyl-phenyl)-pyridin-3-yl]-acetic acid ethyl ester, dihydrochloride and 2-chloropyridine-5-acetic acid were reacted as described in Example 8, Step 6 to provide {5-[2-({N-[2-(6-chloro-pyridin-3-yl)-acetyl]-N-ethyl-amino}-methyl)-4-trifluoromethyl-phenyl]-pyridin-3-yl}-acetic acid ethyl ester.

Step 2: To {5-[2-({N-[2-(6-chloro-pyridin-3-yl)-acetyl]-N-ethyl-amino}-methyl)-4-trifluoromethyl-phenyl]-pyridin-3-yl}-acetic acid ethyl ester (0.085 g, 0.16 mmol) in THF (2 mL) was added 1N aqueous LiOH (2 mL), and the reaction was stirred at 50° C. The mixture was neutralized with 1N aqueous HCl to pH 3-4 and extracted three times with EtOAc. The combined organic layers were dried and concentrated to give Compound 31.

Example 31

Synthesis of {5-[2-({N-[2-(4,6-Diethoxy-pyrimidin-2-yl)-acetyl]-N-ethyl-amino}-methyl)-4-trifluoromethyl-phenyl]-pyridin-3-yl}-acetic acid (Compound 32)

Step 1: Diethyl malonate and malonamamidine hydrochloride were combined in EtOH (50 mL) with stirring. Sodium ethoxide was added dropwise via addition funnel over 10 minutes. The reaction was stirred overnight at room temperature to give 2-(4,6-dihydroxy-pyrimidin-2-yl)-acetamide.

Step 2: N,N-Diethylaniline (1.51 mL, 0.95 mmol) was added carefully to a slurry of (2-(4,6-dihydroxy-pyrimidin-2-yl)-acetamide (1.0 g, 0.59 mmol) in phosphorus oxychloride (3.0 mL, 32.54 mmol) through a reflux condenser. The reaction was heated for 10 minutes and then poured onto ice (50 mL) and extracted twice with EtOAc. The combined organic layers were washed with saturated aqueous NaHCO$_3$, H$_2$O, and brine, and then dried over Na$_2$SO$_4$, filtered, and concentrated. The residue was purified by silica gel chromatography (0-100% EtOAc in hexanes) to give (4,6-dichloropyrimidin-2-yl)-acetonitrile.

Step 3: Acetyl chloride (15.12 mL, 212.8 mmol) was slowly added to EtOH (50 mL) at 0° C. (4,6-Dichloro-pyrimidin-2-yl)-acetonitrile (2.0 g, 10.6 mmol) was then added to this solution, and the reaction was stirred at 60° C. for 12 hours. The mixture was diluted with H$_2$O and extracted with EtOAc. The combined organic layers were washed with saturated aqueous NaHCO$_3$ and brine, and then dried over Na$_2$SO$_4$, decanted, and concentrated to give a mixture of (4-chloro-6-ethoxy-pyrimidin-2-yl)-acetic acid ethyl ester and (4,6-diethoxy-pyrimidin-2-yl)-acetic acid ethyl ester.

Step 4: To (4,6-diethoxy-pyrimidin-2-yl)-acetic acid ethyl ester (0.218 g, 0.86 mmol) in THF (3 mL) was added 1N aqueous LiOH (2.58 mL, 2.58 mmol), and the reaction was stirred at 50° C. for 1 hour, and then at room temperature overnight. The mixture was acidified with 1N aqueous HCl and extracted three times with EtOAc. The combined organic layers were dried, filtered, and concentrated to give (4,6-diethoxy-pyrimidin-2-yl)-acetic acid.

Step 5: [5-(2-Ethylaminomethyl-4-trifluoromethyl-phenyl)-pyridin-3-yl]-acetic acid ethyl ester, dihydrochloride and (4,6-diethoxy-pyrimidin-2-yl)-acetic acid were reacted as described in Example 8, Step 6 to provide {5-[2-({N-[2-(4,6-diethoxy-pyrimidin-2-yl)-acetyl]-N-ethyl-amino}-methyl)-4-trifluoromethyl-phenyl]-pyridin-3-yl}-acetic acid ethyl ester.

Step 6: The ester from Step 5 was hydrolyzed to the acid as described in Example 30, Step 2.

Example 32

Synthesis of [5-(2-{[N-Ethyl-N-(2-pyridin-2-yl-acetyl)-amino]-methyl}-4-trifluoromethyl-phenyl)-pyridin-3-yl]-acetic acid (Compound 33)

[5-(2-ethylaminomethyl-4-trifluoromethyl-phenyl)-pyridin-3-yl]-acetic acid ethyl ester and 2-pyridylacetic acid hydrochloride were reacted as described in Example 8, Step 6 to provide [5-(2-{[N-ethyl-N-(2-pyridin-2-yl-acetyl)-amino]-methyl}-4-trifluoromethyl-phenyl)-pyridin-3-yl]-acetic acid ethyl ester. The ester was hydrolyzed to the acid as described in Example 30, Step 2.

Example 33

Synthesis of [5-(2-{[N-Ethyl-N-(2-methoxy-acetyl)-amino]-methyl}-4-trifluoromethyl-phenyl)-pyridin-3-yl]-acetic acid (Compound 34)

[5-(2-Ethylaminomethyl-4-trifluoromethyl-phenyl)-pyridin-3-yl]-acetic acid ethyl ester and methoxyacetic acid were reacted as described in Example 8, Step 6 to provide [5-(2-{[N-ethyl-N-(2-methoxy-acetyl)-amino]-methyl}-4-trifluoromethyl-phenyl)-pyridin-3-yl]-acetic acid ethyl ester. The ester was hydrolyzed to the acid as described in Example 30, Step 2.

Example 34

Synthesis of [5-(2-{[N-(2-Ethoxy-acetyl)-N-ethyl-amino]-methyl}-4-trifluoromethyl-phenyl)-pyridin-3-yl]-acetic acid (Compound 35)

[5-(2-ethylaminomethyl-4-trifluoromethyl-phenyl)-pyridin-3-yl]-acetic acid ethyl ester and ethoxyacetic acid were reacted as described in Example 8, Step 6 to provide [5-(2-{[N-(2-ethoxy-acetyl)-N-ethyl-amino]-methyl}-4-trifluoromethyl-phenyl)-pyridin-3-yl]-acetic acid ethyl ester. The ester was hydrolyzed to the acid as described in Example 30, Step 2.

Example 35

Synthesis of [5-(2-{[N-Ethyl-N-(3-pyridin-3-yl-propionyl)-amino]-methyl}-4-trifluoromethyl-phenyl)-pyridin-3-yl]-acetic acid (Compound 36)

[5-(2-Ethylaminomethyl-4-trifluoromethyl-phenyl)-pyridin-3-yl]-acetic acid ethyl ester and 3-pyridinepropionic acid were reacted as described in Example 8, Step 6 to provide [5-(2-{[N-ethyl-N-(3-pyridin-3-yl-propionyl)-amino]-methyl}-4-trifluoromethyl-phenyl)-pyridin-3-yl]-acetic acid ethyl ester. The ester was hydrolyzed to the acid as described in Example 30, Step 2.

Example 36

Synthesis of (5-{2-[(N-Cyclopropanecarbonyl-N-ethyl-amino)-methyl]-4-trifluoromethyl-phenyl}-6-hydroxy-pyridin-3-yl)-acetic acid (Compound 38)

To a solution of (5-{2-[(cyclopropanecarbonyl-ethyl-amino)-methyl]-4-trifluoromethyl-phenyl}-6-methoxy-pyridin-3-yl)-acetic acid (0.099 g, 0.22 mmol) in EtOH (1 mL) was added thionyl chloride (0.16 mL, 2.19 mmol), and the reaction was stirred at 80° C. overnight. The mixture was diluted with CH₂Cl₂ and H₂O, and the aqueous layer was extracted with CH₂Cl₂. The combined organic layers were dried over MgSO₄, filtered, and concentrated to give (5-{2-[(N-cyclopropanecarbonyl-N-ethyl-amino)-methyl]-4-trifluoromethyl-phenyl}-6-hydroxy-pyridin-3-yl)-acetic acid ethyl ester. The ester was hydrolyzed to the acid as described in Example 3, Step 7.

Example 37

Synthesis of [5-{2-[(N-Cyclopropanecarbonyl-N-ethyl-amino)-methyl]-4-trifluoromethyl-phenyl}-6-(2,2,2-trifluoro-ethoxy)-pyridin-3-yl]-acetic acid (Compound 39)

(5-{2-[(N-Cyclopropanecarbonyl-N-ethyl-amino)-methyl]-4-trifluoromethyl-phenyl}-6-hydroxy-pyridin-3-yl)-acetic acid ethyl ester (0.175 g, 0.39 mmol), 2,2,2-trifluoro-ethyl tosylate (0.151 g, 0.58 mmol), and potassium carbonate (0.070 g, 0.51 mmol) were combined in DMF (1.8 mL) and stirred at 55° C. overnight. Additional 2,2,2-trifluoroethyl tosylate and potassium carbonate were added, and the reaction was stirred at 75° C. overnight. After cooling, the crude material was used directly in the hydrolysis step. The ester was hydrolyzed to the acid as described in Example 3, Step 7. The acid was purified by preparative HPLC.

Example 38

Synthesis of (5-{2-[(N-Benzyloxycarbonyl-N-ethyl-amino)-methyl]-4-trifluoromethyl-phenyl}-6-methoxy-pyridin-3-yl)-acetic acid (Compound 40)

Step 1: (2-Bromo-5-trifluoromethyl-benzyl)-ethyl-amine and benzyl chloroformate were reacted as described in Example 5, Step 4 to provide (2-bromo-5-trifluoromethyl-benzyl)-ethyl-carbamic acid benzyl ester.
Step 2: (2-Bromo-5-trifluoromethyl-benzyl)-ethyl-carbamic acid benzyl ester and bis(pinacolato)diboron were reacted as described in Example 1, Step 8 to provide ethyl-[2-(4,4,5,5-tetramethyl-[1,3,2]dioxaborolan-2-yl)-5-trifluoromethyl-benzyl]-carbamic acid benzyl ester.
Step 3: Ethyl-[2-(4,4,5,5-tetramethyl-[1,3,2]dioxaborolan-2-yl)-5-trifluoromethyl-benzyl]-carbamic acid benzyl ester and (5-bromo-6-methoxy-pyridin-3-yl)-acetic acid ethyl ester were reacted as described in Example 3, Step 6 to provide (5-{2-[(N-benzyloxycarbonyl-N-ethyl-amino)-methyl]-4-trifluoromethyl-phenyl}-6-methoxy-pyridin-3-yl)-acetic acid ethyl ester.
Step 4: (5-{2-[(N-Benzyloxycarbonyl-N-ethyl-amino)-methyl]-4-trifluoromethyl-phenyl}-6-methoxy-pyridin-3-yl)-acetic acid ethyl ester was hydrolyzed to the acid as described in Example 3, Step 7.

Example 39

Synthesis of (5-{2-[(N-Acetyl-N-ethyl-amino)-methyl]-4-trifluoromethyl-phenyl}-6-methoxy-pyridin-3-yl)-acetic acid (Compound 41)

(5-{2-[(N-Benzyloxycarbonyl-N-ethyl-amino)-methyl]-4-trifluoromethyl-phenyl}-6-methoxy-pyridin-3-yl)-acetic acid ethyl ester (0.700 g, 1.3 mmol), ammonium formate (0.164 g, 2.6 mmol), and palladium on carbon (10%; 0.138 g) were combined in an evacuated flask that was backfilled with N₂. MeOH (10 mL) was added, and the resulting suspension was stirred at room temperature for 3 hours. A balloon of H₂ was added, and the reaction was stirred under an atmosphere of H₂ overnight at room temperature. The mixture was filtered through Celite, and the filtrate was concentrated. The residue was dissolved in EtOAc and washed with H₂O and brine, and then dried over Na₂SO₄, filtered, and concentrated. The crude material was purified by silica gel chromatography (0-5% MeOH in CH₂Cl₂) to give [5-(2-ethylaminomethyl-4-trifluoromethyl-phenyl)-6-methoxy-pyridin-3-yl]-acetic acid ethyl ester, which was subsequently reacted with acetyl chloride as described in Example 5, Step 4 to provide (5-{2-[(N-acetyl-N-ethyl-amino)-methyl]-4-trifluoromethyl-phenyl}-6-methoxy-pyridin-3-yl)-acetic acid ethyl ester. The ester was hydrolyzed to the acid as described in Example 3, Step 7.

Example 40

Synthesis of [5-(2-{[N-Ethyl-N-(2-methoxy-acetyl)-amino]-methyl}-4-trifluoromethyl-phenyl)-6-methoxy-pyridin-3-yl]-acetic acid (Compound 42)

[5-(2-Ethylaminomethyl-4-trifluoromethyl-phenyl)-6-methoxy-pyridin-3-yl]-acetic acid ethyl ester and methoxy-acetyl chloride were reacted as described in Example 5, Step 4 to provide [5-(2-{[N-ethyl-N-(2-methoxy-acetyl)-amino]-methyl}-4-trifluoromethyl-phenyl)-6-methoxy-pyridin-3-yl]-acetic acid ethyl ester. The ester was hydrolyzed to the acid as described in Example 3, Step 7.

Example 41

Synthesis of (5-{2-[(N-Ethoxycarbonyl-N-ethyl-amino)-methyl]-4-trifluoromethyl-phenyl}-6-methoxy-pyridin-3-yl)-acetic acid (Compound 43)

[5-(2-Ethylaminomethyl-4-trifluoromethyl-phenyl)-6-methoxy-pyridin-3-yl]-acetic acid ethyl ester and ethyl chloroformate were reacted as described in Example 5, Step 4 to provide (5-{2-[(N-ethoxycarbonyl-N-ethyl-amino)-methyl]-4-trifluoromethyl-phenyl}-6-methoxy-pyridin-3-yl)-acetic acid ethyl ester. The ester was hydrolyzed to the acid as described in Example 3, Step 7.

Example 42

Synthesis of {5-[2-({N-Ethyl-N-[2-(6-methyl-pyridin-3-yl)-acetyl]-amino}-methyl)-4-trifluoromethyl-phenyl]-pyridin-3-yl}-acetic acid (Compound 37)

{5-[2-({N-[2-(6-chloro-pyridin-3-yl)-acetyl]-N-ethyl-amino}-methyl)-4-trifluoromethyl-phenyl]-pyridin-3-yl}-acetic acid ethyl ester ester (0.120 g, 0.23 mmol), methylboronic acid (0.060 g, 0.25 mmol), and sodium bicarbonate (0.049 g, 0.58 mmol) were combined in DME (2 mL) and H₂O (1 mL). The mixture was purged with N₂ for 15 minutes, and then [1,1'-bis(diphenylphosphino)ferrocene]dichloro-palladium(II) (0.019 g, 0.023 mmol) was added, and the reaction was stirred at 85° C. in a sealed tube for 5 hours. The reaction was then heated at 100° C. overnight. The reaction was diluted with MeOH, and solid material was removed by filtration. The filtrate was purified by preparative HPLC to give the title compound.

Mass spectrometric data (M+H) for compounds are displayed in Table 1.

Example 43a

DP₂/CRTH2 Binding Assay

The ability of a compound to bind to the human DP₂ receptor is assessed via a radioligand binding assay using

[$^3$H]PGD$_2$. HEK293 cells stably expressing recombinant human DP$_2$ are resuspended in 10 mM Hepes, 7.4 containing 1 mM DTT, lysed and centrifuged at 75,000×g to pellet the membranes. The membranes are resuspended in 10 mM Hepes, 7.4 containing 1 mM DTT and 10% glycerol to approximately 5 mg protein/ml. Membranes (2-10 µg protein/well) are incubated in 96-well plates with 1 nM [$^3$H] PGD$_2$ and test compound in Assay Buffer (50 mM Hepes, 10 mM MnCl$_2$, 1 mM EDTA, plus or minus 0.2% human serum albumin, pH 7.4) for 60 minutes at room temperature. The reactions are terminated by rapid filtration through Whatman GF/C glass fibre filter plates. The filter plates were pre-soaked in 0.33% polythylenimine for 30 minutes at room temperature then washed in Wash Buffer (50 mM Hepes, 0.5 M NaCl pH 7.4) prior to harvesting. After harvesting, the filter plates are washed 3 times with 1 ml cold Wash Buffer then dried. Scintillant is then added to the plates and the radioactivity retained on the filters is determined on a Packard TopCount (Perkin Elmer). Specific binding is determined as total radioactive binding minus non-specific binding in the presence of 10 µM PGD$_2$. IC$_{50}$s were determined using GraphPad prism analysis of drug titration curves. Compounds tested had an IC$_{50}$ of less than 20 micromolar in this assay.

Example 43b

GTPγS Binding Assay

The ability of a compound to inhibit binding of GTP to DP$_2$ is assessed via a membrane GTPγS assay. CHO cells stably expressing the recombinant human CRTH2 receptor are resuspended in 10 mM Hepes, 7.4 containing 1 mM DTT, lysed and centrifuged at 75,000×g to pellet the membranes. The membranes are resuspended in 10 mM Hepes, 7.4 containing 1 mM DTT and 10% glycerol. Membranes (~12.5 µg per well) are incubated in 96-well plates with 0.05 nM [$^{35}$S]-GTPγS, 80 nM PGD$_2$, 5 µM GDP, and test compound in Assay Buffer (50 mM Hepes, pH 7.4, 100 mM NaCl, 5 mM MgCl$_2$ and 0.2% human serum albumin) for 60 minutes at 30° C. The reactions are terminated by rapid filtration through Whatman GF/B glass fibre filter plates. The filter plates are washed 3 times with 1 ml cold Assay Buffer and dried. Scintillant is then added to the plates and the radioactivity retained on the filters is determined on a Packard TopCount (Perkin Elmer). Specific binding is determined as total radioactive binding minus non-specific binding in the absence of the ligand (80 nM PGD$_2$). IC$_{50}$s were determined using Graphpad prism analysis of drug titration curves.

Example 43c

Whole Blood Esoinophil Shape Change Assay

Blood is drawn from consenting human volunteers in EDTA vacutainer tubes and used within 1 hr of draw. A 98 µl aliquot of blood is mixed with 2 µl of test compound (in 50% DMSO) in 1.2 ml polypropylene tubes. The blood is vortexed and incubated at 37° C. for 15 minutes. 5 µl of 1 µM PGD$_2$ in PBS is added for a final concentration of 50 nM and the tubes briefly vortexed. The reactions are incubated for exactly 5 minutes at 37° C. and then terminated by placing the tubes on ice and immediately adding 250 µl of ice-cold 1:4 diluted Cytofix (BD Biosciences). The reactions are transferred to 12×75 mM polystyrene round bottom tubes and the red blood cells lysed by the addition of 3 ml ammonium chloride lysing solution (150 mM NH$_4$Cl, 10 mM KHCO$_3$, 0.1 mM EDTA disodium salt) and incubation at room temperature for 15 minutes. The cells are pelleted by spinning at 1300 rpm for 5 minutes at 4° C. and washed once with 3 ml ice-cold PBS. The cells are resuspended in 0.2 ml of ice-cold 1:4 diluted Cytofix (BD Biosciences) and analyzed on a FACSCalibur (BD Biosciences) within 2 hours. Eosinophils were gated on the basis of autofluorescence in the FL2 channel and shape change on 500 eosinophils was assayed by forward scatter and side scatter analysis. The specific change in shape induced by PGD$_2$ was calculated as the difference between the percentage of high forward scatter eosinophils in the presence and absence of PGD$_2$. IC$_{50}$s were determined using Graphpad Prism® analysis of drug titration curves.

Example 43d

DP$_1$ Binding Assay

The ability of a compound to bind to the human DP1 receptor was evaluated via a radioligand membrane binding assay using the DP$_1$ selective synthetic ligand [$^3$H] BWA868C. Packed human platelets (Biological Specialty Corporation), were resuspended in 6 volumes of Hepes/HBSS buffer (10 mM Hepes, 1 mM DTT in Hanks Balanced Salt Solution (HBSS), lysed and centrifuged at 75,000×g to pellet the membranes. Membranes were resuspended in Hepes/HBSS buffer to approximately 12 mg protein/ml. Membranes (20 µg protein/well) are incubated in 96-well plates with 2 nM [$^3$H]BWA868C and test compound in Assay Buffer (50 mM Hepes, 10 mM MnCl$_2$, 1 mM EDTA, plus or minus 0.2% human serum albumin, pH 7.4) for 60 minutes at room temperature. The reactions are terminated by rapid filtration through Whatman GF/C glass fibre filter plates. The filter plates were pre-soaked in 0.33% polethylenimine for 30 minutes at room temperature then washed in Wash Buffer (50 mM Hepes, 0.5 M NaCl pH 7.4) prior to harvesting. After harvesting, the filter plates are washed 3 times with 1 ml cold Wash Buffer then dried. Scintillant is then added to the plates and the radioactivity retained on the filters is determined on a Packard TopCount (Perkin Elmer). Specific binding is determined as total radioactive binding minus non-specific binding in the presence of 10 µM BW A868C. IC$_{50}$s were determined using GraphPad prism analysis of drug titration curves.

Example 44

Mouse Allergic Rhinitis Model

The compounds ability to inhibit allergen-induced sneezing and nasal rubbing is assessed using a mouse model of allergic rhinitis. Methods were adapted from those detailed in Nakaya, M., et al. 2006, *Laboratory Investigation,* 86:917-926. Female BALB/c mice (20-25 g) are immunized by an intraperitoneal injection (i.p.) of 2 µg ovalbumin (OVA) complexed with alum in a volume 0.2 ml on days 0 and 14. Seven days later (day 21) mice are challenged intranasally with 20 µl of a 10 mg/ml solution of OVA. The challenge period occurs daily from days 21 to day 25. Mice (5-7/group) are randomly assigned to receive either compound or vehicle and are treated by oral gavage 1-2 hour prior to each OVA challenge. The number of sneezes and nasal rubs are counted by an independent blind observe during a period of 8 minutes immediately following OVA challenge on days 21, 23 and 25. A significant increase in allergen-induced sneezing and nasal rubbing occurs over the 5-day challenge period. Inhibition of this effect by select compounds is determined statistically using Graphpad prism.

Example 45

Guinea Pig IV-DKPGD2-Induced Peripheral Blood Leukocyte Influx

The compounds ability to inhibit leukocyte migration in vivo was assessed using intravenous injection of 13,14-dihydro-15-keto-prostaglandin D2 (DK-PGD2). Methods were adapted from those detailed Shichijo et al., 2003, *Journal of Pharmacology and Experimental Therapeutics*, 307:518-525. Male Hartley guinea pigs were immunized with ovalbumin (OVA) on day 0 by intraperitoneal (IP) injection of 1 ml of a 100 µg/ml solution in Inject Alum. They were then used in the DK-PGD2 procedure between days 14 and 21. Subjects were randomly assigned to receive either vehicle (0.5% methyl cellulose, 4 ml/kg, oral (PO)) or one of three to four doses of test compound. Two hours or eighteen hours after dosing, animals were anesthetized with ketamine and challenged with DK-PGD2 (1 mg/kg, IV). Thirty minutes after IV administration, blood was collected via the marginal ear vein into EDTA tubes for cell analysis. 10 µl blood was lysed in 190 µl water followed by a further 20-fold dilution in PBS. A 10 µl fraction was mixed with equal parts trypan blue and loaded on a hemocytometer. Cells were visualized at a magnification of 40× using a LabPro light microscope and totals counted and recorded. Cells are expressed as total cells×$10^8$ per ml of blood. Inhibition of this effect by select compounds is determined statistically using Graphpad prism.

The compounds that were tested in Table 1 had $IC_{50}$ below 5 µM in the CRTH2 binding assay.

TABLE 2

Representative Biological Data

| Compound Number | hDP2 (µM) |
|---|---|
| Compound 1 | A |
| Compound 2 | A |
| Compound 3 | A |
| Compound 4 | A |
| Compound 5 | A |
| Compound 6 | B |
| Compound 7 | B |
| Compound 8 | A |
| Compound 9 | B |
| Compound 10 | A |
| Compound 11 | B |
| Compound 12 | A |
| Compound 13 | A |
| Compound 14 | A |
| Compound 15 | A |
| Compound 16 | A |
| Compound 17 | A |
| Compound 18 | A |
| Compound 19 | A |
| Compound 20 | A |
| Compound 21 | A |
| Compound 22 | A |
| Compound 23 | B |
| Compound 24 | A |
| Compound 25 | A |
| Compound 26 | A |
| Compound 27 | A |
| Compound 28 | A |
| Compound 29 | B |
| Compound 30 | C |
| Compound 31 | A |
| Compound 32 | A |
| Compound 33 | A |
| Compound 34 | B |
| Compound 35 | B |
| Compound 36 | B |
| Compound 37 | A |
| Compound 38 | B |
| Compound 39 | A |
| Compound 40 | A |
| Compound 41 | B |
| Compound 42 | A |
| Compound 43 | A |
| Ramatroban | B |

A = less than 0.3 µM; B = greater than 0.3 µM and less than 1 µM; C = greater than 1 µM.

Example 46

Clinical Trials in Humans

Study 1: Clinical Trial Evaluating Effect of Compound of Formula (I) on ex vivo PGD2-Induced Blood Eosinophil Shape Change In this double-blind, randomized, placebo-controlled, single ascending dose study of Compound of Formula (I) in healthy volunteers the inhibition of ex vivo $PGD_2$-induced blood eosinophil shape change is determined to show proof of biochemical mechanism of DP2 receptor antagonism. Eight subjects (6 active, 2 placebo) per dose level are used. Pre dose blood is drawn and challenged with $PGD_2$ to determine baseline shape change as described above in Example 43. At varying times after dosing blood is drawn for both pharmacokinetic analyses of drug concentration in blood, and also for $PGD_2$ challenge and eosinophil shape change determination. The extent of receptor blockage is determined from the relationship between drug blood concentration and percentage inhibition of eosinophil shape change.

Study 2: Clinical Trial Evaluating Effect of Compound of Formula (I) on Allergen-Induced Nasal Symptoms and Inflammatory and Allergic Biomarkers In this double-blind, randomized, placebo-controlled study of Compound of Formula (I) in individuals with allergic rhinitis the inhibition of nasal symptoms and allergic biomarkers is determined following nasal challenge with appropriate allergen. Fifteen subjects (10 active, 5 placebo) are used. Subjects are dosed for 7 days with either placebo or an amount of compound of formula (I) that results in complete DP2 receptor block in an ex vivo $PGD_2$-induced blood eosinophil shape change pharmacodynamic study as described above. On day 7 subjects undergo nasal allergen challenge (2 hours post-dose) and early allergic response (0.25-1.0 hr) and late allergic response (4-24 hr) are evaluated as an increase from baseline for treated vs placebo. In addition changes in inflammatory cell differentials, Th2 cytokines and other inflammatory markers are determined as increase from baseline for treated vs. placebo.

Compound of Formula (I) Assay

The plasma concentrations of compound of Formula (I) are determined by gas chromatography, giving a detection limit of 1 ng·ml-1 (Ritter W. Determination of BAY u 3405, a novel thromboxane antagonist, in plasma and urine by HPLC and GC. In: Reid E, Wilson I D, eds. Bioanalytical Approaches for Drugs, Including Anti-asthmatics and Metabolites. Methodological Surveys in Biochemistry and Analysis, 1992; 22: 211-216).

Study 3—Vienna Challenge Chamber Study

Study design: The study is a randomised, double blind, placebo controlled, two way crossover evaluation of compound of Formula (I), given orally for eight days. There is a screening period of one week and a washout period of three weeks between the two treatment periods.

There is a follow up one week after the last dose of study drug. The group of patients who receive the study drug for the first treatment period and placebo for the second are designated group A, while the group of patients who receive placebo for the first treatment period and the study drug for the second treatment period are designated group B.

Treatment plan and methods: The subjects undergo a complete screening assessment to determine a baseline response to allergens. This screening assessment takes place one week prior to the start of dosing.

Subjects commence dosing with compound of Formula (I) or placebo on Day 1 of each treatment period of the study. Adverse events, total nasal symptom score and concomitant medications are noted.

Subjects report back to the clinic on Day 2 of each treatment period for a 6 hour allergen challenge. The following measurements are obtained:
   Total nasal symptom score (TNSS) (obstruction, rhinorrhoea, itch, sneeze) with each symptom scored on a categorical scale from 0 to 3 pre-challenge, every 15 mins from 0 to 6 h post-start of challenge
   Eye symptom score (watery eyes, itchy eyes, red eyes) with each symptom scored on a categorical scale from 0 to 3 pre-challenge, every 15 mins from 0 to 6 h post-start of challenge
   Other symptoms (cough, itchy throat, itchy ears) with each symptom scored on a categorical scale from 0 to 3 pre-challenge and every 15 mins from 0 to 6 h post-start of challenge Subjects report back to the clinic on Day 8 of each treatment period for a 6 hour allergen challenge and the measurements obtained on Day 2 are repeated.

A final follow-up visit is conducted one week after the last dose of test article in Treatment Period 2.

Example 47a

Parenteral Composition

To prepare a parenteral pharmaceutical composition suitable for administration by injection, 100 mg of a water-soluble salt of a compound of Formula (I) is dissolved in DMSO and then mixed with 10 mL of 0.9% sterile saline. The mixture is incorporated into a dosage unit form suitable for administration by injection.

Example 47b

Oral Composition

To prepare a pharmaceutical composition for oral delivery, 100 mg of a compound of Formula (I) is mixed with 750 mg of starch. The mixture is incorporated into an oral dosage unit for, such as a hard gelatin capsule, which is suitable for oral administration.

Example 47c

Sublingual (Hard Lozenge) Composition

To prepare a pharmaceutical composition for buccal delivery, such as a hard lozenge, mix 100 mg of a compound of Formula (I) with 420 mg of powdered sugar mixed, with 1.6 mL of light corn syrup, 2.4 mL distilled water, and 0.42 mL mint extract. The mixture is gently blended and poured into a mold to form a lozenge suitable for buccal administration.

Example 47d

Fast-Disintegrating Sublingual Tablet

A fast-disintegrating sublingual tablet is prepared by mixing 48.5% by weigh of a compound of Formula (I), 44.5% by weight of microcrystalline cellulose (KG-802), 5% by weight of low-substituted hydroxypropyl cellulose (50 μm), and 2% by weight of magnesium stearate. Tablets are prepared by direct compression (*AAPS Pharm Sci Tech*. 2006; 7(2):E41). The total weight of the compressed tablets is maintained at 150 mg. The formulation is prepared by mixing the amount of compound of Formula (I) with the total quantity of microcrystalline cellulose (MCC) and two-thirds of the quantity of low-substituted hydroxypropyl cellulose (L-HPC) by using a three dimensional manual mixer (Inversina®, Bioengineering AG, Switzerland) for 4.5 minutes. All of the magnesium stearate (MS) and the remaining one-third of the quantity of L-HPC are added 30 seconds before the end of mixing.

Example 47e

Inhalation Composition

To prepare a pharmaceutical composition for inhalation delivery, 20 mg of a compound of Formula (I) is mixed with 50 mg of anhydrous citric acid and 100 mL of 0.9% sodium chloride solution. The mixture is incorporated into an inhalation delivery unit, such as a nebulizer, which is suitable for inhalation administration.

Example 47f

Rectal Gel Composition

To prepare a pharmaceutical composition for rectal delivery, 100 mg of a compound of Formula (I) is mixed with 2.5 g of methylcelluose (1500 mPa), 100 mg of methylparaben, 5 g of glycerin and 100 mL of purified water. The resulting gel mixture is then incorporated into rectal delivery units, such as syringes, which are suitable for rectal administration.

Example 47 g

Topical Gel Composition

To prepare a pharmaceutical topical gel composition, 100 mg of a compound of Formula (I) is mixed with 1.75 g of hydroxypropyl celluose, 10 mL of propylene glycol, 10 mL of isopropyl myristate and 100 mL of purified alcohol USP. The resulting gel mixture is then incorporated into containers, such as tubes, which are suitable for topical administration.

Example 47h

Ophthalmic Solution Composition

To prepare a pharmaceutical opthalmic solution composition, 100 mg of a compound of Formula (I) is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration.

Example 47i

Nasal Spray Solution

To prepare a pharmaceutical nasal spray solution, 10 g of a compound of Formula (I) is mixed with 30 mL of a 0.05M phosphate buffer solution (pH 4.4). The solution is placed in a nasal administrator designed to deliver 100 μl of spray for each application.

The examples and embodiments described herein are for illustrative purposes only and various modifications or changes suggested to persons skilled in the art are to be included within the spirit and purview of this application and scope of the appended claims.

What is claimed is:

1. A compound having the structure of Formula (I), pharmaceutically acceptable salt or N-oxide thereof:

wherein,
$R^A$ is H, halogen, —CN, —OH, $C_1$-$C_4$alkyl, $C_1$-$C_4$fluoroalkyl, $C_1$-$C_4$fluoroalkoxy, or $C_1$-$C_4$alkoxy;
$R^B$ is H, halogen, —CN, —OH, $C_1$-$C_4$alkyl, $C_1$-$C_4$fluoroalkyl, $C_1$-$C_4$fluoroalkoxy, or $C_1$-$C_4$alkoxy;
$R^6$ is H, halogen, —CN, tetrazolyl, —OH, —$SR^{13}$, —S(=O)$R^{12}$, —S(=O)$_2R^{12}$, —NHS(=O)$_2R^{12}$, —C(=O)$R^{12}$, —OC(=O)$R^{12}$, —CO$_2R^{13}$, —N($R^{13}$)$_2$, —C(=O)N($R^{13}$)$_2$, —NHC(=O)$R^{12}$, $C_1$-$C_4$alkyl, $C_1$-$C_4$fluoroalkyl, $C_1$-$C_4$fluoroalkoxy, $C_1$-$C_4$alkoxy, or $C_1$-$C_4$heteroalkyl;
$R^{10}$ is $C_1$-$C_4$alkyl, $C_1$-$C_4$fluoroalkyl, $C_3$-$C_6$cycloalkyl, a substituted or unsubstituted phenyl, a substituted or unsubstituted 6-membered heteroaryl containing 1 or 2 N atom, —$C_1$-$C_2$alkyl-(substituted or unsubstituted phenyl), —$C_1$-$C_2$alkyl-(substituted or unsubstituted 6-membered heteroaryl containing 1 or 2 N atom), —$C_1$-$C_2$alkyl-O—$C_1$-$C_4$alkyl, —O—$C_1$-$C_4$alkyl, —O—$C_1$-$C_2$alkyl-(substituted or unsubstituted phenyl), —$NR^{16}$—$C_1$-$C_4$alkyl, or —$NR^{16}$—$C_1$-$C_2$alkyl-(substituted or unsubstituted phenyl);
$R^{11}$ is $C_1$-$C_4$alkyl, $C_1$-$C_4$haloalkyl, $C_3$-$C_6$cycloalkyl, or substituted or unsubstituted benzyl;
$R^{12}$ is $C_1$-$C_4$alkyl, $C_1$-$C_4$heteroalkyl, or $C_1$-$C_4$fluoroalkyl;
each $R^{13}$ is independently selected from H, $C_1$-$C_4$alkyl, $C_1$-$C_4$heteroalkyl, $C_1$-$C_4$fluoroalkyl, and substituted or unsubstituted benzyl; and
$R^{16}$ is H or $C_1$-$C_4$alkyl;
where each substituted phenyl or substituted heteroaryl is substituted with 1 or 2 $R^C$, where each $R^C$ is independently selected from halogen, —OH, $C_1$-$C_4$alkyl, $C_1$-$C_4$fluoroalkyl, $C_1$-$C_4$fluoroalkoxy, and $C_1$-$C_4$alkoxy.

2. The compound of claim 1, or a pharmaceutically acceptable salt or N-oxide thereof, wherein:
$R^A$ is H, F, Cl, Br, —CN, —OH, —CH$_3$, —CF$_3$, —OCF$_3$, —OCH$_2$CF$_3$, —OCH$_3$ or —OCH$_2$CH$_3$;
$R^B$ is H, F, Cl, Br, —CN, —OH, —CH$_3$, —CF$_3$, —OCF$_3$, —OCH$_2$CF$_3$, —OCH$_3$ or —OCH$_2$CH$_3$;
$R^6$ is H, F, Cl, Br, —CN, —OH, —$SR^{13}$, —S(=O)$R^{12}$, —S(=O)$_2R^{12}$, —NHS(=O)$_2R^{12}$, —CO$_2R^{13}$, —C(=O)NH($R^{13}$), —NHC(=O)$R^{12}$, —CH$_3$, —CF$_3$, —OCF$_3$, or —OCH$_3$;
$R^{12}$ is $C_1$-$C_4$alkyl; and
$R^{13}$ is H, $C_1$-$C_4$alkyl, or substituted or unsubstituted benzyl.

3. The compound of claim 2, or a pharmaceutically acceptable salt or N-oxide thereof, wherein:
$R^{10}$ is $C_1$-$C_4$alkyl, $C_3$-$C_6$cycloalkyl, —$C_1$-$C_2$alkyl-(substituted or unsubstituted phenyl), —$C_1$-$C_2$alkyl-(substituted or unsubstituted 6-membered heteroaryl containing 1 or 2 N atom), —$C_1$-$C_2$alkyl-O—$C_1$-$C_4$alkyl, —O—$C_1$-$C_4$alkyl, —O—$C_1$-$C_2$alkyl-(substituted or unsubstituted phenyl), —$NR^{16}$$C_1$-$C_4$alkyl, or —$NR^{16}$$C_1$-$C_2$alkyl-(substituted or unsubstituted phenyl); and
$R^{11}$ is $C_1$-$C_4$alkyl, $C_3$-$C_6$cycloalkyl or substituted or unsubstituted benzyl.

4. The compound of claim 3, or a pharmaceutically acceptable salt or N-oxide thereof, wherein:
$R^{10}$ is —CH$_3$, —CH$_2$CH$_3$, —CH(CH$_3$)$_2$, —C(CH$_3$)$_3$, cyclopropyl, cyclobutyl, cyclopentyl, cyclohexyl, —CH$_2$OCH$_3$, —CH$_2$OCH$_2$CH$_3$, —$C_1$-$C_2$alkyl-(substituted or unsubstituted phenyl), —$C_1$-$C_2$alkyl-(substituted or unsubstituted 6-membered heteroaryl containing 1 or 2 N atom); where each substituted phenyl or substituted heteroaryl is substituted with 1 or 2 $R^C$, where each $R^C$ is independently selected from halogen, —OH, —CH$_3$, —CH$_2$CH$_3$, —OCH$_3$, —OCH$_2$CH$_3$, and —CF$_3$; and
$R^{11}$ is —CH$_3$, —CH$_2$CH$_3$, or cyclopropyl.

5. The compound of claim 4, or a pharmaceutically acceptable salt or N-oxide thereof, wherein:
$R^B$ is H;
$R^6$ is F, Cl, Br, —CH$_3$, —CF$_3$, —OCF$_3$, or —OCH$_3$; and
$R^{10}$ is —CH$_3$, cyclopropyl, —CH$_2$OCH$_3$, or —CH$_2$OCH$_2$CH$_3$.

6. The compound of claim 4, or a pharmaceutically acceptable salt or N-oxide thereof, wherein:
$R^B$ is H; and
$R^{11}$ is —CH$_2$CH$_3$.

7. The compound of claim 1, or a pharmaceutically acceptable salt or N-oxide thereof, wherein:
$R^{10}$ is $C_1$-$C_4$alkyl, or $C_3$-$C_6$cycloalkyl; and
$R^{11}$ is substituted or unsubstituted benzyl.

8. The compound of claim 7, or a pharmaceutically acceptable salt or N-oxide thereof, wherein:
$R^B$ is H;
$R^6$ is F, Cl, Br, —CN, —OH, —$SR^{13}$, —S(=O)$R^{12}$, —S(=O)$_2R^{12}$, —NHS(=O)$_2R^{12}$, —CO$_2R^{13}$, —C(=O)NH($R^{13}$), —NHC(=O)$R^{12}$, —CH$_3$, —CF$_3$, —OCF$_3$, or —OCH$_3$;
$R^{10}$ is —CH$_3$, or cyclopropyl; and
$R^{11}$ is substituted or unsubstituted benzyl.

9. The compound of claim 3, or a pharmaceutically acceptable salt or N-oxide thereof, wherein:
$R^{10}$ is —O—$C_1$-$C_4$alkyl or —O—$C_1$-$C_2$alkyl-(substituted or unsubstituted phenyl).

10. The compound of claim 9, or a pharmaceutically acceptable salt or N-oxide thereof, wherein:
$R^{10}$ is —O—CH$_2$— (substituted or unsubstituted phenyl) or —O—CH(CH$_3$)-(substituted or unsubstituted phenyl); where each substituted phenyl is substituted with 1 or 2 $R^C$, where each $R^C$ is independently selected from halogen, —OH, —CH$_3$, —CH$_2$CH$_3$, —OCH$_3$, —OCH$_2$CH$_3$, and —CF$_3$; and
$R^{11}$ is C$_1$-C$_4$alkyl or C$_3$-C$_6$cycloalkyl.

11. The compound of claim 10, or a pharmaceutically acceptable salt or N-oxide thereof, wherein:
$R^B$ is H;
$R^6$ is F, Cl, Br, —CH$_3$, —CF$_3$, —OCF$_3$, or —OCH$_3$;
$R^{10}$ is —O—CH$_2$— (substituted or unsubstituted phenyl), where the substituted phenyl is substituted with 1 or 2 $R^C$, where each $R^C$ is independently selected from F, Cl, Br, —OH, —CH$_3$, —OCH$_3$, and —CF$_3$; and
$R^{11}$ is C$_1$-C$_4$alkyl.

12. The compound of claim 11, or a pharmaceutically acceptable salt or N-oxide thereof, wherein:
$R^4$ is H, F, Cl, —CH$_3$, —CF$_3$, —OCF$_3$, or —OCH$_3$;
$R^6$ is —CF$_3$; and
$R^{11}$ is —CH$_2$CH$_3$.

13. The compound of claim 3, or a pharmaceutically acceptable salt or N-oxide thereof, wherein:
$R^{10}$ is —NR$^{16}$C$_1$-C$_4$alkyl, or —NR$^{16}$C$_1$-C$_2$alkyl-(substituted or unsubstituted phenyl); and
$R^{16}$ is H, —CH$_3$ or —CH$_2$CH$_3$.

14. The compound of claim 13, or a pharmaceutically acceptable salt or N-oxide thereof, wherein:
$R^{10}$ is —NR$^{16}$—CH$_2$— (substituted or unsubstituted phenyl) or —NR$^{16}$—CH(CH$_3$)-(substituted or unsubstituted phenyl), where the substituted phenyl is substituted with 1 or 2 $R^C$, where each $R^C$ is independently selected from F, Cl, Br, —OH, —CH$_3$, —OCH$_3$, and —CF$_3$;
$R^{11}$ is C$_1$-C$_4$alkyl or C$_3$-C$_6$cycloalkyl; and
$R^{16}$ is H, —CH$_3$ or —CH$_2$CH$_3$.

15. The compound of claim 14, or a pharmaceutically acceptable salt or N-oxide thereof, wherein:
$R^B$ is H;
$R^6$ is F, Cl, Br, —CH$_3$, —CF$_3$, —OCF$_3$, or —OCH$_3$;
$R^{10}$ is —NR$^{16}$—CH$_2$— (substituted or unsubstituted phenyl); where the substituted phenyl is substituted with 1 or 2 $R^C$, where each $R^C$ is independently selected from F, Cl, Br, —OH, —CH$_3$, —OCH$_3$, and —CF$_3$; and
$R^{11}$ is C$_1$-C$_4$alkyl.

16. The compound of claim 15, or a pharmaceutically acceptable salt or N-oxide thereof, wherein:
$R^4$ is H, F, Cl, —CH$_3$, —CF$_3$, —OCF$_3$, or —OCH$_3$;
$R^6$ is —CF$_3$; and
$R^{11}$ is —CH$_2$CH$_3$.

17. The compound of claim 1 selected from among:
3-[(N-Benzyloxycarbonyl-N-ethyl-amino)-methyl]-4-(5-carboxymethyl-pyridin-3-yl)-benzoic acid; 4-(5-Carboxymethyl-pyridin-3-yl)-3-[(N-cyclopropanecarbonyl-N-ethyl-amino)-methyl]-benzoic acid; (5-{2-[(N-Benzyl-N-cyclopropanecarbonyl-amino)-methyl]-4-cyano-phenyl}-pyridin-3-yl)-acetic acid; {5-[2-[(N-Benzyl-N-cyclopropanecarbonyl-amino)-methyl]-4-(2H-tetrazol-5-yl)-phenyl]-pyridin-3-yl}-acetic acid; (5-{4-Benzylcarbamoyl-2-[(N-benzyl-N-cyclopropanecarbonyl-amino)-methyl]-phenyl}-pyridin-3-yl)-acetic acid; (5-{2-[(N-Benzyl-N-cyclopropanecarbonyl-amino)-methyl]-4-methylcarbamoyl-phenyl}-pyridin-3-yl)-acetic acid; (5-{2-[(N-Benzyl-N-cyclopropanecarbonyl-amino)-methyl]-4-tert-butylcarbamoyl-phenyl}-pyridin-3-yl)-acetic acid; (5-{2-[(N-Cyclopropanecarbonyl-N-ethyl-amino)-methyl]-4-trifluoromethyl-phenyl}-pyridin-3-yl)-acetic acid; (2-Chloro-5-{2-[(N-cyclopropanecarbonyl-N-ethyl-amino)-methyl]-4-trifluoromethyl-phenyl}-pyridin-3-yl)-acetic acid; (5-{2-[(N-Cyclopropanecarbonyl-N-ethyl-amino)-methyl]-4-trifluoromethyl-phenyl}-6-methoxy-pyridin-3-yl)-acetic acid; (6-Chloro-5-{2-[(N-cyclopropanecarbonyl-N-ethyl-amino)-methyl]-4-trifluoromethyl-phenyl}-pyridin-3-yl)-acetic acid; (5-{2-[(N-Benzyloxycarbonyl-N-ethyl-amino)-methyl]-4-trifluoromethyl-phenyl}-pyridin-3-yl)-acetic acid; (5-{2-[(N-tert-Butoxycarbonyl-N-ethyl-amino)-methyl]-4-trifluoromethyl-phenyl}-pyridin-3-yl)-acetic acid; {5-[2-(3-Benzyl-1-ethyl-ureidomethyl)-4-trifluoromethyl-phenyl]-pyridin-3-yl}-acetic acid; (5-{2-[(N-Benzyloxycarbonyl-N-ethyl-amino)-methyl]-4-trifluoromethyl-phenyl}-1-oxy-pyridin-3-yl)-acetic acid; (5-{2-[(N-Ethyl-N-phenylacetyl-amino)-methyl]-4-trifluoromethyl-phenyl}-pyridin-3-yl)-acetic acid; (5-{2-[(N-Benzyl-N-cyclopropanecarbonyl-amino)-methyl]-4-trifluoromethyl-phenyl}-pyridin-3-yl)-acetic acid; (5-{2-[(N-Acetyl-N-benzyl-amino)-methyl]-4-trifluoromethyl-phenyl}-pyridin-3-yl)-acetic acid; (5-{2-[(N-Acetyl-N-benzyl-amino)-methyl]-4-trifluoromethyl-phenyl}-6-chloro-pyridin-3-yl)-acetic acid; (5-{2-[(N-Acetyl-N-benzyl-amino)-methyl]-4-trifluoromethyl-phenyl}-2-chloro-pyridin-3-yl)-acetic acid; (5-{2-[(N-Cyclopropanecarbonyl-N-ethyl-amino)-methyl]-4-methylsulfanyl-phenyl}-pyridin-3-yl)-acetic acid; (5-{4-tert-Butylsulfanyl-2-[(N-cyclopropanecarbonyl-N-ethyl-amino)-methyl]-phenyl}-pyridin-3-yl)-acetic acid; (5-{2-[(N-Cyclopropanecarbonyl-N-ethyl-amino)-methyl]-4-fluoro-phenyl}-pyridin-3-yl)-acetic acid; (5-{2-[(N-Cyclopropanecarbonyl-N-ethyl-amino)-methyl]-4-mercapto-phenyl}-pyridin-3-yl)-acetic acid; [5-(2-{[N-Ethyl-N-(3-phenyl-propionyl)-amino]-methyl}-4-trifluoromethyl-phenyl)-pyridin-3-yl]-acetic acid; (5-{2-[(N-Acetyl-N-benzyl-amino)-methyl]-4-trifluoromethyl-phenyl}-6-hydroxy-pyridin-3-yl)-acetic acid; {5-[2-(3-Benzyl-1-ethyl-ureidomethyl)-4-trifluoromethyl-phenyl]-6-methoxy-pyridin-3-yl}-acetic acid; (5-{2-[(N-Acetyl-N-benzyl-amino)-methyl]-4-trifluoromethyl-phenyl}-6-methoxy-pyridin-3-yl)-acetic acid; [5-(2-{[N-Ethyl-N-(pyrazine-2-carbonyl)-amino]-methyl}-4-trifluoromethyl-phenyl)-pyridin-3-yl]-acetic acid; [5-(2-{[N-(2,4-Dimethoxy-pyrimidine-5-carbonyl)-N-ethyl-amino]-methyl}-4-trifluoromethyl-phenyl)-pyridin-3-yl]-acetic acid; {5-[2-({N-[2-(6-Chloro-pyridin-3-yl)-acetyl]-N-ethyl-amino}-methyl)-4-trifluoromethyl-phenyl]-pyridin-3-yl}-acetic acid; {5-[2-({N-[2-(4,6-Diethoxy-pyrimidin-2-yl)-acetyl]-N-ethyl-amino}-methyl)-4-trifluoromethyl-phenyl]-pyridin-3-yl}-acetic acid; [5-(2-{[N-Ethyl-N-(2-pyridin-2-yl-acetyl)-amino]-methyl}-4-trifluoromethyl-phenyl)-pyridin-3-yl]-acetic acid; [5-(2-{[N-Ethyl-N-(2-methoxy-acetyl)-amino]-methyl}-4-trifluoromethyl-phenyl)-pyridin-3-yl]-acetic acid; [5-(2-{[N-(2-Ethoxy-acetyl)-N-ethyl-amino]-methyl}-4-trifluoromethyl-phenyl)-pyridin-3-yl]-acetic acid; [5-(2-{[N-Ethyl-N-(3-pyridin-3-yl-propionyl)-amino]-methyl}-4-trifluoromethyl-phenyl)-pyridin-3-yl]-acetic acid; {5-[2-({N-Ethyl-N-[2-(6-methyl-pyridin-3-yl)-acetyl]-amino}-methyl)-4-trifluoromethyl-phenyl]-pyridin-3-yl}-acetic acid; (5-{2-[(N-Cyclopropanecarbonyl-N-ethyl-amino)-methyl]-4-trifluoromethyl-phenyl}-6-hydroxy-pyridin-3-yl)-acetic acid; [5-{2-[(N-Cyclopropanecarbonyl-N-ethyl-amino)-methyl]-4-trifluoromethyl-phenyl}-6-(2,2,2-trifluoro-ethoxy)-pyridin-3-yl]-acetic acid; (5-{2-[(N-Benzyloxycarbonyl-N-ethyl-amino)-methyl]-4-trifluoromethyl-phenyl}-6-methoxy-pyridin-3-yl)-acetic acid; (5-{2-[(N-Acetyl-N-ethyl-amino)-methyl]-4-trifluoromethyl-phenyl}-6-methoxy-pyridin-3-yl)-acetic acid; [5-(2-{[N-Ethyl-N-(2-methoxy-acetyl)-amino]-methyl}-4-trifluoromethyl-phenyl)-6-methoxy-pyridin-3-yl]-acetic acid; and (5-{2-[N-(Ethoxycarbonyl-N-ethyl-amino)-methyl]-4-trifluoromethyl-phenyl}-6-methoxy-pyridin-3-yl)-acetic acid; or a pharmaceutically acceptable salt or N-oxide thereof.

18. A pharmaceutical composition comprising a therapeutically effective amount of a compound of claim 1, or a pharmaceutically acceptable salt or N-oxide thereof, and at least one pharmaceutically acceptable inactive ingredient selected from pharmaceutically acceptable diluents, pharmaceutically acceptable excipients, and pharmaceutically acceptable carriers.

19. The pharmaceutical composition of claim 18, wherein the pharmaceutical composition is formulated for intravenous injection, oral administration, inhalation, nasal administration, topical administration, ophthalmic administration or otic administration.

20. The pharmaceutical composition of claim 18, wherein the pharmaceutical composition is a tablet, a pill, a capsule, a liquid, an inhalant, a nasal spray solution, a suppository, a suspension, a gel, a colloid, a dispersion, a suspension, a solution, an emulsion, an ointment, a lotion, an eye drop or an ear drop.

21. The compound of claim 1, or a pharmaceutically acceptable salt or N-oxide thereof, wherein the compound has the following structure:

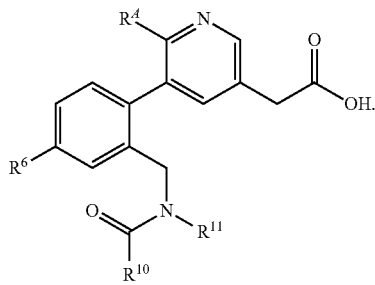

22. The compound of claim 1, wherein the compound is (5-{2-[(N-Cyclopropanecarbonyl-N-ethyl-amino)-methyl]-4-trifluoromethyl-phenyl}-6-methoxy-pyridin-3-yl)-acetic acid; or a pharmaceutically acceptable salt or N-oxide thereof.

23. The compound of claim 22, wherein the pharmaceutically acceptable salt is a sodium salt.

24. The compound of claim 1, wherein the compound is (5-{2-[(N-Benzyloxycarbonyl-N-ethyl-amino)-methyl]-4-trifluoromethyl-phenyl}-pyridin-3-yl)-acetic acid; or a pharmaceutically acceptable salt or N-oxide thereof.

25. The compound of claim 24, wherein the pharmaceutically acceptable salt is a sodium salt.

26. The compound of claim 1, wherein the compound is (5-{2-[(N-Ethyl-N-phenylacetyl-amino)-methyl]-4-trifluoromethyl-phenyl}-pyridin-3-yl)-acetic acid; or a pharmaceutically acceptable salt or N-oxide thereof.

27. The compound of claim 26, wherein the pharmaceutically acceptable salt is a sodium salt.

28. The compound of claim 1, wherein the compound is (5-{2-[(N-Acetyl-N-benzyl-amino)-methyl]-4-trifluoromethyl-phenyl}-6-methoxy-pyridin-3-yl)-acetic acid; or a pharmaceutically acceptable salt or N-oxide thereof.

29. The compound of claim 28, wherein the pharmaceutically acceptable salt is a sodium salt.

30. The compound of claim 1, wherein the compound is (5-{2-[(N-Benzyloxycarbonyl-N-ethyl-amino)-methyl]-4-trifluoromethyl-phenyl}-6-methoxy-pyridin-3-yl)-acetic acid; or a pharmaceutically acceptable salt or N-oxide thereof.

31. The compound of claim 30, wherein the pharmaceutically acceptable salt is a sodium salt.

32. The compound of claim 17, wherein the pharmaceutically acceptable salt is a sodium salt.

33. A method for treating a $PGD_2$-dependent or a $PGD_2$-mediated disease or condition in a mammal, wherein the disease or condition is selected from an allergic disease or condition, asthma, and chronic obstructive pulmonary disease (COPD), comprising administering to the mammal a therapeutically effective amount of a compound of claim 1, or a pharmaceutically acceptable salt or N-oxide thereof.

34. The method of claim 33, wherein the disease or condition is asthma.

35. The method of claim 33, wherein the disease or condition is chronic obstructive pulmonary disease (COPD).

36. The method of claim 33, wherein the disease or condition is allergic rhinitis.

* * * * *